US008252541B2

(12) United States Patent
McCormack et al.

(10) Patent No.: US 8,252,541 B2
(45) Date of Patent: Aug. 28, 2012

(54) SODIUM CHANNEL PROTEIN TYPE III α-SUBUNIT SPLICE VARIANT

(75) Inventors: Kenneth John McCormack, Raleigh, NC (US); Christopher Dinesh Raj, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/018,908

(22) Filed: Feb. 1, 2011

(65) Prior Publication Data

US 2011/0117112 A1 May 19, 2011

Related U.S. Application Data

(62) Division of application No. 12/416,777, filed on Apr. 1, 2009, now Pat. No. 7,915,385, which is a division of application No. 11/357,518, filed on Feb. 17, 2006, now Pat. No. 7,531,523.

(60) Provisional application No. 60/654,019, filed on Feb. 17, 2005.

(51) Int. Cl.
*C12Q 1/68* (2006.01)
*G01N 33/53* (2006.01)
(52) U.S. Cl. .............................. 435/7.1; 435/6
(58) Field of Classification Search ............ None
See application file for complete search history.

(56) References Cited

U.S. PATENT DOCUMENTS

| | | | |
|---|---|---|---|
| 4,554,101 A | 11/1985 | Hopp | |
| 4,861,719 A | 8/1989 | Miller | |
| 5,093,246 A | 3/1992 | Cech et al. | |
| 5,139,941 A | 8/1992 | Muzyczka et al. | |
| 5,252,479 A | 10/1993 | Srivastava | |
| 5,328,688 A | 7/1994 | Roizman | |
| 5,380,836 A | 1/1995 | Rogart | |
| 5,437,982 A | 8/1995 | Catterall et al. | |
| 5,474,935 A | 12/1995 | Chatterjee et al. | |
| 5,585,362 A | 12/1996 | Wilson et al. | |
| 5,622,856 A | 4/1997 | Natsoulis | |
| 5,658,776 A | 8/1997 | Flotte et al. | |
| 5,661,033 A | 8/1997 | Ho et al. | |
| 5,670,488 A | 9/1997 | Gregory et al. | |
| 5,686,278 A | 11/1997 | Williams et al. | |
| 5,693,509 A | 12/1997 | Cotten et al. | |
| 5,693,756 A | 12/1997 | Li et al. | |
| 5,707,618 A | 1/1998 | Armentano et al. | |
| 5,770,414 A | 6/1998 | Gage et al. | |
| 5,773,289 A | 6/1998 | Samulski et al. | |
| 5,776,859 A | 7/1998 | Nickel | |
| 5,789,390 A | 8/1998 | Descamps et al. | |
| 5,824,544 A | 10/1998 | Armentano et al. | |
| 5,830,725 A | 11/1998 | Nolan et al. | |
| 5,830,727 A | 11/1998 | Wang et al. | |
| 5,834,441 A | 11/1998 | Philip et al. | |
| 5,849,571 A | 12/1998 | Glorioso et al. | |
| 5,851,521 A | 12/1998 | Branellec et al. | |
| 5,856,152 A | 1/1999 | Wilson et al. | |
| 5,863,541 A | 1/1999 | Samulski et al. | |
| 5,879,934 A | 3/1999 | DeLuca | |
| 5,888,502 A | 3/1999 | Guber et al. | |
| 5,892,018 A | 4/1999 | Welsh et al. | |
| 6,030,810 A | 2/2000 | Delgado et al. | |
| 6,060,271 A | 5/2000 | Walewski et al. | |
| 6,184,349 B1 | 2/2001 | Herman et al. | |
| 6,335,172 B1 | 1/2002 | Delgado et al. | |
| 6,479,259 B1 | 11/2002 | Herman et al. | |
| 6,479,498 B1 | 11/2002 | Marquess et al. | |
| 6,559,154 B2 | 5/2003 | Kang et al. | |
| 6,607,741 B2 | 8/2003 | Boucher, Jr. | |
| 6,613,345 B2 | 9/2003 | Boucher, Jr. | |
| 6,646,012 B2 | 11/2003 | Choi et al. | |
| 6,686,193 B2 | 2/2004 | Maher et al. | |
| 6,756,400 B2 | 6/2004 | Chinn et al. | |

FOREIGN PATENT DOCUMENTS

| | | |
|---|---|---|
| WO | WO-84/03564 | 9/1984 |
| WO | WO-91/09955 | 7/1991 |
| WO | WO-92/20808 | 11/1992 |
| WO | WO-93/23569 | 11/1993 |
| WO | WO-96/12650 | 5/1996 |
| WO | WO-01/96552 | 12/2001 |
| WO | WO-2004/050857 | 6/2004 |
| WO | WO-2005/059101 | 6/2005 |

OTHER PUBLICATIONS

Balazy, Clinical management of chronic pain in spinal cord injury. *Clin. J. Pain*, 8:102-10 (1992).
Black et al., Sodium channel mRNAs I, II and III in the CNS: Cell specific expression. *Brain Res. Mol. Brain Res.*, 22(1-4):275-289 (1994).
Catterall, Structure and function of voltage-gated ion channels. *Annu. Rev. Biochem.* 64:493-531 (1995).
Chen et al., Cloning, distribution and functional analysis of the type III sodium channel from human brain. *Eur. J. Neurosci.*, 12:4281-4289 (2000).
Crooke et al., Antisense Research and Applications, CRC Press, (1993).
Database EMBL, "*Homo sapiens* voltage-gated Sodium Channel Type III Alpha Subunit (SCN3A) Gene, Exons 12 and 12b" (2001).
Database UniProt, "Sodium Channel Protein Type 3 Subunit Alpha (Sodium Channel Protein DE Type II Subunit Alpha) (Voltage-gated Sodium Channel Subunit Alpha Nav1.3) (Sodium Channel Protein, Brain III Subunit Alpha) (Voltage-gated Sodium Channel Subunit III)" (2001).
Dixon, Efficient analysis of experimental observations. *Ann. Rev. Pharmacol. Toxicol.*, 20:441-462 (1980).
Drew et al., Responses of spinal neurons to cutaneous and dorsal root stimuli in rats with mechanical allodynia after contusive spinal cord injury. *Brain Res.*, 893:59-69 (2001).
Elbashir et al., Duplexes of 21-nucleotide RNAs mediate RNA interference in cultured mammalian cells. *Nature*, 411:494-498 (2001).
Fairbanks et al., Agmatine reverse pain induced by inflammation, neuropathy, and spinal cord injury. *Proc. Natl. Acad. Sci. (USA)*, 97:10584-9 (2000).
Fire et al., Potent and specific genetic interference by double-stranded RNA in *Caenorhabditis elegans*. *Nature*, 391:806-811 (1998).

(Continued)

*Primary Examiner* — Marianne P Allen
(74) *Attorney, Agent, or Firm* — Marshall, Gerstein & Borun LLP

(57) ABSTRACT

The present invention is directed to a splice variant of a human sodium channel alpha subunit and methods and compositions for making and using the same.

9 Claims, 6 Drawing Sheets

OTHER PUBLICATIONS

Gallo et al., Modulation of non-N-methyl-D-aspartate receptors in cultured cerebellar granule cells. *J. Neurochem.*, 54:1619-1625 (1990).

Genbank Accession No. AJ251507, *Homo sapiens* mRNA for type III sodium channel protein (SCN3A gene), Apr. 15, 2005.

Genbank Accession No. CAB85895, Type III sodium channel protein, Apr. 15, 2005.

Hains et al., Serotonergic neural precursor cell grafts attenuate bilateral hyperexcitability of dorsal horn neurons after spinal hemisection in rat. *Neurosci*, 116:1097-1110 (2003).

Hains et al., Temporal plasticity of dorsal horn somatosensory neurons after acute and chronic spinal cord hemisection in rat. *Brain Res.*, 970:238-241 (2003).

Hains et al., Upregulation of sodium channel Nav1.3 and functional involvement in neuronal hyperexcitability associated with central neuropathic pain after spinal cord injury. *Neurosci.*, 23(26):8881-8892 (2003).

Hannon, RNA interference. *Nature*, 418:244-251 (2002).

Hao et al., Allodynia-like effects in rat after ischaemic spinal cord injury photochemically induced by laser irradiation. *Pain*, 45:175-185 (1991).

Hulsebosch et al., Rodent model of chronic central pain after spinal cord contusion and effects of gabapentin. *J. Neurotrauma*, 17:1205-1217 (2000).

Ikeda-Yamasaki et al., Projection map of the reaction center-light harvesting 1 complex from *Rhodopseudomonas viridis* at 10 A resolution. FEBS Lett., 425:505-508 (1998).

Jap et al., 2D crystallization: From art to science. *Ultramicroscopy*, 46:45-84 (1992).

Kasai et al., Genomic structure of SCN2A and SCN3A—candidate genes for deafness at the DFNA16 locus. *Gene*, 264:113-122 (2001).

Kim et al., An experimental model for peripheral neuropathy produced by segmental spinal nerve ligation in the rat. *Pain*, 50:355-363 (1992).

Kuhlbrand, Two-dimensional crystallization of membrane proteins. *Rev. Biophys.*, 25:1-49 (1992).

Lacapere et al., Two-dimensional crystallization of Ca-ATPase by detergent removal. *Biophys. J.*, 75:1319-1329 (1998).

Lindsey et al., An analysis of changes in sensory thresholds to mild tactile and cold stimuli after experimental spinal cord injury in the ray. Neurohabil. *Neural Repair*, 14:287-3000 (2000).

Mansikka et al., Nerve injury-induced mechanical by not thermal hyperalgesia is attenuated in neurokinin-1 receptor knockout mice. *Exp. Neurol.*, 162:343-349 (2000).

McManus et al., Gene silencing in mammals by small interfering RNAs. *Nat. Rev. Genet.*, 3:737-747 (2002).

Mills et al., Strain and model differences in behavioral outcomes after spinal cord injury in rat. *J. Neurotrauma*, 18:743-756 (2001).

Montoya et al., Two-dimensional crystallization and preliminary structure analysis of light harvesting II (B800-850) complex from the purple bacterium *Rhodovulum sulfidophilum*. *J. Mol. Biol.*, 250:1-10 (1995).

Mosser, Two-dimensional crystallogenesis of transmembrane proteins. *Micron.*, 32:517-540 (2001).

Ng et al., SIFT: Predicting amino acid changes that affect protein function. Nucleic Acid Res., 31(13):3812-3814 (2003).

Oliveira et al., Binding Specificity of Sea Anemone Toxins to $Na_v$ 1.1-1.6 Sodium Channels, *J. Biol. Chem.*, 279(32):33323-33335 (2004).

Qu et al., Differential modulation of sodium channel gating and persistent sodium currents by the beta-1, beta-2, and beta-3 subunits. *Mol. Cell Neurosci.*, 18(5):70-80 (2001).

Rigaud et al., Bio-beads: An efficient strategy for two-dimensional crystallization of membrane proteins. *J. Struct. Biol.*, 118:226-235 (1997).

Rogers et al., Molecular determinants of high affinity binding of alpha-scorpion toxin and see anemone toxin in the S3-S4 extracellular loop in domain IV of the Na+ channel alpha subunit. *J. Biol. Chem.* 271:15950-62 (1996).

Scheuring et al., High-resolution AFM topographs of Rubrivivax gelatinosus light-harvesting complex LH2. *EMBO J.*, 20:3029-3035 (2001).

Tanaka et al., SNS Na+ channel expression increases in dorsal root ganglion neurons in the carrageenan inflammatory pain model. *Neuroreport*, 9(6):967-972 (1998).

Tao et al., Expression of PSD-95/SAP90 is critical for N-methyl-d-aspartate receptor-mediated thermal hyperalgesia in the spinal cord. *Neuroscience*, 98:201-206 (2000).

Thimmapaya et al., Distribution and functional characterization of human Nax1.3 splice variants. *Eur. J. Neurosci.*, 22:1-9 (2005).

Turner et al., Chronic pain associated with spinal cord injuries: A community survey. *Arch. Phys. Med. Rehabil.*, 82:501-509 (2001).

Voltage-Gated Sodium Channels, *International Union of Pharmacology*, pp. 11-15 (2002).

Walz et al., Projection structions of three photosynthetic complexes from *Rhodobactor sphaeroides*: LH2 at 6 A, LH1 and RC-LH1 at 25 A. *J. Mol. Biol.*, 282:833-845 (1998).

Waxman et al., *Brain Res. Mol. Brain Res.*, 22(1-4):275-289 (1994).

Wood et al., Voltage-gated sodium channels and pain pathways. *J. Neurobiol.*, 61(1):55-71 (2004).

Yezierski et al., The mechanosensitivity of spinal sensory neurons following intraspinal injections of quisqualic acid in the rat. *Neurosci. Lett.*, 157:115-119 (1993).

Zerangue et al., The new ER trafficking signal regulates the subunit stoichiometry of plasma membrane KATP channels. *Neuron*, 22:537-548 (1999).

FIGURE 1A

SEQ ID NO:2 AND 4-8 Human Nav1.3 protein splice variant

```
                    1                                                            50
SEQ ID NO:4         MAQALLVPPG PESFRLFTRE SLAAIEKRAA EEKAKKPKKE QDNDDENKPK
SEQ ID NO:5         MAQALLVPPG PESFRLFTRE SLAAIEKRAA EEKAKKPKKE QDNDDENKPK
SEQ ID NO:6         MAQALLVPPG PESFRLFTRE SLAAIEKRAA EEKAKKPKKE QDNDDENKPK
SEQ ID NO:2...      MAQALLVPPG PESFRLFTRE SLAAIEKRAA EEKAKKPKKE QDNDDENKPK
SEQ ID NO:7         MAQALLVPPG PESFRLFTRE SLAAIEKRAA EEKAKKPKKE QDNDDENKPK
SEQ ID NO:8         MAQALLVPPG PESFRLFTRE SLAAIEKRAA EEKAKKPKKE QDNDDENKPK 51                                                          100
SEQ ID NO:4         PNSDLEAGKN LPFIYGDIPP EMVSEPLEDL DPYYINKKTF IVMNKGKAIF
SEQ ID NO:5         PNSDLEAGKN LPFIYGDIPP EMVSEPLEDL DPYYINKKTF IVMNKGKAIF
SEQ ID NO:6         PNSDLEAGKN LPFIYGDIPP EMVSEPLEDL DPYYINKKTF IVMNKGKAIF
SEQ ID NO:2...      PNSDLEAGKN LPFIYGDIPP EMVSEPLEDL DPYYINKKTF IVMNKGKAIF
SEQ ID NO:7         PNSDLEAGKN LPFIYGDIPP EMVSEPLEDL DPYYINKKTF IVMNKGKAIF
SEQ ID NO:8         PNSDLEAGKN LPFIYGDIPP EMVSEPLEDL DPYYINKKTF IVMNKGKAIF 101                                                         150
SEQ ID NO:4         RFSATSALYI LTPLNPVRKI AIKILVHSLF SMLIMCTILT NCVFMTLSNP
SEQ ID NO:5         RFSATSALYI LTPLNPVRKI AIKILVHSLF SMLIMCTILT NCVFMTLSNP
SEQ ID NO:6         RFSATSALYI LTPLNPVRKI AIKILVHSLF SMLIMCTILT NCVFMTLSNP
SEQ ID NO:2...      RFSATSALYI LTPLNPVRKI AIKILVHSLF SMLIMCTILT NCVFMTLSNP
SEQ ID NO:7...      RFSATSALYI LTPLNPVRKI AIKILVHSLF SMLIMCTILT NCVFMTLSNP
SEQ ID NO:8         RFSATSALYI LTPLNPVRKI AIKILVHSLF SMLIMCTILT NCVFMTLSNP 151                                                         200
SEQ ID NO:4         PDWTKNVEYT FTGIYTFESL IKILVRGFCL EDFTFLRDPW NWLDFSVIVM
SEQ ID NO:5         PDWTKNVEYT FTGIYTFESL IKILARGFCL EDFTFLRDPW NWLDFSVIVM
SEQ ID NO:6         PDWTKNVEYT FTGIYTFESL IKILARGFCL EDFTFLRDPW NWLDFSVIVM
SEQ ID NO:2...      PDWTKNVEYT FTGIYTFESL IKILARGFCL EDFTFLRDPW NWLDFSVIVM
SEQ ID NO:7         PDWTKNVEYT FTGIYTFESL IKILARGFCL EDFTFLRDPW NWLDFSVIVM
SEQ ID NO:8         PDWTKNVEYT FTGIYTFESL IKILARGFCL EDFTFLRDPW NWLDFSVIVM 201                                                         250
SEQ ID NO:4         AYVTEFVDLG NVSALRTFRV LRALKTISVI PGLKTIVGAL IQSVKKLSDV
SEQ ID NO:5         AYVTEFVSLG NVSALRTFRV LRALKTISVI PGLKTIVGAL IQSVKKLSDV
SEQ ID NO:6         AYVTEFVDLG NVSALRTFRV LRALKTISVI PGLKTIVGAL IQSVKKLSDV
SEQ ID NO:2...      AYVTEFVDLG NVSALRTFRV LRALKTISVI PGLKTIVGAL IQSVKKLSDV
SEQ ID NO:7         AYVTEFVSLG NVSALRTFRV LRALKTISVI PGLKTIVGAL IQSVKKLSDV
SEQ ID NO:8         AYVTEFVDLG NVSALRTFRV LRALKTISVI PGLKTIVGAL IQSVKKLSDV 251                                                         300
SEQ ID NO:4         MILTVFCLSV FALIGLQLFM GNLRNKCLQW PPSDSAFETN TTSYFNGTMD
SEQ ID NO:5         MILTVFCLSV FALIGLQLFM GNLRNKCLQW PPSDSAFETN TTSYFNGTMD
SEQ ID NO:6         MILTVFCLSV FALIGLQLFM GNLRNKCLQW PPSDSAFETN TTSYFNGTMD
SEQ ID NO:2...      MILTVFCLSV FALIGLQLFM GNLRNKCLQW PPSDSAFETN TTSYFNGTMD
SEQ ID NO:7         MILTVFCLSV FALIGLQLFM GNLRNKCLQW PPSDSAFETN TTSYFNGTMD
SEQ ID NO:8         MILTVFCLSV FALIGLQLFM GNLRNKCLQW PPSDSAFETN TTSYFNGTMD 301                                                         350
SEQ ID NO:4         SNGTFVNVTM STFNWKDNIG DDSHFYVLDG QKDPLLCGNG SDAGQCPEGY
SEQ ID NO:5         SNGTFVNVTM STFNWKDYIG DDSHFYVLDG QKDPLLCGNG SDAGQCPEGY
SEQ ID NO:6         SNGTFVNVTM STFNWKDYIG DDSHFYVLDG QKDPLLCGNG SDAGQCPEGY
```

FIGURE 1B

```
SEQ ID NO:2...   SNGTFVNVTM  STFNWKDYIG  DDSHFYVLDG  QKDPLLCGNG  SDAGQCPEGY
SEQ ID NO:7      SNGTFVNVTM  STFNWKDYIG  DDSHFYVLDG  QKDPLLCGNG  SDAGQCPEGY
SEQ ID NO:8      SNGTFVNVTM  STFNWKDYIG  DDSHFYVLDG  QKDPLLCGNG  SDAGQCPEGY 351                                                    400
SEQ ID NO:4      ICVKAGRNPN  YGYTSFDTFS  WAFLSLFRLM  TQDYWENLYQ  LTLRAAGKTY
SEQ ID NO:5      ICVKAGRNPN  YGYTSFDTFS  WAFLSLFRLM  TQDYWENLYQ  LTLRAAGKTY
SEQ ID NO:6      ICVKAGRNPN  YGYTSFDTFS  WAFLSLFRLM  TQDYWENLYQ  LTLRAAGKTY
SEQ ID NO:2...   ICVKAGRNPN  YGYTSFDTFS  WAFLSLFRLM  TQDYWENLYQ  LTLRAAGKTY
SEQ ID NO:7      ICVKAGRNPN  YGYTSFDTFS  WAFLSLFRLM  TQDYWENLYQ  LTLRAAGKTY
SEQ ID NO:8      ICVKAGRNPN  YGYTSFDTFS  WAFLSLFRLM  TQDYWENLYQ  LTLRAAGKTY 401                                                    450
SEQ ID NO:4      TIFFVLVIFL  GSFYLVNLIL  AVVAMAYEEQ  NQATLEEAEQ  KEAEFQQMLE
SEQ ID NO:5      MIFFVLVIFL  GSFYLVNLIL  AVVAMAYEEQ  NQATLEEAEQ  KEAEFQQMLE
SEQ ID NO:6      MIFFVLVIFL  GSFYLVNLIL  AVVAMAYEEQ  NQATLEEAEQ  KEAEFQQMLE
SEQ ID NO:2...   MIFFVLVIFL  GSFYLVNLIL  AVVAMAYEEQ  NQATLEEAEQ  KEAEFQQMLE
SEQ ID NO:7      MIFFVLVIFL  GSFYLVNLIL  AVVAMAYEEQ  NQATLEEAEQ  KEAEFQQMLE
SEQ ID NO:8      MIFFVLVIFL  GSFYLVNLIL  AVVAMAYEEQ  NQATLEEAEQ  KEAEFQQMLE 451                                                    500
SEQ ID NO:4      QLKKQQEEAQ  AVAAASAASR  DFSGIGGLGE  LLESSSEASK  LSSKSAKEWR
SEQ ID NO:5      QLKKQQEEAQ  AVAAASAASR  DFSGIGGLGE  LLESSSEASK  LSSKSAKEWR
SEQ ID NO:6      QLKKQQEEAQ  AVAAASAASR  DFSGVGGLGE  LLESSSEASK  LSSKGAKEWR
SEQ ID NO:2...   QLKKQQEEAQ  AVAAASAASR  DFSGIGGLGE  LLESSSEASK  LSSKSAKEWR
SEQ ID NO:7      QLKKQQEEAQ  AVAAASAASR  DFSGIGGLGE  LLESSSEASK  LSSKSAKEWR
SEQ ID NO:8      QLKKQQEEAQ  AVAAASAASR  DFSGVGGLGE  LLESSSEASK  LSSKGAKEWR 501                                                    550
SEQ ID NO:4      NRRKKRRQRE  HLEGNNKGER  DSFPKSESED  SVKRSSFLFS  MDGNRLTSDK
SEQ ID NO:5      NRRKKRRQRE  HLEGNNKGER  DSFPKSESED  SVKRSSFLFS  MDGNRLTSDK
SEQ ID NO:6      NRRKKRRQRE  HLEGNNKGER  DSFPKSESED  SVKRSSFLFS  MDGNRLTSDK
SEQ ID NO:2...   NRRKKRRQRE  HLEGNNKGER  DSFPKSESED  SVKRSSFLFS  MDGNRLTSDK
SEQ ID NO:7      NRRKKRRQRE  HLEGNNKGER  DSFPKSESED  SVKRSSFLFS  MDGNRLTSDK
SEQ ID NO:8      NRRKKRRQRE  HLEGNNKGER  DSFPKSESED  SVKRSSFLFS  MDGNRLTSDK 551                                                    600
SEQ ID NO:4      KFCSPHQSLL  SIRGSLFSPR  RNSKTSIFSF  RGRAKDVGSE  NDFADDEHST
SEQ ID NO:5      KFCSPHQSLL  SIRGSLFSPR  RNSKTSIFSF  RGRAKDVGSE  NDFADDEHST
SEQ ID NO:6      KFCSPHQSLL  SIRGSLFSPR  RNSKTSIFSF  RGRAKDVGSE  NDFADDEHST
SEQ ID NO:2...   KFCSPHQSLL  SIRGSLFSPR  RNSKTSIFSF  RGRAKDVGSE  NDFADDEHST
SEQ ID NO:7      KFCSPHQSLL  SIRGSLFSPR  RNSKTSIFSF  RGRAKDVGSE  NDFADDEHST
SEQ ID NO:8      KFCSPHQSLL  SIRGSLFSPR  RNSKTSIFSF  RGRAKDVGSE  NDFADDEHST 601                                                    650
SEQ ID NO:4      FEDSETRRDS  LFEPHRHGER  RNS.......  ..........  ..........
SEQ ID NO:5      FEDSESRRDS  LFVPHRHGER  RNS.......  ..........  ..........
SEQ ID NO:6      FEDGESRRDS  LFVPHRHGER  RNSNVSQASM  SSRMVPGLPA  NGKMHSTVDC
SEQ ID NO:2...   FEDSESRRDS  LFVPHRHGER  RNSNVSQASM  SSRMVPGLPA  NGKMHSTVDC
SEQ ID NO:7      FEDSESRRDS  LFVPHRHGER  RNS.......  ..........  ..........
SEQ ID NO:8      FEDSESRRDS  LFVPHRHGER  RNS.......  ..........  N.....G...

651                                                    700
SEQ ID NO:4      ..........  ..........  ..NGTTTETE  VRKRRLSSYQ  ISMEMLEDSS
SEQ ID NO:5      ..........  ..........  ..NGTTTETE  VRKRRLSSYQ  ISMEMLEDSS
```

FIGURE 1C

```
SEQ ID NO:6    NGVVSLVGGP  SALTSPTGQL  PPEGTTTETE  VRKRRLSSYQ  ISMEMLEDSS
SEQ ID NO:2... NGVVSL....  ..........  ...GTTTETE  VRKRRLSSYQ  ISMEMLEDSS
SEQ ID NO:7    ..........  ..........  ..NGTTTETE  VRKRRLSSYQ  ISMEMLEDSS
SEQ ID NO:8    ..........  ..........  ....TTTETE  VRKRRLSSYQ  ISMEMLEDSS 701                                                    750
SEQ ID NO:4    GRQRAVSIAS  ILTNTMEELE  ESRQKCPPCW  YRFANVFLIW  DCCDAWLKVK
SEQ ID NO:5    GRQRAVSIAS  ILTNTMEELE  ESRQKCPPCW  YRFANVFLIW  DCCDAWLKVK
SEQ ID NO:6    GRQRAVSIAS  ILTNTMEELE  ESRQKCPPCW  YRFANVFLIW  DCCDAWLKVK
SEQ ID NO:2... GRQRAVSIAS  ILTNTMEELE  ESRQKCPPCW  YRFANVFLIW  DCCDAWLKVK
SEQ ID NO:7    GRQRAVSIAS  ILTNTMEELE  ESRQKCPPCW  YRFANVFLIW  DCCDAWLKVK
SEQ ID NO:8    GRQRAVSIAS  ILTNTMEELE  ESRQKCPPCW  YRFANVFLIW  DCCDAWLKVK 751                                                    800
SEQ ID NO:4    HLVNLIVMDP  FVDLAITICI  VLNTLFMAME  HYPMTEQFSS  VLTVGNLVFT
SEQ ID NO:5    HLVNLIVMDP  FVDLAITICI  VLNTLFMAME  HYPMTEQFSS  VLTVGNLVFT
SEQ ID NO:6    HLVNLIVMDP  FVDLAITICI  VLNTLFMAME  HYPMTEQFSS  VLTVGNLVFT
SEQ ID NO:2... HLVNLIVMDP  FVDLAITICI  VLNTLFMAME  HYPMTEQFSS  VLTVGNLVFT
SEQ ID NO:7    HLVNLIVMDP  FVDLAITICI  VLNTLFMAME  HYPMTEQFSS  VLTVGNLVFT
SEQ ID NO:8    HLVNLIVMDP  FVDLAITICI  VLNTLFMAME  HYPMTEQFSS  VLTVGNLVFT 801                                                    850
SEQ ID NO:4    GIFTAEMVLK  IIAMDPYYYF  QEGWNIFDGI  IVSLSLMELG  LSNVEGLSVL
SEQ ID NO:5    GIFTAEMVLK  IIAMDPYYYF  QEGWNIFDGI  IVSLSLMELG  LSNVEGLSVL
SEQ ID NO:6    GIFTAEMVLK  IIAMDPYYYF  QEGWNIFDGI  IVSLSLMELG  LSNVEGLSVL
SEQ ID NO:2... GIFTAEMVLK  IIAMDPYYYF  QEGWNIFDGI  IVSLSLMELG  LSNVEGLSVL
SEQ ID NO:7    GIFTAEMVLK  IIAMDPYYYF  QEGWNIFDGI  IVSLSLMELG  LSNVEGLSVL
SEQ ID NO:8    GIFTAEMVLK  IIAMDPYYYF  QEGWNIFDGI  IVSLSLMELG  LSNVEGLSVL 851                                                    900
SEQ ID NO:4    RSFRLLRVFK  LAKSWPTLNM  LIKIIGNSVG  ALGNLTLVLA  IIVFIFAVVG
SEQ ID NO:5    RSFRLLRVFK  LAKSWPTLNM  LIKIIGNSVG  ALGNLTLVLA  IIVFIFAVVG
SEQ ID NO:6    RSFRLLRVFK  LAKSWPTLNM  LIKIIGNSVG  ALGNLTLVLA  IIVFIFAVVG
SEQ ID NO:2... RSFRLLRVFK  LAKSWPTLNM  LIKIIGNSVG  ALGNLTLVLA  IIVFIFAVVG
SEQ ID NO:7    RSFRLLRVFK  LAKSWPTLNM  LIKIIGNSVG  ALGNLTLVLA  IIVFIFAVVG
SEQ ID NO:8    RSFRLLRVFK  LAKSWPTLNM  LIKIIGNSVG  ALGNLTLVLA  IIVFIFAVVG 901                                                    950
SEQ ID NO:4    MQLFGKSYKE  CVCKINDDCT  LPRWHMNDFF  HSFLIVFRVL  CGEWIETMWD
SEQ ID NO:5    MQLFGKSYKE  CVCKINDDCT  LPRWHMNDFF  HSFLIVFRVL  CGEWIETMWD
SEQ ID NO:6    MQLFGKSYKE  CVCKINDDCT  LPRWHMNDFF  HSFLIVFRVL  CGEWIETMWD
SEQ ID NO:2... MQLFGKSYKE  CVCKINDDCT  LPRWHMNDFF  HSFLIVFRVL  CGEWIETMWD
SEQ ID NO:7    MQLFGKSYKE  CVCKINDDCT  LPRWHMNDFF  HSFLIVFRVL  CGEWIETMWD
SEQ ID NO:8    MQLFGKSYKE  CVCKINDDCT  LPRWHMNDFF  HSFLIVFRVL  CGEWIETMWD 951                                                    1000
SEQ ID NO:4    CMEVAGQTMC  LIVFMLVMVI  GNLVVLNLFL  ALLLSSFSSD  NLAATDDDNE
SEQ ID NO:5    CMEVAGQTMC  LIVFMLVMVI  GNLVVLNLFL  ALLLSSFSSD  NLAATDDDNE
SEQ ID NO:6    CMEVAGQTMC  LIVFMLVMVI  GNLVVLNLFL  ALLLSSFSSD  NLAATDDDNE
SEQ ID NO:2... CMEVAGQTMC  LIVFMLVMVI  GNLVVLNLFL  ALLLSSFSSD  NLAATDDDNE
SEQ ID NO:7    CMEVAGQTMC  LIVFMLVMVI  GNLVVLNLFL  ALLLSSFSSD  NLAATDDDNE
SEQ ID NO:8    CMEVAGQTMC  LIVFMLVMVI  GNLVVLNLFL  ALLLSSFSSD  NLAATDDDNE 1001                                                   1050
SEQ ID NO:4    MNNLQIAVGR  MQKGIDYVKN  KMRECFQKAF  FRKPKVIEIH  EGNKIDSCMS
```

FIGURE 1D

```
SEQ ID NO:5    MNNLQIAVGR MQKGIDYVKN KMRECFQKAF FRKPKVIEIH EGNKIDSCMS
SEQ ID NO:6    MNNLQIAVGR MQKGIDYVKN KMRECFQKAF FRKPKVIEIH EGNKIDSCMS
SEQ ID NO:2... MNNLQIAVGR MQKGIDYVKN KMRECFQKAF FRKPKVIEIH EGNKIDSCMS
SEQ ID NO:7    MNNLQIAVGR MQKGIDYVKN KMRECFQKAF FRKPKVIEIH EGNKIDSCMS
SEQ ID NO:8    MNNLQIAVGR MQKGIDYVKN KMRECFQKAF FRKPKVIEIH EGNKIDSCMS 1051                                                1100
SEQ ID NO:4    NNTGIEISKA LNYLRDGNGT TSGVGTGSSV EKYVIDENDY MSFINNPSLT
SEQ ID NO:5    NNTGIEISKE LNYLRDGNGT TSGVGTGSSV EKYVIDENDY MSFINNPSLT
SEQ ID NO:6    NNTGIEISKE LNYLRDGNGT TSGVGTGSSV EKYVIDENDY MSFINNPSLT
SEQ ID NO:2... NNTGIEISKE LNYLRDGNGT TSGVGTGSSV EKYVIDENDY MSFINNPSLT
SEQ ID NO:7    NNTGIEISKE LNYLRDGNGT TSGVGTGSSV EKYVIDENDY MSFINNPSLT
SEQ ID NO:8    NNTGIEISKE LNYLRDGNGT TSGVGTGSSV EKYVIDENDY MSFINNPSLT 1101                                                1150
SEQ ID NO:4    VTVPIAVGES DFENLNTEEF SSESELEESK EKLNATSSSE GSTVDVVLPR
SEQ ID NO:5    VTVPIAVGES DFENLNTEEF SSESELEESK EKLNATSSSE GSTVDVVLPR
SEQ ID NO:6    VTVPIAVGES DFENLNTEEF SSESELEESK EKLNATSSSE GSTVDVVLPR
SEQ ID NO:2... VTVPIAVGES DFENLNTEEF SSESELEESK EKLNATSSSE GSTVDVVLPR
SEQ ID NO:7    VTVPIAVGES DFENLNTEEF SSESELEESK EKLNATSSSE GSTVDVVLPR
SEQ ID NO:8    VTVPIAVGES DFENLNTEEF SSESELEESK EKLNATSSSE GSTVDVVLPR 1151                                                1200
SEQ ID NO:4    EGEQAETEPE EDLKPEACFT EGCIKKFPFC QVSTEEGKGK IWWNLRKTCY
SEQ ID NO:5    EGEQAETEPE EDLKPEACFT EGCIKKFPFC QVSTEEGKGK IWWNLRKTCY
SEQ ID NO:6    EGEQAETEPE EDFKPEACFT EGCIKKFPFC QVSTEEGKGK IWWNLRKTCY
SEQ ID NO:2... EGEQAETEPE EDLKPEACFT EGCIKKFPFC QVSTEEGKGK IWWNLRKTCY
SEQ ID NO:7    EGEQAETEPE EDLKPEACFT EGCIKKFPFC QVSTEEGKGK IWWNLRKTCY
SEQ ID NO:8    EGEQAETEPE EDFKPEACFT EGCIKKFPFC QVSTEEGKGK IWWNLRKTCY 1201                                                1250
SEQ ID NO:4    SIVEHNWFET FIVFMILLSS GALAFEDIYI EQRKTIKTML EYADKVFTYI
SEQ ID NO:5    SIVEHNWFET FIVFMILLSS GALAFEDIYI EQRKTIKTML EYADKVFTYI
SEQ ID NO:6    SIVEHNWFET FIVFMILLSS GALAFEDIYI EQRKTIKTML EYADKVFTYI
SEQ ID NO:2... SIVEHNWFET FIVFMILLSS GALAFEDIYI EQRKTIKTML EYADKVFTYI
SEQ ID NO:7    SIVEHNWFET FIVFMILLSS GALAFEDIYI EQRKTIKTML EYADKVFTYI
SEQ ID NO:8    SIVEHNWFET FIVFMILLSS GALAFEDIYI EQRKTIKTML EYADKVFTYI 1251                                                1300
SEQ ID NO:4    FILEMLLKWV AYGFQTYFTN AWCRLDFLIV DVSLVSLVAN ALGYSELGAI
SEQ ID NO:5    FILEMLLKWV AYGFQTYFTN AWCWLDFLIV DVSLVSLVAN ALGYSELGAI
SEQ ID NO:6    FILEMLLKWV AYGFQTYFTN AWCWLDFLIV DVSLVSLVAN ALGYSELGAI
SEQ ID NO:2... FILEMLLKWV AYGFQTYFTN AWCWLDFLIV DVSLVSLVAN ALGYSELGAI
SEQ ID NO:7    FILEMLLKWV AYGFQTYFTN AWCWLDFLIV DVSLVSLVAN ALGYSELGAI
SEQ ID NO:8    FILEMLLKWV AYGFQTYFTN AWCWLDFLIV DVSLVSLVAN ALGYSELGAI 1301                                                1350
SEQ ID NO:4    KSLRTLRALR PLRALSRFEG MRVVVNALVG AIPSIMNVLL VCLIFWLIFS
SEQ ID NO:5    KSLRTLRALR PLRALSRFEG MRVVVNALVG AIPSIMNVLL VCLIFWLIFS
SEQ ID NO:6    KSLRTLRALR PLRALSRFEG MRVVVNALVG AIPSIMNVLL VCLIFWLIFS
SEQ ID NO:2... KSLRTLRALR PLRALSRFEG MRVVVNALVG AIPSIMNVLL VCLIFWLIFS
SEQ ID NO:7    KSLRTLRALR PLRALSRFEG MRVVVNALVG AIPSIMNVLL VCLIFWLIFS
SEQ ID NO:8    KSLRTLRALR PLRALSRFEG MRVVVNALVG AIPSIMNVLL VCLIFWLIFS 1351                                                1400
```

FIGURE 1E

```
            1351                                                    1400
SEQ ID NO:4  IMGVNLFAGK FYHCVNMTTG NMFDISDVNN LSDCQALGKQ ARWKNVKVNF
SEQ ID NO:5  IMGVNLFAGK FYHCVNMTTG NMFDISDVNN LSDCQALGKQ ARWKNVKVNF
SEQ ID NO:6  IMGVNLFAGK FYHCVNMTTG NMFDISDVNN LSDCQALGKQ ARWKNVKVNF
SEQ ID NO:2..IMGVNLFAGK FYHCVNMTTG NMFDISDVNN LSDCQALGKQ ARWKNVKVNF
SEQ ID NO:7  IMGVNLFAGK FYHCVNMTTG NMFDISDVNN LSDCQALGKQ ARWKNVKVNF
SEQ ID NO:8  IMGVNLFAGK FYHCVNMTTG NMFDISDVNN LSDCQALGKQ ARWKNVKVNF 1401                                                    1450
SEQ ID NO:4  DNVGAGYLAL LQVVS..... .......... .......... ..........
SEQ ID NO:5  DNVGAGYLAL LQVATFKGWM DIMYAAVDSR DVKLQPVYEE NLYMYLYFVI
SEQ ID NO:6  DNVGAGYLAL LQVATFKGWM DIMYAAVDSR DVKLQPVYEE NLYMYLYFVI
SEQ ID NO:2..DNVGAGYLAL LQVATFKGWM DIMYAAVDSR DVKLQPVYEE NLYMYLYFVI
SEQ ID NO:7  DNVGAGYLAL LQVATFKGWM DIMYAAVDSR DVKLQPVYEE NLYMYLYFVI
SEQ ID NO:8  DNVGAGYLAL LQVATFKGWM DIMYAAVDSR DVKLQPVYEE NLYMYLYFVI 1451                                                    1500
SEQ ID NO:4  .......... .......... .......... .......... ..........
SEQ ID NO:5  FIIFGSFFTL NLFIGVIIDN FNQQKKKFGG QDIFMTEEQK KYYNAMKKLG
SEQ ID NO:6  FIIFGSFFTL NLFIGVIIDN FNQQKKKFGG QDIFMTEEQK KYYNAMKKLG
SEQ ID NO:2..FIIFGSFFTL NLFIGVIIDN FNQQKKKFGG QDIFMTEEQK KYYNAMKKLG
SEQ ID NO:7  FIIFGSFFTL NLFIGVIIDN FNQQKKKFGG QDIFMTEEQK KYYNAMKKLG
SEQ ID NO:8  FIIFGSFFTL NLFIGVIIDN FNQQKKKFGG QDIFMTEEQK KYYNAMKKLG 1501                                                    1550
SEQ ID NO:4  .......... .......... .......... .......... ..........
SEQ ID NO:5  SKKPQKPIPR PANKFQGMVF DFVTRQVFDI SIMILICLNM VTMMVETDDQ
SEQ ID NO:6  SKKPQKPIPR PANKFQGMVF DFVTRQVFDI SIMILICLNM VTMMVETDDQ
SEQ ID NO:2..SKKPQKPIPR PANKFQGMVF DFVTRQVFDI SIMILICLNM VTMMVETDDQ
SEQ ID NO:7  SKKPQKPIPR PANKFQGMVF DFVTRQVFDI SIMILICLNM VTMMVETDDQ
SEQ ID NO:8  SKKPQKPIPR PANKFQGMVF DFVTRQVFDI SIMILICLNM VTMMVETDDQ 1551                                                    1600
SEQ ID NO:4  .......... .......... .......... .......... ..........
SEQ ID NO:5  GKYMTLVLSR INLVFIVLFT GEFVLKLVSL RHYYFTIGWN IFDFVVVILS
SEQ ID NO:6  GKYMTLVLSR INLVFIVLFT GEFVLKLVSL RHYYFTIGWN IFDFVVVILS
SEQ ID NO:2..GKYMTLVLSR INLVFIVLFT GEFVLKLVSL RHYYFTIGWN IFDFVVVILS
SEQ ID NO:7  GKYMTLVLSR INLVFIVLFT GEFVLKLVSL RHYYFTIGWN IFDFVVVILS
SEQ ID NO:8  GKYMTLVLSR INLVFIVLFT GEFVLKLVSL RHYYFTIGWN IFDFVVVILS 1601                                                    1650
SEQ ID NO:4  .......... .......... .......... .......... ..........
SEQ ID NO:5  IVGMFLAEMI EKYFVSPTLF RVIRLARIGR ILRLIKGAKG IRTLLFALMM
SEQ ID NO:6  IVGMFLAEMI EKYSVSPTLF RVIRLARIGR ILRLIKGAKG IRTLLFALMM
SEQ ID NO:2..IVGMFLAEMI EKYFVSPTLF RVIRLARIGR ILRLIKGAKG IRTLLFALMM
SEQ ID NO:7  IVGMFLAEMI EKYFVSPTLF RVIRLARIGR ILRLIKGAKG IRTLLFALMM
SEQ ID NO:8  IVGMFLAEMI EKYSVSPTLF RVIRLARIGR ILRLIKGAKG IRTLLFALMM 1651                                                    1700
SEQ ID NO:4  .......... .......... .......... .......... ..........
SEQ ID NO:5  SLPALFNIGL LLFLVMFIYA IFGMSNFAYV KKEAGIDDMF NFETFGNSMI
SEQ ID NO:6  SLPALFNIGL LLFLVMFIYA IFGMSNFAYV KKEAGIDDMF NFETFGNSMI
SEQ ID NO:2..SLPALFNIGL LLFLVMFIYA IFGMSNFAYV KKEAGIDDMF NFETFGNSMI
SEQ ID NO:7  SLPALFNIGL LLFLVMFIYA IFGMSNFAYV KKEAGIDDMF NFETFGNSMI
SEQ ID NO:8  SLPALFNIGL LLFLVMFIYA IFGMSNFAYV KKEAGIDDMF NFETFGNSMI
```

FIGURE 1F

```
              1701                                                    1750
SEQ ID NO:4   ..........  ..........  ..........  ..........  ..........
SEQ ID NO:5   CLFQITTSAG  WDGLLAPILN  SAPPDCDPDT  IHPGSSVKGD  CGNPSVGIFF
SEQ ID NO:6   CLFQITTSAG  WDGLLAPILN  SAPPDCDPDT  IHPGSSVKGD  RGDPSVGIFF
SEQ ID NO:2...CLFQITTSAG  WDGLLAPILN  SAPPDCDPDT  IHPGSSVKGD  CGNPSVGIFF
SEQ ID NO:7   CLFQITTSAG  WDGLLAPILN  SAPPDCDPDT  IHPGSSVKGD  CGNPSVGIFF
SEQ ID NO:8   CLFQITTSAG  WDGLLAPILN  SAPPDCDPDT  IHPGSSVKGD  RGDPSVGIFF 1751                                                    1800
SEQ ID NO:4   ..........  ..........  ..........  ..........  ..........
SEQ ID NO:5   FVSYIIISFL  VVVNMYIAVI  LENFSVATEE  SAEPLSEDDF  EMFYEVWEKF
SEQ ID NO:6   FVSYIIISFL  VVVNMYIAVI  LENFSVATEE  SAEPLSEDDF  EMFYEVWEKF
SEQ ID NO:2...FVSYIIISFL  VVVNMYIAVI  LENFSVATEE  SAEPLSEDDF  EMFYEVWEKF
SEQ ID NO:7   FVSYIIISFL  VVVNMYIAVI  LENFSVATEE  SAEPLSEDDF  EMFYEVWEKF
SEQ ID NO:8   FVSYIIISFL  VVVNMYIAVI  LENFSVATEE  SAEPLSEDDF  EMFYEVWEKF 1801                                                    1850
SEQ ID NO:4   ..........  ..........  ..........  ..........  ..........
SEQ ID NO:5   DPDATQFIEF  SKLSDFAAAL  DPPLLIAKPN  KVQLIAMDLP  MVSGDRIHCL
SEQ ID NO:6   DPDATQFIEF  SKLSDFAAAL  DPPLLIAKPN  KVQLIAMDLP  MVSGDRIHCL
SEQ ID NO:2...DPDATQFIEF  SKLSDFAAAL  DPPLLIAKPN  KVQLIAMDLP  MVSGDRIHCL
SEQ ID NO:7   DPDATQFIEF  SKLSDFAAAL  DPPLLIAKPN  KVQLIAMDLP  MVSGDRIHCL
SEQ ID NO:8   DPDATQFIEF  SKLSDFAAAL  DPPLLIAKPN  KVQLIAMDLP  MVSGDRIHCL 1851                                                    1900
SEQ ID NO:4   ..........  ..........  ..........  ..........  ..........
SEQ ID NO:5   DILFAFTKRV  LGESGEMDAL  RIQMEDRFMA  SNPSKVSYEP  ITTTLKRKQE
SEQ ID NO:6   DILFAFTKRV  LCESGEMDAL  RIQMEDRFMA  SNPSKVSYEP  ITTTLKRKQE
SEQ ID NO:2...DILFAFTKRV  LGESGEMDAL  RIQMEDRFMA  SNPSKVSYEP  ITTTLKRKQE
SEQ ID NO:7   DILFAFTKRV  LGESGEMDAL  RIQMEDRFMA  SNPSKVSYEP  ITTTLKRKQE
SEQ ID NO:8   DILFAFTKRV  LCESGEMDAL  RIQMEDRFMA  SNPSKVSYEP  ITTTLKRKQE 1901                                                    1950
SEQ ID NO:4   ..........  ..........  ..........  ..........  ..........
SEQ ID NO:5   EVSAAIIQRN  FRCYLLKQRL  KNISSNYNKE  AIKGRIDLPI  KQDMIIDKLN
SEQ ID NO:6   EVSAAIIQRN  FRCYLLKQRL  KNISSNYNKE  AIKGRIDLPI  KQDMIIDKLN
SEQ ID NO:2...EVSAAIIQRN  FRCYLLKQRL  KNISSNYNKE  AIKGRIDLPI  KQDMIIDKLN
SEQ ID NO:7   EVSAAIIQRN  FRCYLLKQRL  KNISSNYNKE  AIKGRIDLPI  KQDMIIDKLN
SEQ ID NO:8   EVSAAIIQRN  FRCYLLKQRL  KNISSNYNKE  AIKGRIDLPI  KQDMIIDKLN 1951                                                    2000
SEQ ID NO:4   ..........  ..........  ..........  ..........  ..........
SEQ ID NO:5   GNSTPEKTDG  SSSTTSPPSY  DSVTKPDKEK  FEKDKPEKES  KGKEVRENQK
SEQ ID NO:6   GNSTPEKTDG  SSSTTPPPSY  DSVTKPDKEK  FEKDKPEKES  KGKEVRENQK
SEQ ID NO:2...GNSTPEKTDG  SSSTTSPPSY  DSVTKPDKEK  FEKDKPEKES  KGKEVRENQK
SEQ ID NO:7   GNSTPEKTDG  SSSTTSPPSY  DSVTKPDKEK  FEKDKPEKES  KGKEVRENQK
SEQ ID NO:8   GNSTPEKTDG  SSSTTSPPSY  DSVTKPDKEK  FEKDKPEKES  KGKEVRENQK
```

SODIUM CHANNEL PROTEIN TYPE III α-SUBUNIT SPLICE VARIANT

This application is a divisional of U.S. patent application Ser. No. 12/416,777 (issued as U.S. Pat. No. 7,915,385), filed Apr. 1, 2009, which is a divisional of U.S. patent application Ser. No. 11/357,518 (issued as U.S. Pat. No. 7,531,523), filed Feb. 17, 2006, which claims the benefit of priority of U.S. Provisional Application No. 60/654,019, filed Feb. 17, 2005, which is incorporated herein by reference in its entirety.

BACKGROUND

1. Field of the Invention

The present invention is generally directed to voltage-gated sodium channel $Na_V1.3$ splice variants. The invention further describes methods and compositions for the stable expression of such splice variants and methods of use of such compositions for identifying compounds that modulate the activity of sodium channels.

2. Background of the Related Art

The electrical activity of neuronal and muscle cells are governed by the activity of sodium channels on the plasma membrane of such cells. Rapid entry of sodium ions into the cell through such a channel causes depolarization of the membrane and generation of an action potential. Entry of sodium ions through sodium channels in response to a voltage change on the plasma membrane in excitable cells plays a functional role in the excitation of neurons in the central nervous system and the peripheral nervous system.

Sodium channels are voltage-gated transmembrane proteins that form ion channels within the membrane and have been the target of significant pharmocologic study, due to their potential role in a variety of pathological conditions. These sodium channels are responsible for the cellular uptake of sodium during the transmission of an electrical signal in cell membranes. The channels are members of a multigene family of proteins and are typically composed of a number of subunits. Typically, the pore of the channel is formed by the α-subunit and there are four accessory β-subunits, termed β1, β2, β3 and β3.

The β-subunits are involved in the modulation of the activity of sodium channel but the α-subunit is all that is required for the channel to form a functional ion pore. Co-expression of the β-subunits with the α-subunit has been shown to produce a more positive membrane potential. Further not all of the β-subunits are required, for example, it has been shown that the β3-subunits alone is sufficient to cause an increase in sodium current (Qu et al., Mol. Cell. Neurosci., 18(5):570-80, 2001).

The amino acid sequence of the sodium channel has been evolutionarily conserved. The channel is comprised of a signal polypeptide containing four internal repeats (domains I-IV). Each domain folds into six transmembrane α-helices or segments, of which five are hydrophobic and one is a highly-charged domain containing lysine and arginine residues (S4 segment). The highly-charged S4 segment is involved in the voltage gating properties of the sodium channel. The positively-charged side chains of the amino acids of the S4 segment are thought to be paired with the negatively-charged side chains of the other five segments such that upon membrane depolarization there is a shift in the position of one of the helices relative to the other resulting in an opening of the channel.

There are numerous variants of sodium channel α-subunit. These variants may be classified according to their sensitivity to tetrodotoxin (TTX). Those subunits that are inhibited by nanomolar quantities of TTX are classified as tetrodotoxin-sensitive channels, whereas those that require at least micromolar quantities of TTX for inhibition are referred to as tetrodotoxin-insensitive (1-5 micromolar). Those channels that require greater that 100 micromolar quantities of the TTX are termed tetrodotoxin-resistant. TTX is a toxin that blocks the conduction of nerve impulses along the axons and leads to paralysis. It binds to sodium channels and blocks the flow of sodium ions. It is believed that the positively-charged group of the toxin interacts with a negatively-charged carboxylate at the mouth of the channel on the extracellular side of the membrane thereby blocking the conductance of the pathway.

It has been noted that following nerve injury there is hyperexcitability (or an increased rate of spontaneous impulse firing in neurons) in peripheral sensory ganglia. It has been suggested that this hyperexcitability in neurons is due to altered sodium channel expression in some chronic pain syndromes (Tanaka et al., Neuroreport 1998; 9 (6): 967-72). Increased numbers of sodium channels leading to inappropriate, repetitive firing of the neurons have been reported in the tips of injured axons in various peripheral nervous tissues such as the DRG, which relay signals from the peripheral receptors to the central nervous system. Indeed, it has been noted that there is an increase in expression of an α1 $Na_V1.3$ subunit in axotomized DRG neurons together with elevated levels of α1 $Na_V1.1$ and α1 $Na_V1.2$ mRNAs (Waxman et al, Brain Res Mol Brain Res 1994; 22 (1-4): 275-89).

The peripheral input that drives pain perception is thought to depend upon the presence of functional voltage-gated sodium channels in peripheral nerves. It has been noted that there is a positive correlation between increased sodium channel expression in peripheral nerves. Some studies have also shown increased expression in association with neuropathic pain. In particular, it has been recognized that acute, inflammatory, and neuropathic pain can all be attenuated or abolished by local treatment with sodium channel blockers such as lidocaine. Remarkably, two voltage-gated sodium channel genes (Nav1.8 and Nav1.9) are expressed selectively in damage-sensing peripheral neurons, while a third channel (Nav1.7) is found predominantly in sensory and sympathetic neurons. An embryonic channel (Nav1.3) is also upregulated in damaged peripheral nerves and associated with increased electrical excitability in neuropathic pain states. Using antisense and knock-out studies, it has been shown that these sodium channels play a specialized role in pain pathways, and pharmacological studies (Wood et al., J Neurobiol., 61(1):55-71, 2004).

Most patients with traumatic spinal cord injury (SCI) report moderate to severe chronic pain that is refractory, or only partially responsive, to standard clinical interventions (Balazy, Clin J Pain 8: 102-110, 1992; Turner et al., Arch Phys Med Rehabil 82: 501-509, 2001). Experimental contusion SCI in rodents can produce long-lasting central neuropathic pain (Hulsebosch et al., J Neurotrauma 17: 1205-1217, 2000; Lindsey et al., Neurorehabil Neural Repair 14: 287-300, 2000; Hains et al., Neuroscience 116: 1097-1110, 2001; Mills et al., J Neurotrauma 18: 743-756, 2001). In spinally injured animals, alterations in electrophysiologic properties of dorsal horn neurons (Hao et al., Pain 45: 175-185, 1991; Yezierski and Park, Neurosci Lett 157: 115-119, 1993; Drew et al., Brain Res 893: 59-69, 2001; Hains et al., Neuroscience 116: 1097-1110, 2003a; Hains et al., Brain Res 970: 238-241, 2003b) are thought to contribute to changes in somatosensory responsiveness.

The TTX-sensitive Nav1.3-سodium channel is expressed at relatively high levels in embryonic dorsal root ganglion (DRG) neurons but is barely detectable in adult DRG neurons and its expression is decreased in the adult spinal cord and CNS throughout development. However, the expression of Nav1.3 mRNA and protein is markedly upregulated in DRG neurons of adult rats after axotomy of peripheral projections, after chronic constriction injury, and after tight spinal nerve ligation. This produces a rapidly repriming TTX-S current that permits neuronal firing at higher than normal frequencies. It has been shown that an increase in expression of Nav1.3, similar to the changes in DRG neurons after peripheral axotomy, takes place in lumbar dorsal horn sensory neurons after SCI. It has further been shown that knock-down or reduction of expression of Nav1.3 mRNA and protein results in a reduction in hyperexcitability of dorsal horn sensory neurons and pain-related behaviors in animals (Hains et al., J. Neurosci., 23(26):0881-8892, 2003).

There are various sodium channels that remain to be characterized. Identification of such channels will facilitate further studies and identification and characterization of further isotype-specific antagonists of sodium channel blockers. Such sodium channel blockers or antagonists will be useful in the management of pain. Preferably, such analgesic agents are such that treatment of pain is facilitated without having deleterious side effects due to cardiac, central nervous system or neuromuscular complications.

SUMMARY OF THE INVENTION

The present invention is directed to a splice variant of a human sodium channel alpha subunit and methods and compositions for making and using the same. More specifically, one embodiment of the invention is directed to an isolated recombinant nucleic acid encoding a human sodium channel NaV1.3 polypeptide wherein the polypeptide is encoded by the nucleic acid sequence presented in SEQ ID NO: 1.

Another embodiment of the invention describes an isolated recombinant nucleic acid encoding a human sodium channel NaV1.3 recombinant protein having the amino acid sequence of SEQ ID NO: 2. Also contemplated herein is an isolated recombinant nucleic acid comprising the sequence presented in SEQ ID NO: 1, the mature protein coding portion thereof, or a complement thereof. One preferred embodiment of the invention contemplates an isolated recombinant nucleic acid encoding a polypeptide of SEQ ID NO: 2. The nucleic acids described herein may be genomic DNA, cDNA, or RNA.

Conservative variants of the sequences of the present invention are particularly contemplated, for example, the invention is directed to an isolated nucleic acid comprising a nucleotide sequence encoding a polypeptide that is a conservative variant of the amino acid sequence set forth in SEQ ID NO:2, wherein the variant encodes a sodium channel α-subunit with the proviso that residue 208 of SEQ ID NO:2 is an aspartic acid residue and an insert of 33 amino acids is found after residue 623, as defined in SEQ ID NO:2.

Expression constructs that comprise an isolated nucleic acid encoding a protein having an amino acid sequence of SEQ ID NO:2 or the mature protein portion thereof wherein the mature protein region comprises an aspartic acid residue at the residue that corresponds to amino acid residue 208 in SEQ ID NO:2, an insert of 33 amino acids is found after residue 623, as defined in SEQ ID NO:2 and a promoter operably linked to the polynucleotide also form part of the invention. In specific embodiments, the expression construct is such that the nucleic acid comprises a mature protein coding sequence as set forth in SEQ ID NO:1. The expression construct is an expression construct selected from the group consisting of an adenoassociated viral construct, an adenoviral construct, a herpes viral expression construct, a vaccinia viral expression construct, a retroviral expression construct, a lentiviral expression construct and a naked DNA expression construct.

Also part of the invention are recombinant host cell stably transformed or transfected with a nucleic acid or an expression construct of the invention in a manner that allows the expression in the host cell of a protein of SEQ ID NO:2. Preferably, the nucleic acid transforming the host cell comprises a mature protein encoding sequence as set forth in SEQ ID NO:1, wherein the mature protein encoded by the sequence is a sodium channel NaV1.3 polypeptide that has an aspartic acid residue at the amino acid that corresponds to amino acid residue 208 of SEQ ID NO:2 and an insert of 33 amino acids is found after residue 623, as defined in SEQ ID NO:2. Recombinant host cells stably transformed or transfected with an expression construct of the invention in a manner allowing the expression in the host cell of a protein product of the expression construct also are contemplated.

The host cells may be mammalian, a bacterial, yeast cells, or insect cells. It may be advantageous that the recombinant host cells produced by the invention further express one or more β-subunits of a sodium channel selected from the group consisting of β1, β2, β3 and β4. In specific embodiments, the host cell is a HEK293 cell line.

The invention further provides an isolated and purified protein comprising an amino acid sequence selected from the group consisting of an amino acid sequence set forth in SEQ ID NO:2 and the mature protein portion of SEQ ID NO:2, wherein the mature protein portion comprises an aspartic acid residue at the amino acid residue that corresponds to amino acid residue 208 of SEQ ID NO:2 and an insert of 33 amino acids is found after residue 623, as defined in SEQ ID NO:2. In particular embodiments, the isolated and purified protein comprises an amino acid sequence that is 99% identical to the complete sequence set forth in SEQ ID NO:2. In other embodiments, the isolated and purified protein comprises an amino acid sequence that is 95% identical to the complete sequence of SEQ ID NO:2 and contains a 33 amino acid insert of SEQ ID NO:3.

The invention also comprises a diagnostic kit for detecting a nucleic acid that encodes a sodium channel α-subunit polypeptide, the polypeptide being encoded by the sequence presented in SEQ ID NO: 1, comprising an isolated nucleic acid probe complementary to the complete sequence of SEQ ID NO: 1, and means for containing the nucleic acid.

Methods of identifying a modulator of a human sodium channel α-subunit expression or activity are contemplated wherein the modulator is identified by a method comprising the steps of contacting a cell that expresses a nucleic acid of SEQ ID NO:1 with the candidate modulator substance; monitoring the expression or ion channel activity of a protein of SEQ ID NO:2; and comparing the expression or ion channel activity of a protein of SEQ ID NO:2 in the presence and absence of the candidate substance; wherein an alteration in the expression or ion channel activity of a protein of SEQ ID NO:2 indicates that the substance is a modulator of human sodium channel α-subunit expression or activity. The modulator of human sodium channel α-subunit expression or activity may be a small molecule ion channel blocker or inhibitor, an oligonucleotide, an antisense oligonucleotide, a DNA oligonucleotide, an RNA oligonucleotide, an RNA oligonucleotide having at least a portion of the RNA oligonucleotide capable of hybridizing with RNA to form an oligonueleotide-RNA duplex, or a chimeric oligonucleotide.

The invention also provides methods of identifying a test compound that binds to a sodium channel comprising providing a cell that expresses a sodium channel having a sequence of SEQ ID NO:2; contacting the host cell with the test compound and determining the binding of the test compound to the sodium channel; and comparing the binding of the test compound to the host cell determined in step (b) to the binding of the test compound with a cell that does not express a sodium channel.

Also provided is an assay for identifying a test compound that modulates the activity of a sodium channel comprising providing a host cell that expresses a functional sodium channel comprising at least one polypeptide comprising the amino acid sequence of SEQ ID NO: 2, contacting the host cell with a test compound under conditions that would activate sodium channel activity of the functional sodium channel in the absence of the test compound; and determining whether the host cell contacted with the test compound exhibits a modulation in activity of the functional sodium channel. In particular embodiments, the host cell has been genetically engineered to express or overexpress the functional sodium channel. In other embodiments, the host cell has been genetically engineered by the introduction into the cell of a nucleic acid molecule having a nucleotide sequence encoding a polypeptide comprising the amino acid sequence set forth in SEQ ID NO: 2. Preferably, the host cell has been genetically engineered to upregulate the expression of a nucleic acid encoding a polypeptide comprising the amino acid sequence of SEQ ID NO: 2. In particular embodiments, the upregulated nucleic acid is endogenous to the host cell. Preferably, the modulation of the functional sodium channel activity is an inhibition of that activity.

A method of producing a purified human sodium channel α-subunit protein also is provided, the method comprising preparing an expression construct comprising a nucleic acid of SEQ ID NO:1 operably linked to a promoter; transforming or transfecting a host cell with the expression construct in a manner effective to allow the expression of a protein having an amino acid sequence of SEQ ID NO:2, or the mature protein portion thereof in the host cell; culturing the transformed or transfected cell under conditions to allow the production of the protein by the transformed or transfected host cell; and isolating the human sodium channel α-subunit protein from the host cell.

Other embodiments contemplate treatment of a disorder by administering to a subject in need thereof a pharmaceutical composition that comprises a compound identified according to the methods described herein and a pharmaceutically acceptable carrier, excipient or diluent.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIGS. 1A through 1F shows the sequence alignment of the sequence of the present invention (SEQ ID NO:2) with sequences (SEQ ID NO:4; SEQ ID NO:5; SEQ ID NO:6; SEQ ID NO:7; SEQ ID NO:8) identified from Genbank.

DESCRIPTION OF THE PREFERRED EMBODIMENTS

Human $Na_V1.3$ is a voltage-gated sodium channel α-subunit whose expression has been shown to be upregulated in neurons that have been subjected to various injuries such as e.g., after axotomy of peripheral projections, after chronic constriction injury, and after tight spinal nerve ligation. Reduction or knockout Nav1.3 alleviates the pain associated with such injuries. Thus, therapies designed to knock-out or block the action of Nav1.3 are important in alleviating neuropathy. The present application is directed to a novel splice variant of the α1 subunit of human Nav 1.3.

The splice variant of the human $Na_V1.3$ channel α subunit of the present invention was identified from human spinal cord RNA using RT-PCR to amplify the message in three overlapping fragments as described in the Examples herein below. The three fragments were then ligated together to create the full-length sequence. The cDNA clone isolated is a novel splice variant that differs from previously reported Nav1.3 cDNAs. This Nav1.3 cDNA was used to express human Nav1.3 in cultured cell lines. The Nav 1.3-expressing line was used in high-throughput screening to identify antagonists of Nav 1.3 and has been used to characterize the activity of such agents against the channel. Methods and compositions for making and using the splice variant of the present invention are described in further detail below.

Polypeptide and Fragments Thereof.

According to the present invention, there has been identified a gene that encodes a novel splice variant of human Nav1.3. It is contemplated that this gene and the protein encoded by the same may be used in studies of sodium channels and in the identification of modulators thereof. In this regard, it is noted that sodium channel α-subunits are well known to those of skill in the art and have been described e.g., in U.S. Pat. No. 6,479,259; U.S. Pat. No. 6,335,172; U.S. Pat. No. 6,184,349; U.S. Pat. No. 6,060,271; U.S. Pat. No. 6,030,810; U.S. Pat. No. 5,892,018; U.S. Pat. No. 5,776,859; U.S. Pat. No. 5,693,756; U.S. Pat. No. 5,437,982; U.S. Pat. No. 5,380,836. Each of the foregoing patents are incorporated herein by reference as providing specific teaching of how to make and use sodium channel proteins and nucleic acids that encode the same. The methods taught therein for using such compositions to identify therapeutic agents, e.g., sodium channel blockers or even β-subunits that are modulators of sodium channel α-subunits may readily be adapted using the protein and nucleic acid compositions of the present invention. As discussed above, Nav1.3 sodium channels are involved in mediating pain associated with neuronal injury. As such, it is contemplated that it will be will be desirable to inhibit, decrease, ablate, reduce or otherwise diminish the expression of the Nav1.3 gene or the activity of the protein product of the gene expression described herein. It is contemplated that inhibition of activity of the encoded protein or the expression of this gene will have a beneficial effect in treating pain. Inhibition of the gene expression may even be helpful in regenerative studies or overcoming the deleterious effects of spinal cord injury.

In the therapeutic aspects, guidance may be gained from the functional and therapeutic aspects of sodium channels described in e.g., in U.S. Pat. No. 6,479,259; U.S. Pat. No. 6,335,172; U.S. Pat. No. 6,184,349; U.S. Pat. No. 6,060,271; U.S. Pat. No. 6,030,810; U.S. Pat. No. 5,892,018; U.S. Pat. No. 5,776,859; U.S. Pat. No. 5,693,756; U.S. Pat. No. 5,437, 982; U.S. Pat. No. 5,380,836 been recognized as being involved in pain and have been used as targets for therapy. Sodium channel blockers or modulators have been described e.g., in U.S. Pat. No. 6,756,400; U.S. Pat. No. 6,646,012; U.S. Pat. No. 6,613,345; U.S. Pat. No. 6,607,741; U.S. Pat. No. 6,559,154; U.S. Pat. No. 6,479,498 (each incorporated by reference) and such patents provide guidance as to methods and compositions for identification of additional such therapeutic agents once new targets such as the Nav1.3 splice variant of the present invention, are identified. While treatment of pain and the like will involve inhibition or blocking of Nav1.3 activity, it is contemplated that in certain embodiments, it may be desirable to increase the expression of Nav1.3. For example, in specific embodiments, it would be desirable to increase, augment or otherwise supplement endogenous Nav1.3 expression and/or activity in commercial or experimental endeavors where it would be desirable to produce animal models or cells that have an increased Nav1.3 expression and are phenotypically models for neuropathic pain.

The Nav1.3 splice variant encoding gene has been cloned by the present inventors and is taught herein to have a nucleic acid sequence as shown in SEQ ID NO:1. The coding region of this gene encodes a protein of SEQ ID NO:2. It is noted that the encoded protein has an aspartic acid residue at an amino acid that corresponds to residue number 208 of SEQ ID NO:2. A sequence alignment of the sequence of SEQ ID NO:2 with other sodium channel alpha subunit proteins is shown in FIG. 1. As can be seen in FIG. 1, there is an aspartic acid residue at amino acid residue 208. Further, SEQ ID NO:2 comprises an insert of NVSQASM SSRMVPGLPANGKMHSTVDC-NGVVSL that is not present in other sodium channel alpha subunits examined in FIG. 1. This 33 amino acid insert that starts at residue 624 of the NAV1.3 splice variant of the present invention. This region is the linker between domain 1 and domain 2 of the sodium channel alpha subunit. Protein kinase A phosphorylation sites of the sodium channel are located in this region and are close to this splice site. The sodium channel activity of the protein of SEQ ID NO:2 or a variant thereof that contains aspartic acid at an amino acid residue that corresponds to amino acid 208 of the Nav1.3 splice variant of the present invention may be readily tested using techniques well known to those of skill in the art.

In addition to the entire Nav1.3 protein molecule of SEQ ID NO:2, de compositions of the present invention also may employ fragments of the polypeptide of SEQ ID NO:2 that retain the ability/activity to form a sodium channel and retain an aspartic acid at a residue that corresponds to amino acid residue 208 of SEQ ID NO:2. Fragments, including the N-terminus or C terminus of the molecule may be generated by genetic engineering of translation start or stop sites within the coding region (discussed below). Alternatively, treatment of the Nav1.3 splice variant protein molecule with proteolytic enzymes, (proteases), can produce a variety of N-terminal, C-terminal and internal fragments. Examples of fragments may include contiguous residues of the Nav1.3 splice variant protein sequence of SEQ ID NO:2 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length. Such fragments preferably retain one or more of the biological activities of Nav1.3 protein and/or retain an immunological (antigenic) property of Nav1.3 protein. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

When the present application refers to the function of Nav1.3 splice variant protein or "wild-type" activity, it is meant that the molecule in question has the ability to form a sodium channel in a plasma membrane fraction. The Nav1.3 protein of the present invention has a sequence of SEQ ID NO:2. An assessment of the particular molecules that possess such activities may be achieved using standard assays familiar to those of skill in the art. For example, the immunological studies will readily reveal whether the Nav1.3 splice variant binds to antibodies directed against Nav1.3 or other sodium channel alpha subunits. Such antibodies are known to those of skill in the art and may be readily generated using routine methods.

In certain embodiments, Nav1.3 protein analogs and variants may be prepared and will be useful in a variety of applications. Amino acid sequence variants of the polypeptide can be substitutional, insertional or deletion variants. Deletion variants lack one or more residues of the native protein which are not essential for function or immunogenic activity. A common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, also called fusion proteins, are discussed below.

Substitutional variants typically exchange one amino acid of the wild type for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In order to construct such mutants, one of skill in the art may employ well known standard technologies. Specifically contemplated are N-terminal deletions, C-terminal deletions, internal deletions, as well as random and point mutagenesis.

N-terminal and C-terminal deletions are forms of deletion mutagenesis that take advantage for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Alternatively, deletions can be generated using polymerase chain reaction (PCR) amplification of cDNAs using primers that exclude regions of the coding sequence corresponding to the desired polypeptide deletion. Proteins expressed from such mutants can be assayed for appropriate activity as voltage-gated sodium channels, as described throughout the specification. Similar techniques may be employed for internal deletion mutants by using two suitably placed restriction sites, thereby allowing a precisely defined deletion to be made, and the ends to be religated as above. as above. Similarly, PCR can be used to amplify the sequences flanking the internal deletion and then ligation used as described above to generate the DNA clone containing the desired deletion.

Also contemplated are partial digestion mutants. In such instances, one of skill in the art would employ a "frequent cutter", which cuts the DNA in numerous places depending on the length of reaction time. Thus, by varying the reaction conditions it will be possible to generate a series of mutants of varying size, which may then be screened for activity.

A random insertional mutation may also be performed by cutting the DNA sequence with a DNase I, for example, and inserting a stretch of nucleotides that encode, 3, 6, 9, 12 etc., amino acids and religating the end. Once such a mutation is made the mutants can be screened for various activities presented by the wild-type protein.

Point mutagenesis also may be employed to identify with particularity which amino acid residues are important in particular activities associated with Nav1.3 splice variant protein. Thus, one of skill in the art will be able to generate single base changes in the DNA strand to result in an altered codon and a missense mutation.

The amino acids of a particular protein can be altered to create an equivalent, or even an improved, second-generation molecule. Such alterations contemplate substitution of a given amino acid of the protein without appreciable loss of interactive binding capacity with structures such as, for example, antigen-binding regions of antibodies or binding sites on substrate molecules or receptors. Since it is the interactive capacity and nature of a protein that defines that protein's biological functional activity, certain amino acid substitutions can be made in a protein sequence, and its underlying DNA coding sequence, and nevertheless obtain a protein with like properties. Thus, various changes can be made in the DNA sequences of genes without appreciable loss of their biological utility or activity, as discussed below. Codon tables that show the codons that encode particular amino acids are well known to those of skill in the art. In making changes to the sequence of SEQ ID NO:2, the hydropathic index of amino acids may be considered, which contributes to the secondary structure of the resultant protein, which in turn defines the interaction of the protein with other molecules, for example, enzymes, substrates, receptors, DNA, antibodies, antigens, and the like (Kyte & Doolittle, J. Mol. Biol., 157(1):105-132, 1982, incorporated herein by reference). Generally, amino acids may be substituted by other amino acids that have a similar hydropathic index or score and still result in a protein with similar biological activity, i.e., still obtain a biological functionally equivalent protein. Hydrophilicity is another parameter that may be used to determine amino acid substitution (see e.g., U.S. Pat. No. 4,554,101).

Exemplary amino acid substitutions that may be used in this context of the invention include but are not limited to exchanging arginine and lysine; glutamate and aspartate; serine and threonine; glutamine and asparagine; and valine, leucine and isoleucine. Other such substitutions that take into account the need for retention of some or all of the biological activity whilst altering the secondary structure of the protein will be well known to those of skill in the art.

Another type of variant that is specifically contemplated for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of Nav1.3 protein, but with altered and even improved characteristics.

Other mutants that are contemplated are those in which entire domains of the Nav1.3 protein are switched with those of another related protein. For example, other sodium channels exist and chimeric sodium channels may be produced where domains from e.g., a Nav1.8 protein are switched with domains from the Nav1.3. Domain switching is well-known to those of skill in the art and is particularly useful in generating mutants having domains from related species.

Domain switching involves the generation of chimeric molecules using different but related polypeptides. For example, by comparing the sequence of Nav1.3 protein with that of similar sequences from another source and with mutants and allelic variants of these polypeptides, one can make predictions as to the functionally significant regions of these molecules. Thus, it is contemplated then to switch related domains of these molecules in an effort to determine the criticality of these regions to Nav1.3 protein function. These molecules may have additional value in that these "chimeras" can be distinguished from natural molecules, while possibly providing the same or even enhanced function.

In addition to the mutations described above, the present invention further contemplates the generation of a specialized kind of insertional variant known as a fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione S-transferase (GST) system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). These systems are capable of producing recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Another N terminal fusion that is contemplated to be useful is the fusion of a Met Lys dipeptide at the N terminal region of the protein or peptides. Such a fusion may produce beneficial increases in protein expression or activity.

A particularly useful fusion construct may be one in which a Nav1.3 splice variant of the present invention is fused to a hapten to enhance immunogenicity of a Nav1.3 protein fusion construct. Such fusion constructs to increase immunogenicity are well known to those of skill in the art, for example, a fusion of Nav1.3 protein with a helper antigen such as hsp70 or peptide sequences such as from Diptheria toxin chain or a cytokine such as IL-2 will be useful in eliciting an immune response. In other embodiments, fusion construct can be made which will enhance the targeting of the Nav1.3 protein-related compositions to a specific site or cell.

Other useful fusions include Nav1.3 protein fused to specific peptide or polypeptide domains that serve to increase cell surface expression of membrane proteins. Examples of such domains include one known to increase the cell surface expression of potassium channels by facilitating exit from the endoplasmic reticulum (see Zerangue et al Neuron 22, 537).

Other fusion constructs including a heterologous polypeptide with desired properties also are contemplated. Other fusion systems produce polypeptide hybrids where it is desirable to excise the fusion partner from the desired polypeptide. In one embodiment, the fusion partner is linked to the recombinant Nav1.3 protein polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

It will be desirable to purify Nav1.3 protein or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing; affinity columns specific for protein fusion moieties; affinity columns containing Nav1.3-specific antibodies. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur. As is common with purification of transmembrane proteins such as ion channels, it is possible that the purified protein may need to be incorporated in synthetic liposomes to retain biological activity.

Incorporation of proteins into liposomes is well known to those of skill in the art. The most frequently used strategy for reconstitution and crystallization of transmembrane proteins in lipid bilayers is comicellization of the proteins and lipids, both solubilized with detergent, which is removed after mixing the separate solutions (e.g., Jap et al., Ultramicroscopy. 46:45-84, 1992; Kühlbrandt, Q. Rev. Biophys. 25:1-49, 1992; Rigaud et al., Struct. Biol. 118:226-235, 1995; Mosser, Micron. 32:517-540, 2001). Additional chemical agents are usually added to the solution, including e.g., detergents such as octyl thioglucoside (Scheuring et al., EMBO J. 20:3029-3035, 2001), octyl glucoside, octyl glucopyranoside (Montoya et al., J. Mol. Biol. 250:1-10, 1995), organic solvents such as pentane, hexane, or other chemicals such as glucose (Walz et al., J. Mol. Biol. 282:833-845, 1998) or glycerol (Ikeda-Yamasaki et al., FEBS Lett. 425:505-508, 1998). The concentration of the detergent molecules in these solutions is then gradually reduced, either by dialysis or by the addition of Bio-Beads (Rigaud et al., J. Struct. Biol. 118:226-235, 1997). As the concentration of the detergent decreases from these lipid-detergent and lipid-protein-detergent micellar solutions, lipid bilayers are progressively formed in which the transmembrane proteins are incorporated. Usually, the morphology of the resulting 2D crystals depends on several poorly defined factors, and depending on the circumstances, various structures can be obtained such as planar sheets, proteo-liposomes, multilayered stacked sheets, thin three-dimensional crystals, and tubes (Lacapere et al., Biophys. J. 75:1319-1329, 1998; Mosser, Micron. 32:517-540, 2001). Specifically contemplated compositions of the present invention include the Nav1.3 splice variants of the present invention incorporated into a liposomal preparation using techniques such as those outlined above. The splice variant protein compositions for incorporation into the liposomes may be prepared and purified using any standard protein preparation techniques.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that wider differing electrophoresis conditions, the apparent molecular weights of purified or partially purified expression products may vary.

In addition to the full length Nav1.3 protein of SEQ ID NO:2 described herein, smaller Nav1.3 protein-related peptides derived from the sequence of SEQ ID NO:2 and containing at least the aspartic acid residue at the relative position number 208 of SEQ ID NO:2 (i.e., in SEQ ID NO:2 the aspartic acid residue in question is at position 208, in other proteins that residue may be at another position along the amino acid sequence but it is in a position that corresponds to or is derived from position 208 of SEQ DI NO:2) may be useful in various embodiments of the present invention. Such peptides or indeed even the full length protein, of the invention can also be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co., (1984); Tam et al., J. Am. Chem. Soc., 105:6442, (1983); Merrifield, *Science,* 232: 341-347, (1986); and Barany and Merrifield, The Peptides, Gross and Meienhofer, eds, Academic Press, New York, 1-284, (1979), each incorporated herein by reference. The Nav1.3 active protein or portions of the protein, which correspond to the selected regions described herein, can be readily synthesized and then screened in screening assays designed to identify reactive peptides.

Alternatively, recombinant DNA technology may be employed wherein a nucleotide sequence which encodes a peptide of the invention is inserted into an expression vector, transformed or transfected into an appropriate host cell and cultivated under conditions suitable for expression as described herein below.

U.S. Pat. No. 4,554,101 (incorporated herein by reference) also teaches the identification and preparation of epitopes from primary amino acid sequences on the basis of hydrophilicity. Thus, one of skill in the art would be able to identify epitopes from within any amino acid sequence encoded by any of the DNA sequences disclosed herein.

The protein of SEQ ID NO:2 or proteins and peptides derived therefrom, may be useful as antigens for the immunization of animals relating to the production of antibodies. It is envisioned that such protein, or portions thereof, may be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

$N_{AV}$1.3 Splice Variant Encoding Nucleic Acids

The present invention also provides, in another embodiment, an isolated nucleic acid encoding the Nav1.3 splice variant protein of the invention. Preferred embodiments of the present invention are directed to nucleic acid constructs comprising a sequence of SEQ ID NO:1. Preferably, the sequence is operably linked to a heterologous promoter. The present invention is not limited in scope to the particular gene(s) identified herein, however, seeing as one of ordinary skill in the art could, using the nucleic acids corresponding to the Nav1.3 gene, readily identify related homologs in various other species (e.g., rat, rabbit, monkey, gibbon, chimp, ape, baboon, cow, pig, horse, sheep, cat and other species).

In addition, it should be clear that the present invention is not limited to the specific nucleic acids disclosed herein. As discussed below, a "Nav1.3 gene" may contain a variety of different nucleic acid bases and yet still produce a corresponding polypeptide that is functionally indistinguishable, and in some cases structurally, from the human gene disclosed herein. In preferred embodiments, the nucleic acids encode SEQ ID NO:2. In other embodiments the nucleic acids encode a function sodium channel alpha subunit based on the amino acid sequence of SEQ ID NO:2 which at least comprises an aspartic acid residue at the amino acid that corresponds to the amino acid at position 208 of SEQ ID NO:2, and has an insertion of a linker between Domain 1 and Domain 2. The term "Nav1.3 gene" may be used to refer to any nucleic acid that encodes such a protein, peptide or polypeptide and, as such, is intended to encompass both genomic DNA, mRNA and cDNA.

Similarly, any reference to a nucleic acid should be read as encompassing a host cell containing that nucleic acid and, in some cases, capable of expressing the product of that nucleic acid. Such cells expressing nucleic acids of the present invention are contemplated to be particularly useful in the context of screening for agents that induce, repress, inhibit, augment, interfere with, block, abrogate, stimulate or enhance the function of Nav1.3 gene or protein product. Such compounds identified in these screening assay embodiments also will be useful as sodium channel modulators of other sodium channels (e.g., Nav1.8, Nav1.6 and the like)

Nucleic acids according to the present invention (which include genomic DNA, cDNA, mRNA, as well as recombinant and synthetic sequences and partially synthetic sequences) may encode an entire Nav1.3 protein of SEQ ID NO:2, or polypeptide, or allelic variant, a domain of the protein that expresses an activity of the wild-type sodium channel and has an aspartic acid residue at a position that corresponds to residue 208 of SEQ ID NO:2, or any other fragment or variant of the Nav1.3 protein sequences set forth herein, as long as those variant comprise a linker between Domain 1 and Domain 2 as described herein.

The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that due to the redundancy of the genetic code, a given Nav1.3 gene from a given species may be represented by degenerate variants that have slightly different nucleic acid sequences but, nonetheless, encode the same protein.

As used in this application, the term "a nucleic acid encoding a Nav1.3 protein" refers to a nucleic acid molecule that has been isolated from total cellular nucleic acid. In preferred embodiments, the invention concerns a nucleic acid sequence essentially as net forth in SEQ ID NO:1. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | Codons |
|---|---|---|
| Alanine | Ala A | GCA GCC GCG GCU |
| Cysteine | Cys C | UGC UGU |
| Aspartic acid | Asp D | GAC GAU |
| Glutamic acid | Glu E | GAA GAG |
| Phenylalanine | Phe F | UUC UUU |
| Glycine | Gly G | GGA GGC GGG GGU |
| Histidine | His H | CAC CAU |
| Isoleucine | Ile I | AUA AUC AUU |
| Lysine | Lys K | AAA AAG |
| Leucine | Leu L | UUA UUG CUA CUC CUG CUU |
| Methionine | Met M | AUG |
| Asparagine | Asn N | AAC AAU |
| Proline | Pro P | CCA CCC CCG CCU |
| Glutamine | Gln Q | CAA CAG |
| Arginine | Arg R | AGA AGG CGA CGC CGG CGU |
| Serine | Ser S | AGC AGU UCA UCC UCG UCU |
| Threonine | Thr T | ACA ACC ACG ACU |
| Valine | Val V | GUA GUC GUG GUU |
| Tryptophan | Trp W | UGG |
| Tyrosine | Tyr Y | UAC UAU |

Nucleotide sequences that have at least about 95% of nucleotides that are identical to the nucleotides of the entire sequence of SEQ ID NO:1 are preferred. Sequences that are essentially the same as those set forth in SEQ ID NO:1 may also be functionally defined as sequences that are capable of hybridizing to a nucleic acid segment containing the complement of SEQ ID NO:1 under standard conditions.

The DNA segments of the present invention include those encoding biologically functional equivalent Nav1.3 proteins and peptides as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through any means described herein or known to those of skill in the art.

The present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under highly stringent conditions. Such sequences may encode the entire Nav1.3 protein of SEQ ID. NO:2 or functional or non-functional fragments thereof.

Alternatively, the hybridizing segments may be shorter oligonucleotides. Sequences of about 17 bases long should occur only once in the human genome and, therefore, suffice to specify a unique target sequence. Antisense nucleic acids directed against the sequence of SEQ ID NO:1 are particularly useful.

Suitable hybridization conditions will be well known to those of skill in the art. In certain applications, it is appreciated that lower stringency conditions may be required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form.

Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement. Site-directed mutagenesis can also be accomplished using PCR to introduce the desired alteration in the coding sequence. In this case, one of the amplification primers contains the alteration(s) of choice and results in a DNA fragment containing the desired mutation(s) that can then be incorporated into the full-length construct.

Of course site-directed mutagenesis is not the only method of generating potentially useful mutant protein species and as such is not meant to be limiting. The present invention also contemplates other methods of achieving mutagenesis such as for example, treating the recombinant vectors carrying the gene of interest mutagenic agents, such as hydroxylamine, to obtain sequence variants.

It will be useful to inhibit the expression of Nav1.3 to decrease the activity of the encoded protein and effect and ameliorative outcome on pain. One may advantageously disrupt the activity or expression of a protein using a variety of methods known to those of skill in the art. For example, nucleic acid-based methods of disrupting or block Nav1.3 expression are contemplated. Polynucleotide products which are useful in this endeavor include antisense polynucleotides, ribozymes, RNAi, and triple helix polynucleotides that modulate the expression of Nav1.3.

Antisense polynucleotides and ribozymes are well known to those of skill in the art. Crooke and B. Lebleu, eds. Antisense Research and Applications (1993) CRC Press; and Antisense RNA and DNA (1988) D. A. Melton, Ed. Cold Spring Harbor Laboratory Cold Spring Harbor, N.Y. Antisense RNA and DNA molecules act to directly block the translation of mRNA by binding to targeted mRNA and preventing protein translation. An example of an antisense polynucleotide is an oligodeoxyribonucleotide derived from the translation initiation site, e.g., between −10 and +10 regions of the relevant nucleotide sequence.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarily to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozymes) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

As indicated above, the DNA and protein sequences for the specific splice variant of the present invention are provided in SEQ ID NO:1 and SEQ ID NO:2, respectively. Related protein and/or nucleic acid sequences from other sources may be identified using probes directed at the sequences of SEQ ID NO:1. Such additional sequences may be useful in certain aspects of the present invention. Although antisense sequences may be full length genomic or cDNA copies, they also may be shorter fragments or oligonucleotides e.g., polynucleotides of 100 or less bases. Although shorter oligomers (8-20) are easier to make and more easily permeable in vivo, other factors also are involved in determining the specificity of base pairing. For example, the binding affinity and sequence specificity of an oligonucleotide to its complementary target increases with increasing length. It is contemplated that oligonucleotides of 8, 9, 10, 11, 12, 13, 14, 15, 16, 17, 18, 19, 20, 25, 30, 35, 40, 45, 50, or more base pairs will be used.

Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569; and U.S. Pat. No. 5,093,246.

Nucleic acid molecules used in triple helix formation for the inhibition of transcription are generally single stranded and composed of deoxyribonucleotides. The base composition must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Another technique that is of note for reducing or disrupting the expression of a gene is RNA interference (RNAi), also known as small interfering RNA (siRNA). The term "RNA interference" was first used by researchers studying *C. elegans* and describes a technique by which post-transcriptional gene silencing (PTGS) is induced by the direct introduction of double stranded RNA (dsRNA: a mixture of both sense and antisense strands). Injection of dsRNA into *C. elegans* resulted in much more efficient silencing than injection of either the sense or the antisense strands alone (Fire et al., Nature 391:806-811, 1998). Just a few molecules of dsRNA per cell is sufficient to completely silence the expression of the homologous gene. Furthermore, injection of dsRNA caused gene silencing in the first generation offspring of the *C. elegans* indicating that the gene silencing is inheritable (Fire et al., Nature 391:806-811, 1998). Current models of PTGS indicate that short stretches of interfering dsRNAs (21-23 nucleotides; siRNA also known as "guide RNAs") mediate PTGS. siRNAs are apparently produced by cleavage of dsRNA introduced directly or via a transgene or virus. These siRNAs may be amplified by an RNA-dependent RNA polymerase (RdRP) and are incorporated into the RNA-induced silencing complex (RISC), guiding the complex to the homologous endogenous mRNA, where the complex cleaves the transcript. Thus, siRNAs are nucleotides of a short length (typically 18-25 bases, preferably 19-23 bases in length) which incorporate into an RNA-induced silencing complex in order to guide the complex to homologous endogenous mRNA for cleavage and degradation of the transcript.

While most of the initial studies were performed in *C. elegans*, RNAi is gaining increasing recognition as a technique that may be used in mammalian cell. It is contemplated that RNAi, or gene silencing, will be particularly useful in the disruption of tissue-specific gene expression. By placing a gene fragment encoding the desired dsRNA behind an inducible or tissue-specific promoter, it should be possible to inactivate genes at a particular location within an organism or during a particular stage of development.

Variations on RNA interference (RNAi) technology is revolutionizing many approaches to experimental biology, complementing traditional genetic technologies, mimicking the effects of mutations in both cell cultures and in living animals. (McManus & Sharp, Nat. Rev. Genet. 3, 737-747 (2002)). RNAi has been used to elicit gene-specific silencing in cultured mammalian cells using 21-nucleotide siRNA duplexes (Elbashir et al., Nature, 411:494-498, 2001; Fire et al., Nature 391, 199-213 (1998), Harmon, G. J., Nature 418, 244-251 (2002))). In the same cultured cell systems, transfection of longer stretches of dsRNA yielded considerable nonspecific silencing. Thus, RNAi has been demonstrated to be a feasible technique for use in mammalian cells and could be used for assessing gene function in cultured cells and mammalian systems, as well as for development of gene-specific therapeutics. In particularly preferred embodiments, the siRNA molecule is between 20 and 25 oligonucleotides in length an is derived from the sequence of SEQ ID NO:1. Particularly preferred siRNA molecules are 21-23 bases in length.

Anti-sense RNA and DNA molecules, ribozymes, RNAi and triple helix molecules can be prepared by any method known in the art for the synthesis of DNA and RNA molecules. These include techniques for chemically synthesizing oligodeoxyribonucleotides well known in the art including, but not limited to, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably or transiently into cells.

Commercial providers such as Ambion Inc. (Austin, Tex.), Darmacon Inc. (Lafayette, Colo.), InvivoGen (San Diego, Calif.), and Molecula Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.). These siRNA molecules may be introduced into cells through transient transfection or by introduction of expression vectors that continually express the siRNA in transient or stably transfected mammalian cells. Transfection may be accomplished by well known methods including methods such as infection, calcium chloride, electroporation, microinjection, lipofection or the DEAE-dextran method or other known techniques. These techniques are well known to those of skill in the art.

Recombinant Protein Production.

Given the above disclosure of SEQ ID NO:1, it is possible to produce a protein of SEQ ID NO:2 by recombinant techniques. A variety of expression vector/host systems may be utilized to contain and express such a protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein production include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of a protein of amino acid sequence of SEQ ID NO:2 in bacteria, yeast and other invertebrates are described herein below.

The DNA sequence encoding the mature form of the protein is amplified by PCR and cloned into an appropriate vector for example, pGEX 3X (Pharmacia, Piscataway, N.J.). The pGEX vector is designed to produce a fusion protein comprising glutathione S transferase (GST), encoded by the vector, and a protein encoded by a DNA fragment inserted into the vectors cloning site. The primers for the PCR may be generated to include for example, an appropriate cleavage site.

Treatment of the recombinant fusion protein with thrombin or factor Xa (Pharmacia, Piscataway, N.J.) is expected to cleave the fusion protein, releasing the proapoptotic factor from the GST portion. The pGEX 3X/Nav1.3 protein construct is transformed into *E. coli* XL 1 Blue cells (Stratagene, La Jolla Calif.), and individual transformants were isolated and grown. Plasmid DNA from individual transformants is purified and partially sequenced using an automated sequencer to confirm the presence of the desired protein-encoding gene insert in the proper orientation.

Knowledge of SEQ ID NO:1 gene sequences allows for modification of cells to permit or increase expression of endogenous Nav1.3 splice variant of the present invention. The cells can be modified (heterologous promoter is inserted in such a manner that it is operably linked to, e.g., by homologous recombination) to provide increased protein expression by replacing, in whole or in part the naturally occurring promoter with all or part of a heterologous promoter so that the cells express such a protein at higher levels. The heterologous promoter is inserted in such a manner that it is operably linked to gene sequence of SEQ ID NO:1. (e.g., PCT International Publication No. WO96/12650; PCT International Publication No. WO 92/20808 and PCT International Publication No. WO 91/09955). It is contemplated that, in addition to the heterologous promoter DNA, amplifiable marker DNA (e.g., ada, dhfr and the multifunctional CAD gene which encodes carbamyl phosphate synthase, aspartate transcarbamylase and dihydroorotase) and/or intron DNA may be inserted along with the heterologous promoter DNA. If linked to the gene sequence, amplification of the marker DNA by standard selection methods results in co-amplification of the Nav1.3 splice variant with the marker sequence in the cells.

While certain embodiments of the present invention contemplate producing the Nav1.3 splice variant protein using synthetic peptide synthesizers and subsequent FPLC analysis and appropriate refolding of the cysteine double bonds, it is contemplated that recombinant protein production also may be used. For example, induction of the fusion protein containing the protein of interest fused to GST is achieved by growing the transformed XL 1 Blue culture at 37° C. in LB medium (supplemented with carbenicillin) to an optical density at wavelength 600 nm of 0.4, followed by further incubation for 4 hours in the presence of 0.5 mM Isopropyl β-D Thiogalactopyranoside (Sigma Chemical Co., St. Louis Mo.).

The fusion protein, expected to be produced as an insoluble inclusion body in the bacteria, may be purified using standard techniques in which cells are harvested, washed, lysed and the protein extracted and purified e.g., using the GST Purification Module (Pharmacia Biotech). The GST may be cleaved using thrombin digestion.

The recombinant protein also may be prepared using a yeast system e.g., the Pichia Expression System (Invitrogen, San Diego, Calif.), following the manufacturer's instructions. Alternatively, the cDNA encoding the given Nav1.3 splice variant protein may be cloned into the baculovirus expression vector pVL1393 (PharMingen, San Diego, Calif.). This vector is then used according to the manufacturer's directions (PharMingen) to infect *Spodoptera frugiperda* cells in sF9 protein free media and to produce recombinant protein. The protein is purified and concentrated from the media using a heparin Sepharose column (Pharmacia, Piscataway, N.J.) and sequential molecular sizing columns (Amicon, Beverly, Mass.), and resuspended in PBS. SDS PAGE analysis shows a single band and confirms the size of the protein, and Edman sequencing on a Porton 2090 Peptide Sequencer confirms its N terminal sequence. In still other alternatives, the an insect system expression system may be used.

Mammalian host systems for the expression of the recombinant protein also are well known to those of skill in the art and are most preferred. Host cell strains may be chosen for a particular ability to process the expressed protein or produce certain post translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection and its presence allows growth and recovery of cells which successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoritiosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; als which confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, glucuronidase and its substrate, GUS, and luciferase and its substrate, luciferin.

Vectors for Cloning, Gene Transfer and Expression

As discussed in the previous section, expression vectors are employed to express the protein of interest, which can then be purified and, for example, be used to vaccinate animals to generate antisera or monoclonal antibody with which further studies may be conducted.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the polypeptide.

Throughout this application, the term "expression construct" or "expression vector" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Exemplary promoters include the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well known properties, the level and pattern of expression of the protein of interest following transfection or transformation can be optimized. Inducible promoters e.g., inducible ecdysone system (Invitrogen, Carlsbad, Calif.), or the Tet-Off™ or Tet-On™ system which are designed to allow regulated expression of a gene of interest in mammalian cells also may be used.

Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Tissue specific promoters may be used to effect transcription in specific tissues or cells so as to reduce potential toxicity or undesirable effects to non-targeted tissues.

It is envisioned that any of the above promoters alone or in combination with another may be useful according to the present invention depending on the action desired. In addition, this list of promoters should not be construed to be exhaustive or limiting, and those of skill in the art will know of other promoters that may be used in conjunction with the promoters and methods disclosed herein.

Another regulatory element contemplated for use in the present invention is an enhancer. These are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well known to those of skill in the art and will depend on the particular expression system being employed (Scharf D et al Results Probl Cell Differ 20: 125-62, 1994; Bittner et al Methods in Enzymol 153: 516-544, 1987).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

In certain embodiments of the invention, the use of internal ribosome entry site (IRES) elements is contemplated to create multigene, or polycistronic, messages. In specific embodiments herein it is contemplated that host cells are created which comprise both a Nav1.3 alpha subunit and one or more beta subunits. IRES elements can be linked to heterologous open reading frames for such endeavors. IRES elements are able to bypass the ribosome scanning model of 5' methylated Cap dependent translation and begin translation at internal sites (Pelletier and Sonenberg, Nature, 334:320-325, 1988). IRES elements from two members of the picornavirus family (poliovirus and encephalomyocarditis) have been described (Pelletier and Sonenberg, 1988 supra), as well an IRES from a mammalian message (Macejak and Sarnow, Nature, 353: 90-94, 1991). Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

There are a number of ways in which expression constructs may be introduced into cells. In certain embodiments of the invention, the expression construct comprises a virus or engineered construct derived from a viral genome. In other embodiments, non-viral delivery such as lipid- or chemical-mediated transfection is contemplated. The ability of certain viruses to enter cells via receptor-mediated endocytosis, to integrate into host cell genome and express viral genes stably and efficiently have made them attractive candidates for the transfer of foreign genes into mammalian cells (Ridgeway, In: Rodriguez R L, Denhardt D T, ed. Vectors: A survey of molecular cloning vectors and their uses. Stoneham Butterworth, 467 492, 1988; Nicolas and Rubenstein, In: Vectors: A survey of molecular cloning vectors and their uses, Rodriguez & Denhardt (eds.), Stoneham: Butterworth, 493 513, 1988; Baichwal and Sugden, In: Gene Transfer, Kucherlapati R, ed., New York, Plenum Press, 117 148, 1986; Temin, In: gene Transfer, Kucherlapati (ed.), New York: Plenum Press, 149 188, 1986). The first viruses used as gene vectors were DNA viruses including the papovaviruses (simian virus 40, bovine papilloma virus, and polyoma) (Ridgeway, 1988 supra; Baichwal and Sugden, 1986 supra) and adenoviruses (Ridgeway, 1988 supra; Baichwal and Sugden, 1986 supra). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988 supra; Temin, 1986 supra).

It is now widely recognized that DNA may be introduced into a cell using a variety of viral vectors. In such embodiments, expression constructs comprising viral vectors containing the genes of interest may be adenoviral (see for example, U.S. Pat. No. 5,824,544; U.S. Pat. No. 5,707,618; U.S. Pat. No. 5,693,509; U.S. Pat. No. 5,670,488; U.S. Pat. No. 5,585,362; each incorporated herein by reference), retroviral (see for example, U.S. Pat. No. 5,888,502; U.S. Pat. No. 5,830,725; U.S. Pat. No. 5,770,414; U.S. Pat. No. 5,686,278; U.S. Pat. No. 4,861,719 each incorporated herein by reference), adeno-associated viral (see for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479 each incorporated herein by reference), an adenoviral-adenoassociated viral hybrid (see for example, U.S. Pat. No. 5,856,152 incorporated herein by reference) or a vaccinia viral or a herpesviral (see for example, U.S. Pat. No. 5,879,934; U.S. Pat. No. 5,849,571; U.S. Pat. No. 5,830,727; U.S. Pat. No. 5,661,033; U.S. Pat. No. 5,328,688 each incorporated herein by reference) vector. In preferred embodiments, retroviral vectors are used to introduce the expression construct into HEK293 cells.

Screening for Modulators of Sodium Channel Protein

The present invention also contemplates the use of human Nav1.3 splice variant of the present invention and active fragments thereof in the screening of compounds that modulate (increase or decrease activity) of sodium channels. Such modulators and particularly sodium channel blockers will be useful as therapeutic agents. Assays for the identification of these agents may make use of splice variants of the invention in a variety of different formats and may depend on the kind of "activity" for which the screen is being conducted.

a. Assay Formats.

The present invention provides methods of screening for modulators of human Nav1.3 sodium channel activity in vitro and in vivo in the presence and absence of the candidate substance and comparing such results. It is contemplated that this screening technique will prove useful in the general identification of compounds of therapeutic value against e.g., pain, inflammation, and other diseases or disorders associated with sodium channel activity. In preferred embodiments, it will be desirable to identify inhibitors of sodium channel activity. However, in other embodiments, stimulators of such activity also may be desirable.

In the screening embodiments, the present invention is directed to a method for determining the ability of a candidate substance to alter the sodium channel activity of cells that either naturally express Nav1.3 splice variant protein or have been engineered to express such a protein as described herein. Alternatively, the present application teaches the use of models for determining the in vivo effects of such compounds. The cells or animals also may then be contacted with additional sodium channel blockers in combination with a putative modulator of sodium channel function in order to determine whether the effect of such sodium channel blockers is increased or decreased as a result of the presence of the candidate substance.

An alteration in sodium channel activity, expression or processing in the presence of the candidate substance will indicate that the candidate substance is a modulator of the activity.

While the above method generally describes a sodium channel splice variant protein activity, it should be understood that candidate substance may be an agent that alters the expression of sodium channel protein, thereby increasing or decreasing the amount of Nav1.3 protein present as opposed to the per unit activity of the protein.

To identify a candidate substance as being capable of inhibiting protein activity, one would measure or determine the protein activity in the absence of the added candidate substance. One would then add the candidate inhibitory substance to the cell and determine the activity of protein in the presence of the candidate inhibitory substance. A candidate substance which is inhibitory would decrease the sodium channel activity. Exemplary such assays are described below.

b. Candidate Substances.

As used herein the term "candidate substance" refers to any molecule that is capable of modulating sodium channel Nav1.3 splice variant protein activity or expression. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known modulators of sodium channels. The active compounds may include fragments or parts of naturally-occurring compounds or may be only found as active combinations of known compounds which are otherwise inactive. However, prior to testing of such compounds in humans or animal models, it will be necessary to test a variety of candidates to determine which have potential.

Accordingly, the active compounds may include fragments or parts of naturally-occurring compounds or may be found as active combinations of known compounds which are otherwise inactive. Accordingly, the present invention provides screening assays to identify agents which inhibit or otherwise treat a disorder or associated with sodium channel activity. It is proposed that compounds isolated from natural sources, such as animals, bacteria, fungi, plant sources, including leaves and bark, and marine samples may be assayed as candidates for the presence of potentially useful pharmaceutical agents.

It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other inorganic or organic chemical compounds that may be designed through rational drug design starting from known agents that are used in the intervention of pain, inflammation or other diseases/disorders associated with sodium channel activity.

The candidate screening assays are simple to set up and perform. Thus, in assaying for a candidate substance, after obtaining a cell expressing functional Nav1.3 splice variant protein of the invention, one will admix a candidate substance with the cell, under conditions which would allow measurable sodium channel activity to occur. Exemplary sodium channel assays are provided below. In this fashion, one can measure the ability of the candidate substance to stimulate the activity of the cell in the absence of the candidate substance. Likewise, in assays for inhibitors after obtaining a cell expressing functional Nav1.3 splice variant protein, the candidate substance is admixed with the cell. In this fashion the ability of the candidate inhibitory substance to reduce, abolish, or otherwise diminish a biological effect mediated by Nav1.3 splice variant protein from said cell may be detected.

"Effective amounts" in certain circumstances are those amounts effective to reproducibly alter sodium channel associated activity of the cell or animal in comparison to the normal levels of such an event. Compounds that achieve significant appropriate changes in such activity will be used.

Significant changes in a given sodium channel activity or in vivo function (discussed below) of at least about 30%-40%, and most preferably, by changes of at least about 50%, with higher values of course being possible. The active compounds of the present invention also may be used for the generation of antibodies which may then be used in analytical and preparatory techniques for detecting and quantifying further such inhibitors.

Proteins are often used in high throughput screening (HTS) assays known in the art, including melanophore assays to investigate receptor ligand interactions, yeast based assay systems and mammalian cell expression systems. For a review see Jayawickreme and Kost, Curr. Opin. Biotechnol. 8: 629 634 (1997). Automated and miniaturized HTS assays are also contemplated as described for example in Houston and Banks Curr. Opin. Biotechnol. 8: 734 740 (1997)

There are a number of different libraries used for the identification of small molecule modulators including chemical libraries, natural product libraries and combinatorial libraries comprised or random or designed peptides, oligonucleotides or organic molecules. Chemical libraries consist of structural analogs of known compounds or compounds that are identified as hits or leads via natural product screening or from screening against a potential therapeutic target. Natural product libraries are collections of products from microorganisms, animals, plants, insects or marine organisms which are used to create mixtures of screening by, e.g., fermentation and extractions of broths from soil, plant or marine organisms. Natural product libraries include polypeptides, non-ribosomal peptides and non-naturally occurring variants thereof. For a review see Science 282:63 68 (1998). Combinatorial libraries are composed of large numbers of peptides oligonucleotides or organic compounds as a mixture. They are relatively simple to prepare by traditional automated synthesis methods, PCR cloning or other synthetic methods. Of particular interest will be libraries that include peptide, protein, peptidomimetic, multiparallel synthetic collection, recombinatorial and polypeptide libraries. A review of combinatorial libraries and libraries created therefrom, see Myers Curr. Opin. Biotechnol. 8: 701 707 (1997). A candidate modulator identified by the use of various libraries described may then be optimized to modulate activity of Nav1.3 splice variant protein through, for example, rational drug design.

It will, of course, be understood that all the screening methods of the present invention are useful in themselves notwithstanding the fact that effective candidates may not be found. The invention provides methods for screening for such candidates, not solely methods of finding them.

c. In Vitro Assays.

Those of skill in the art are aware of numerous variations of in vitro methods for measuring sodium channel activity. Cells that express the given sodium channel being tested e.g., a neuronal cell line (from any eukaroyotic, preferably mammalian source) that has been transformed or transfected with a nucleic acid that encodes a protein of SEQ ID NO:2 or alternatively, a primary mammalian cell culture e.g., neurons that naturally express a protein of SEQ ID NO:2 are obtained. Primary cells from e.g., a rat source can be prepared as taught in Gallo et al., 1990 (J. Neurochem: 54, 1619-25 or Example 155 of U.S. Pat. No. 6,756,400). The cells are plated in an appropriate support e.g., in 96-well poly-D-lysine-coated black wall-clear bottom culture plates at a suitable concentration (e.g., 1-2×10$^5$ cells/well of a 96-well plate). The cells are maintained at 37° C. in an atmosphere containing 5% $CO_2$.

To measure sodium channel activity, veratridine-evoked increases in intracellular $Ca^{2+}$ ([$Ca^{2+}$]i) in fluo-4/AM loaded cerebellar granule neurons may be monitored, in real-time, using a Fluorescent Imaging Plate Reader (FLIPR™, Molecular Devices, Sunnyvale, Calif.). The cells are incubated with 4 mM fluo-4/AM in HBSS buffer containing 2.5 mM probenecid and 0.04% pluronic acid for 45 min at 37° C. The cells are then washed three times with HBSS containing 2.5 mM probenecid (FLIPR™ buffer). The plates are transferred to the FLIPR™ and the cells incubated for 5 min in FLIPR™ buffer, in the absence (control) or presence of the test compound, prior to addition of veratridine (40 μM). Cell fluorescence ($\lambda_{Ex}$=488 nm; $\lambda_{Em}$=510 nm) is monitored both before and after the addition of veratridine. Peak fluorescence intensity, after veratridine addition, is determined using the FLIPR™ software. Curve fitting and parameter estimation (p$IC_{50}$) were performed using GraphPad. Stock solutions (10 mM) of compounds were made in 100% DMSO.

As an alternative to FLIPR™, the VIPR™ (Aurora Biosciences Corporation) assay may be used. In such an alternative assay, HEK293 cells expressing hNav1.3 channels are cultured on 96- or 384-well plates (Costar tissue culture treated 96-well flat bottom plates, Corning). To prevent detachment of cells during plate washing, these plates are pre-coated with 0.5% Growth Factor Reduced matrigel matrix in DMEM for 1 hour at room temperature before use for cell culture. About 40,000 cells are seeded to each well and incubated at 38° C. for 24 hours before assay. Assay is performed at room temperature. The cell plates are first washed three times with bath solution using automatic plate washer (ELx405, Biotek), leaving a residual volume of 50 µL/well. Subsequently, cells are incubated with mixed dye solution for 30 min in the dark at room temperature. The mixed dye solution is prepared with External solution and consists of 10 µM CC2-DMPE (chlorocoumarin-2-dimyristoyl phosphatidylethanolamine), 2.4 µM DISBAC$_6$(3) (bis-(1,3-dihexyl-thiobarbituric acid) trimethine oxonol), 0.5% β-cyclodextrin, 20 µg/ml pluronic F-127 and ESS Acid Yellow 17 (ESS AY-17). Thereafter, the cells are washed three times again with bath solution and then incubated with bath solution containing 0.5 mM ESS AY-17 and test compounds at desired concentrations for 10 min before assay.

A VIPR is equipped with instrumentation capable of electrical stimulation of cells expressing NaV1.3 (see U.S. Pat. No. 6,686,193). This allows manipulation of the membrane potential and modulates the NaV1.3 conductance. Sodium channels have brief (~1-3 ms) open times, so a train of electric field pulses is used to cycle the channel through open and closed conformations repeatedly. Membrane potential changes caused by the sodium influx through the channels is converted to optical signals using the Aurora FRET voltage sensitive dyes, described above. Cells stained with CC2-DMPE and DiSBAC$_6$(3) are excited at 405 nm. The instrument is able to continually monitor the fluorescent output at two wavelengths for FRET measurement. Fluorescence responses are obtained at two wavelengths, 460 nm for CC2-DMPE and 580 nm for DiSBAC$_6$(3).

The IC50 values of the tested compounds may be determined using an assay such as the one set forth above or any other conventional assay that measures sodium channel activity. Compounds that are effective in such in vitro assays may be tested in subsequent in vivo assays as described below.

Such assays are highly amenable to automation and high throughput. High throughput screening of compounds is described in WO 84/03564.

Of particular interest in this format will be the screening of a variety of different Nav1.3 splice variant protein mutants. These mutants, including deletion, truncation, insertion and substitution mutants, will help identify which domains are involved with the functional channel forming activity of the Nav1.3 splice variant of the invention. Once this region(s) or amino acids particularly important to the channel forming properties of the Nav1.3 splice variant protein that has the sequence of SEQ ID NO:2 has been determined, it will be possible to identify which of these mutants have altered structure but retain some or all of the biological functions of the sodium channel. As noted above, SEQ ID NO:2 comprises a 33-amino acid (NVSQASM SSRMVPGLPANGKMHSTVDCNGVVSL; SEQ ID NO:3) that starts at residue 624 of the NAV1.3 splice variant of the present invention. This region is part of the linker between domain 1 and domain 2 of the sodium channel alpha 1 subunit. PICA phosphorylation sites of the sodium channel are located in this region and are close to this splice site. It is particularly contemplated that amino acids in this linker region, and particularly, each of the residues in SEQ ID NO:3 will be mutated to assess the effect of such mutation on the sodium channel activity. For example, each of the amino acids in this domain may be separately switched to an alanine residue and an "alanine scan" performed to determine which of the residues is important in determining activity. In additional embodiments, it is contemplated that each of the amino acids in this domain may be separately switched to another amino acid that is a conservative substitution of the native residue depending on the hyrophobicity, hydrophilicity or other characteristics of the amino acid at a given residue. To this effect, the SIFT (Sorting Intolerant From Tolerant) program is an exemplary program that allows the skilled artisan to predict whether an amino acid substitution affects protein function and can distinguish between functionally neutral and deleterious amino acid changes in mutagenesis studies (Ng and Henikoff, Nucleic Acid. Res. 31(13): 3812-3814, 2003)

Purified Nav1.3 splice variant protein or its binding agent can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the Nav1.3 protein active region to a solid phase.

Other forms of in vitro assays include those in which functional readouts are taken. For example cells in which a Nav1.3 protein polypeptide is expressed can be treated with a candidate substance. In such assays, the substance would be formulated appropriately, given its biochemical nature, and contacted with the cell. Depending on the assay, culture may be required. The cell may then be examined by virtue of a number of different physiologic assays, as discussed above. Alternatively, molecular analysis may be performed in which the cells characteristics are examined. This may involve assays such as those for protein expression, enzyme function, substrate utilization, mRNA expression (including differential display of whole cell or polyA RNA) and others. Yet another assay format that can be contemplated is the use of a binding assay with a suitably labeled ligand that binds to the expressed protein. An example of such an assay would be the displacement by a small molecule of a radiolabeled or fluorescently labeled ligand from the expressed Nav1.3 protein. Such an assay can be used to identify potential small molecule modulators of the channel especially if the site where the labeled ligand binds is known to affect channel activity or regulation.

d. In Vivo Assays.

The present invention also encompasses the use of various animal models. In exemplary embodiments, the in vivo assays are set up to identify agents that modulate the sodium channel and are effective as analgesic or anti-inflammatory agents. The ability of an agent or a combination of agents to treat pain can be determined using known pharmacological models (for example see Kim, S. H. and Chung, J. M., Pain, 1992, 50, 355-363), or using models that are similar to known models. For example, to test baseline pain responses, tests such as mechanical withdrawal frequencies by application of different forces of calibrated von Frey monofilaments (mN: 0.24, 1.47, 4.33, 8.01, 23.69, 40.31) (Stoelting, Wood Dale, Ill.) to the plantar hind paw surface, or thermal withdrawal latencies after the application of radiant heat to the plantar hind paw surface may be used (Mansikka et al., Exp Neurol 162: 343-349, 2000; Tao et al., Neuroscience 98: 201-206, 2000). Mechanical withdrawal frequencies are assessed by applying calibrated von Frey monofilaments 0.24 and 4.33 mN to the plantar hind paw surface (Fairbanks et al., Proc Natl Acad Sci USA 97: 10584-10589 2000; Mansikka et al., Exp Neurol 162: 343-349, 2000).

Male Sprague-Dawley rats are pre-screened to determine their baseline 50% withdrawal threshold using a set of von Frey filaments. The 50% withdrawal threshold for mechanical stimulation to the hind paw is determined by the up-down method described by Dixon W. J., Ann. Rev. Pharmacol. Toxicol., 1980, 20, 441-462. Briefly, 8 von Frey filaments with approximately equal logarithmic incremental (0.22 bending forces are chosen (von Frey numbers: 3.65, 3.87, 4.10, 4.31, 4.52, 4.74, 4.92, and 5.16; equivalent to: 0.45, 0.74, 1.26, 2.04, 3.31, 5.50, 8.32, and 14.45 g). A von Frey filament is applied perpendicularly to the plantar surface with sufficient force to bend it slightly and held for 3-5 seconds. An abrupt withdrawal of the foot during stimulation or immediately after the removal of stimulus is considered a positive response.

Whenever there is a positive or negative response, the next weaker or stronger filament is applied, respectively. The test is continued until six stimuli after the first change in response has been obtained. The pattern of positive and negative responses may then be converted into a 50% threshold value using various formulae known to those of skill in the art. One such formula is: 50% threshold=$10^{(X+kd)}/10^4$, where X=the value of the final von Frey filament used (in log units), k=the tabular value for the pattern of positive/negative responses [obtained from Dixon, *Annu Rev Pharmacol Toxicol* 20:441-462], and d=the mean difference between stimuli in log units (0.22). In the cases where continuous positive or negative responses are observed all the way out to the end of the stimulus spectrum, values of 0.3 g or 15.0 g are assigned, respectively. For $ED_{50}$ calculations, a linear regression is determined for responses one either side of the 50% reversal and then an approximation is determined based upon the value which intersects the 50% point.

Other in vivo methods of testing pain include hotplate analgesia meter determinations. Such hotplate methods evaluate the reaction time of mice (or rats) dropped onto a heated surface and confronted with a heat stimulus applied to their plantar surface. When an analgesic agent is administered to the animals, their reaction time is markedly increased. Such methods may be assessed using e.g., the SDI Hotplate Analgesia Meter (San Diego Instruments, San Diego, Calif., USA).

Treatment of animals with test compounds will involve the administration of the compound, in an appropriate form, to the animal. Administration will be by any route that can be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood, cerebrospinal fluid (CSF) or lymph supply and intratumoral injection.

Determining the effectiveness of a compound in vivo may involve a variety of different criteria. Such criteria include, but are not limited to, survival, reduction of tumor burden or mass, inhibition or prevention of inflammatory response, increased activity level, improvement in immune effector function and improved food intake.

Therapeutic Methods and Pharmaceutical Compositions

The present invention deals with the treatment of diseases that result from the increased activity (or expression) of sodium channel proteins. Compositions that inhibit the expression or overexpression of Nav1.3 protein or block its sodium channel activity will be useful in treating or preventing a disease or condition associated with sodium channel activity.

The phrase "disease or condition associated with sodium channel activity" includes all disease states and/or conditions that are acknowledged now, or that are found in the future, to be associated with the activity of sodium channels. Such disease states include, but are not limited to, pathophysiological disorders, including hypertension, cardiac arrhythmogenesis, angina, insulin-dependent diabetes, non-insulin dependent diabetes mellitus, diabetic neuropathy, seizures, tachycardia, ischemic heart disease, cardiac failure, myocardial infarction, transplant rejection, autoimmune disease, sickle cell anemia, muscular dystrophy, gastrointestinal disease, mental disorder, sleep disorder, anxiety disorder, eating disorder, neurosis, alcoholism, inflammation, multiple sclerosis, cerebrovascular ischemia, CNS diseases, epilepsy, stroke, Parkinson's disease, asthma, incontinence, urinary dysfunction, micturition disorder, irritable bowel syndrome, restenosis, subarachnoid hemorrhage, Alzheimers disease, drug dependence/addiction, schizophrenia, Huntington's chorea, tension-type headache, trigeminal neuralgia, cluster headache, migraine (acute and prophylaxis), inflammatory pain, neuropathic pain and depression.

Nucleic acid sequences, antisense molecules, PNAs, purified protein, antibodies, antagonists or inhibitors directed against Nav1.3 can all be used as pharmaceutical compositions. Delivery of these molecules for therapeutic purposes is further described below. The most appropriate therapy depends on the patient, the specific diagnosis, and the physician who is treating and monitoring the patient's condition.

Where clinical applications are contemplated, it will be necessary to prepare the small molecules, analgesic compounds, viral expression vectors, antibodies, peptides, nucleic acids and other compositions identified by the present invention as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramusclar, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time. A "subject" or "individual" as used herein, is a vertebrate, preferably a mammal, more preferably a human. Mammals include research, farm and sport animals, and pets.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms cart be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetracetic acid; a solubilizing agent, for example, a cyclodextrin; and an antioxidant, for example, sodium metabisulphite, may be included in the formulation. Alternatively, the solution can be freeze dried and then reconstituted with a suitable solvent just prior to administration.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In the clinical setting a "therapeutically effective amount" is an amount sufficient to effect beneficial or desired clinical results. An effective amount can be administered in one or more doses. The term "therapeutically effective amount" refers to an amount sufficient to effect treatment when administered to a patient in need of treatment. The team "treatment" as used herein refers to the treatment of a disease or medical condition in a patient, such as a mammal (particularly a human) which includes: preventing the disease or medical condition from occurring, i.e., prophylactic treatment of a patient; ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient. Thus, in terms of treatment, a "therapeutically effective amount" of the given therapeutic agent is an amount sufficient to palliate, ameliorate, stabilize, reverse, slow or delay the progression of a disease or condition associated with sodium channel activity or otherwise reduce the pathological consequences of such a disease or condition. The effective amount is generally determined by the physician on a case-by-case basis and is within the skill of one in the art. Several factors are typically taken into account when determining, an appropriate dosage. These factors include age, sex and weight of the patient, the condition being treated, the severity of the condition and the form of the antibody being administered.

The therapeutic compositions can also comprise one or more additional agents effective in the treatment of a disease or disorder associated with sodium channel activity. Other compositions which inhibit the expression, activity or function of Nav1.3 protein (e.g., antagonists) also are contemplated for use in such treatment methods. Thus, combination therapy for the treatment of a disease or disorder associated with sodium channel activity is specifically contemplated. In the context of the present invention, it is contemplated that Nav1.3 inhibition therapy could be used similarly in conjunction with other analgesic agents or sodium channel blocker that are used in the treatment of such disorders.

To achieve the appropriate therapeutic outcome using the methods and compositions of the present invention, one would generally administer a first therapeutic agent that is a Nav1.3, inhibitor or blocker as discussed herein and at least one other therapeutic agent (second therapeutic agent). These compositions would be provided in a combined amount effective to produce the desired therapeutic outcome. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second therapeutic agent.

Alternatively, the first therapeutic agent may precede or follow the other agent treatment by intervals ranging from minutes to weeks. In embodiments where the second therapeutic agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Local delivery of the first therapeutic agent (i.e., the inhibitor, stimulator or other agent that decreases or increases the amount or activity of Nav1.3 in the individual) to patients may be a very efficient method for delivering a therapeutically effective gene to counteract a clinical disease. Similarly, the second therapeutic agent may be directed to a particular, affected region of the subject's body. Alternatively, systemic delivery of the first and/or second therapeutic agent may be appropriate in certain circumstances.

The active compound(s) is effective over a wide dosage range and is generally administered in a therapeutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

According to the invention, a compound can be administered in a single daily dose or in multiple doses per day. The treatment regimen may require administration over extended periods of time, for example, for several days or for from one to six weeks.

"Unit dose" is defined as a discrete amount of a therapeutic composition dispersed in a suitable carrier. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient. Suitable doses of sodium channel blockers are in the general range of from 0.01-100 mg/kg/day, preferably 0.1-50 mg/kg/day. For an average 70 kg human, this would amount to 0.7 mg to 7 g per day, or preferably 7 mg to 3.5 g per day. In general, an effective amount of a compound of this invention is a dose between about 0.5 and about 100 mg/kg. A preferred dose is from about 1 to about 60 mg/kg of active compound. A typical daily dose for an adult human is from about 50 mg to about 5 g.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co. Easton Pa. 18042) pp 1435 1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

In a preferred embodiment, the present invention is directed at treatment of human disorder, disease or condition associated with sodium channel activity, or may be alleviated by administering a sodium channel blocker or inhibitor. A variety of different routes of administration are contemplated. For example, a classic and typical therapy will involve direct, injection of a discrete area.

Further Uses of Compositions of the Invention

It is contemplated that in certain diseases or disorders, the Nav1.3 splice variant is overexpressed. In certain embodiments therefore, methods of diagnosing a disorder in which Nav1.3 splice variant is overexpressed or aberrantly expressed are contemplated. Such diagnostic methods of the present invention are achieved through the detection of the Nav1.3 protein or a fragment thereof that is expressed in abundance as compared to normal expression. Such a protein may be detected using antibodies specific for the protein in any of a number of formats commonly used by those of skill in the art for such detection.

In another aspect, the present invention contemplates that an antibody that is immunoreactive with any sodium channel alpha subunit may be immunoreactive with the protein molecule of the present invention. Indeed, antibodies may be generated using the protein of SEQ ID NO:2, which specifically include antibodies that detect the 32-amino acid linker between Domain 1 and Domain 2. Such antibodies include, but are not limited to, polyclonal, monoclonal, chimeric, single chain, Fab fragments and fragments produced by a Fab expression library, bifunctional/bispecific antibodies, humanized antibodies. CDR grafted antibodies, human antibodies and antibodies which include portions of CDR sequences specific for sodium channel protein of the present invention. Means for preparing and characterizing antibodies are well known in the art (see, e.g., Harlow and Lane, ANTIBODIES: A LABORATORY MANUAL, Cold Spring Harbor Laboratory, Cold Spring Harbor, N.Y., 1988). Antibodies specifically immunoreactive to the splice variant that comprises a sequence of SEQ ID NO:2 are particularly preferred.

It is proposed that antibodies specific for sodium channels will be useful in standard immunochemical procedures, such as ELISA and Western blot methods and in immunohistochemical procedures such as tissue staining to determine the distribution of sodium channels.

EXAMPLE(S)

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The present example teaches the characterization and isolation of a novel Nav1.3 cDNA clone isolated from human spinal cord RNA using RT-PCR to amplify the message in three overlapping fragments (experimental details below). The three fragments were then ligated together to create the full-length sequence. The cDNA clone isolated is a novel splice variant that differs from previously reported Nav1.3 cDNAs (see FIG. 1).

The Nav1.3 cDNA of the present invention was used to express human Nav1.3 in cultured cell lines. The Nav1.3-expressing line was used in high-throughput screening to identify antagonists of Nav1.3 and has been used to measure activity against the sodium channel.

The cell line expressing NaV1.3 was created as follows. Human Embryonic Kidney (HEK) cells were chosen as the most suitable host cell line. The cells were transduced by retrovirus. VSV-G pseudotyped retroviral vectors were generated through a three-plasmids co-transfection. After a stable pool of cells were generated from retroviral transduction, the cells were FACS (Fluorescence Activated Cell Sorter) sorted on light scatter, selecting for individual viable cells on 96 well plates. Daughter plates were made from these plates 2 weeks after sorting and were assayed on the EVIPR by the assay described below.

HEK293 cells expressing hNav1.3 channels are cultured on 96- or 384-well plates (Costar tissue culture treated 96-well flat bottom plates, Corning). To prevent detachment of cells during plate washing, these plates are pre-coated with 0.5% Growth Factor Reduced matrigel matrix in DMEM for 1 hour at room temperature before use for cell culture. About 40,000 cells are seeded to each well and incubated at 38° C. for 24 hours before assay. Assay is performed at room temperature. The cell plates are first washed three times with bath solution using automatic plate washer (ELx405, Biotek), leaving a residual volume of 50 µL/well. Subsequently, cells are incubated with mixed dye solution for 30 min in the dark at room temperature. The mixed dye solution is prepared with External solution and consists of 10 µM CC2-DMPE (chlorocoumarin-2-dimyristoyl phosphatidylethanolamine), 2.4 µM DISBAC$_6$(3) (bis-(1,3-dihexyl-thiobarbituric acid) trimethine oxonol), 0.5% β-cyclodextrin, 20 µg/ml pluronic F-127 and ESS Acid Yellow 17 (ESS AY-17). Thereafter, the cells are washed three times again with bath solution and then incubated with bath solution containing 0.5 mM ESS AY-17 and test compounds at desired concentrations for 10 min before assay.

A VIPR is equipped with instrumentation capable of electrical stimulation of cells expressing NaV1.3 (EVIPR U.S. Pat. No. 6,686,193). This allows manipulation of the membrane potential and modulates the NaV1.3 conductance. Sodium channels have brief (~1-3 ms) open times, so a train of electric field pulses is used to cycle the channel through open and closed conformations repeatedly. Membrane potential changes caused by the sodium influx through the channels is converted to optical signals using the Aurora FRET voltage sensitive dyes, described above. Cells stained with CC2-DMPE and DiSBAC$_6$(3) are excited at 405 nm. The instrument is able to continually monitor the fluorescent output at two wavelengths for FRET measurement. Fluorescence responses are obtained at two wavelengths, 460 nm for CC2-DMPE and 580 nm for DiSBAC$_6$(3).

A. Sequence Comparison of Vertex Nav1.3 Clone Against Other Human Nav1.3 sequences FIG. 1 shows a pilup in which the sequence of the present invention (SEQ ID NO:2) was compared with other human clones that were identified by a blast search at NCI. The amino acid at residue 208 is aspartic acid in the sequence identified in the present invention, however in some other sequences analyzed this residue was found to be a serine residue. Amino acid residue 208 is in the S3-S4 linker in Domain 1 of the sodium channel. It is a very short linker and changes here can have a significant effect on sodium channel activation because S4 residues must pivot in response to changes in transmembrane voltage. Variation at this site arises by alternative splicing and insertion of one of two exons that differ only at residue 208; S is found in neonatal brain NaV1.3, while D is found in adult brain. In addition, it was seen that there is an amino acid insert that starts at residue 624 of SEQ ID NO:2. This region is the linker between domain 1 and domain 2. Protein kinase A phosphorylation sites are in this region and are close to this splice site.

B. Cloning of Nav1.3

The nucleotide sequence for a human Nav1.3 cDNA (Genbank accession #AJ251507) was used to establish oligonucleotide primer sequences and RT-PCR strategies for the cloning of a full-length hNav1.3 cDNA. First strand cDNA synthesis (Clontech, Advantage RT-for-PCR, #639505) was carried out using 100 ng of whole brain RNA (Clontech, #636530) with three Nav1.3 specific antisense oligos (X1-26α, X2-22α and X3-29α, 1 µl of 20 µM for each oligonucleotide) in a total of reaction volume of 20 µl at 42° C. for 45 minutes.

An hNav1.3 cDNA was subsequently subcloned in three fragments (A, B and C) overlapping at unique internal restriction sites (Nsi I and Bgl II) using the first-strand cDNA as template and nested PCR. The individual PCR reactions were carried out initially using an outer set of primers (X1-20s+ X1-26α, X2-22s+X2-22α, X3-22s+X3-29α) and the reaction products subsequently used as template with an inner set of oligonucleotide primers (X1-32s+X1-25α, X2-20s+X2-21α, X3-21s+X3-) for further PCR amplification and isolation of the three Nav1.3 overlapping fragments. Restriction sites were inserted into RT-PCR oligonucleotides at the 5' (Xho I) and 3' (Not I) ends. PCR reaction conditions for both the outer and inner set of oligonucleotides was carried out for 15 cycles of 1' at 95° C., 1' at 55° C. and 6' at 72° C. and then another 15 cycles of 1' at 95° C., 1' at 58° C. and 6' at 72° C. Reaction samples were run on 1% agarose gels, the expected molecular weight band sizes were isolated (frag A=1.2 kb, frag B=1.37 kb and frag C=2.45 kb), subsequently blunt-end ligated into the TOPO II vector (Invitrogen) and individual miniprep DNA samples of the fragments were sequenced.

The three fragments were then subcloned in sequence into the vector pLBCX vector, which is derived from the pLNCX vector (Clontech) but replaces the gene for neomycin resistance with one providing resistance blasticidin. The completed expression vector pLBChNav1.3, containing a novel human Nav1.3 splice product, was utilized to generate retroviral supernatants for infection of HEK293 cells. The infected HEK293 cells were selected in 5 ug/ml blasticidin for two weeks and then single cells were FACSorted for isolation of distinct clonal cell lines, which were tested for Nav channel expression using voltage-sensitive optical dyes and electrical stimulation on eVIPR. Clonal lines with the expected depolarizing responses were further subjected to patch clamp recording techniques and pharmacological characterization on eVIPR. Clonal lines were chosen and an eVIPR assay protocol optimized as described above.

| Table of Oligonucleotide Primers: | |
|---|---|
| X1-20s | CTA CAC GTA ATT AAA TGT GC (SEQ ID NO: 9) |
| X1-26α | AAT GGA TCC ATA ACA ATT AAA TTC AC (SEQ ID NO: 10) |
| X1-32s | NNN NNC TCG AGA GGA TGA AAA GAT GGC ACA GGC (SEQ ID NO: 11) |
| X1-25α | GTT TTA CTT TTA ACC ATG CAT CAC (SEQ ID NO: 12) |
| X2-22s | ATT TGC CAA TGT GTT CTT GAT C (SEQ ID NO: 13) |
| X2-22α | TTG TGC TCA ACA ATA CTG TAG C (SEQ ID NO: 14) |
| X2-20s | CTG GGA CTG CTG TGA TGC AT (SEQ ID NO: 15) |
| X2-21α | GAA GAT TCC ACC AGA TCT TCC (SEQ ID NO: 16) |
| X3-22s | AGA AGA CCT GTC AAG TAA GTA C (SEQ ID NO: 17) |
| X3-29α | CA CAA AGA TAA TTC TTT GTT TCT TTT TAC (SEQ ID NO: 18) |
| X3-21s | GAA GAA GGC AAA GGG AAG ATC (SEQ ID NO: 19) |
| X3- | NNN NNG CGG CCG CTT TTT ACT TTT GAT TTT CTC TGA CC (SEQ ID NO: 20) |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. An in vitro method of identifying a modulator of a human sodium channel α-subunit expression or activity, the method comprising the steps of:

i) contacting a cell that expresses a nucleic acid comprising a nucleotide sequence encoding a protein having the amino acid sequence of SEQ ID NO: 2 with a candidate modulator substance;

ii) monitoring the expression or ion channel activity of the protein having the amino acid sequence of SEQ ID NO: 2; and iii) comparing the expression or ion channel activity of the protein having the amino acid sequence of SEQ ID NO: 2 with expression or ion channel activity of the protein having the amino acid sequence of SEQ ID NO: 2 in a cell not exposed to said candidate modulator substance;

wherein an alteration in the expression or ion channel activity of the protein having the amino acid sequence of SEQ ID NO: 2 in a cell exposed to the candidate modulator substance compared to a cell not exposed to the candidate modulator substance indicates that the candidate modulator substance is a modulator of human sodium channel α-subunit expression or activity.

2. The method of claim 1 wherein the candidate modulator substance comprises a small molecule ion channel blocker or inhibitor, an oligonucleotide, an antisense oligonucleotide, a DNA oligonucleotide, an RNA oligonucleotide, or a chimeric oligonucleotide.

3. The method of claim 2, wherein the candidate modulator substance comprises a nucleotide sequence capable of hybridizing with RNA to form an RNA oligonucleotide-RNA duplex.

4. An in vitro method for identifying a compound that modulates the activity of a sodium channel comprising:

i) contacting a cell that expresses a sodium channel comprising a polypeptide comprising the amino acid sequence of SEQ ID NO: 2 with a test compound under conditions that activate sodium channel activity of said sodium channel in the absence of the test compound; and ii) determining whether the cell contacted with the test compound exhibits a modulation in activity of the sodium channel compared to a cell not contacted with the test compound.

5. The method of claim 4, wherein the cell has been genetically engineered to express or overexpress the polypeptide.

6. The method of claim 4, wherein the cell has been genetically engineered by introducing into the cell a nucleic acid having a nucleotide sequence encoding a polypeptide comprising the amino acid sequence set forth in SEQ ID NO: 2.

7. The method of claim 4, wherein the cell has been genetically engineered to upregulate the expression of a nucleic acid encoding a polypeptide comprising the amino acid sequence of SEQ ID NO: 2.

8. The method of claim 7, wherein the upregulated nucleic acid is endogenous to the cell.

9. The method of claim 4, wherein the method comprises determining whether the cell contacted with the test compound exhibits a decrease in sodium channel activity.

* * * * *

SEQUENCE LISTING

<160> NUMBER OF SEQ ID NOS: 20

<210> SEQ ID NO 1
<211> LENGTH: 5952
<212> TYPE: DNA
<213> ORGANISM: Homo sapiens

<400> SEQUENCE: 1
atggcacagg cactgttggt accccagga cctgaaagct tccgccttt tactagagaa      60 tctcttgctg ctatcgaaaa acgtgctgca gaagagaaag ccaagaagcc caaaaaggaa     120

```
caagataatg atgatgagaa caaaccaaag ccaaatagtg acttggaagc tggaaagaac    180
cttccattta tttatggaga cattcctcca gagatggtgt cagagcccct ggaggacctg    240
gatccctact atatcaataa gaaaactttt atagtaatga ataaaggaaa ggcaattttc    300
cgattcagtg ccacctctgc cttgtatatt ttaactccac taaaccctgt taggaaaatt    360
gctatcaaga ttttggtaca ttctttattc agcatgctta tcatgtgcac tattttgacc    420
aactgtgtat ttatgacctt gagcaaccct cctgactgga caaagaatgt agagtacaca    480
ttcactggaa tctataccct tgagtcactt ataaaaatct tggcaagagg ttttgcttta    540
gaagatttta cgtttcttcg tgatccatgg aactggctgg atttcagtgt cattgtgatg    600
gcatatgtga cagagtttgt ggacctgggc aatgtctcag cgttgagaac attcagagtt    660
ctccgagcac tgaaaacaat tcagtcatt ccaggtttaa agaccattgt gggggccctg    720
atccagtcgg taaagaagct tctgatgtg atgatcctga ctgtgttctg tctgagcgtg    780
tttgctctca ttgggctgca gctgttcatg ggcaatctga gaataaaatg tttgcagtgg    840
cccccaagcg attctgcttt tgaaaccaac accacttcct actttaatgg cacaatggat    900
tcaaatggga catttgttaa tgtaacaatg agcacattta ctggaaagga ttacattgga    960
gatgacagtc acttttatgt tttggatggg caaaaagacc ctttactctg tggaaatggc   1020
tcagatgcag gccagtgtcc agaaggatac atctgtgtga aggctggtcg aaaccccaac   1080
tatggctaca aagctttga caccttagc tgggctttcc tgtctctatt tcgactcatg   1140
actcaagact actgggaaaa tctttaccag ttgacattac gtgctgctgg aaaaacatac   1200
atgatatttt ttgtcctggt cattttcttg ggctcatttt atttggtgaa tttgatcctg   1260
gctgtggtgg ccatggccta tgaggagcag aatcaggcca ccttggaaga agcagaacaa   1320
aaagaggccg aatttcagca gatgctcgaa cagcttaaaa agcaacagga agaagctcag   1380
gcagttgcgg cagcatcagc tgcttcaaga gatttcagtg gaataggtgg gttaggagag   1440
ctgttggaaa gttcttcaga agcatcaaag ttgagttcca aaagtgctaa agaatggagg   1500
aaccgaagga agaaaagaag acagagagag caccttgaag gaaacaacaa aggagagaga   1560
gacagctttc ccaaatccga atctgaagac agcgtcaaaa gaagcagctt cctttttctcc   1620 atggatggaa acagactgac cagtgacaaa aaattctgct cccctcatca gtctctcttg   1680
agtatccgtg gctccctgtt ttccccaaga cgcaatagca aaacaagcat tttcagtttc   1740
agaggtcggg caaaggatgt tggatctgaa aatgactttg ctgatgatga acacagcaca   1800
tttgaagaca gcgaaagcag gagagactca ctgtttgtgc cgcacagaca tggagagcga   1860
cgcaacagta acgttagtca ggccagtatg tcatccagga tggtgccagg gcttccagca   1920
aatgggaaga tgcacagcac tgtggattgc aatggtgtgg tttccttggg caccaccaca   1980
gaaacggaag tcagaaagag aaggttaagc tcttaccaga tttcaatgga gatgctggag   2040
gattcctctg gaaggcaaag agccgtgagc atagccagca ttctgaccaa cacaatggaa   2100
gaacttgaag aatctagaca gaaatgtccg ccatgctggt atagatttgc caatgtgttc   2160
ttgatctggg actgctgtga tgcatggtta aaagtaaaac atcttgtgaa tttaattgtt   2220
atggatccat ttgttgatct tgccatcact atttgcattg tcttaaatac cctctttatg   2280
gccatggagc actaccccat gactgagcaa ttcagtagtg tgttgactgt aggaaacctg   2340
gtctttactg ggatttttcac agcagaaatg gttctcaaga tcattgccat ggatccttat   2400
tactatttcc aagaaggctg gaatatcttt gatggaatta ttgtcagcct cagttttaatg   2460 gagcttggtc tgtcaaatgt ggagggattg tctgtactgc gatcattcag actgcttaga   2520
```

```
gttttcaagt tggcaaaatc ctggcccaca ctaaatatgc taattaagat cattggcaat    2580
tctgtggggg ctctaggaaa cctcaccttg gtgttggcca tcatcgtctt catttttgct    2640
gtggtcggca tgcagctctt tggtaagagc tacaaagaat gtgtctgcaa gatcaatgat    2700
gactgtacgc tcccacggtg gcacatgaac gacttcttcc actccttcct gattgtgttc    2760
cgcgtgctgt gtggagagtg gatagagacc atgtgggact gtatggaggt cgctggccaa    2820
accatgtgcc ttattgtttt catgttggtc atggtcattg gaaaccttgt ggttctgaac    2880
ctctttctgg ccttattgtt gagttcattt agctcagaca accttgctgc tactgatgat    2940
gacaatgaaa tgaataatct gcagattgca gtaggaagaa tgcaaaaggg aattgattat    3000
gtgaaaaata agatgcggga gtgtttccaa aaagcctttt ttagaaagcc aaaagttata    3060
gaaatccatg aaggcaataa gatagacagc tgcatgtcca ataatactgg aattgaaata    3120
agcaaagagc ttaattatct tagagatggg aatggaacca ccagtggtgt aggtactgga    3180
agcagtgttg aaaaatacgt aatcgatgaa atgattataa tgtcattcat aaacaacccc    3240
agcctcaccg tcacagtgcc aattgctgtt ggagagtctg actttgaaaa cttaaatact    3300
gaagagttca gcagtgagtc agaactagaa gaaagcaaag agaaattaaa tgcaaccagc    3360
tcatctgaag gaagcacagt tgatgttgtt ctaccccgag aaggtgaaca agctgaaact    3420
gaacccgaag aagaccttaa accggaagct tgttttactg aaggatgtat taaaaagttt    3480
ccattctgtc aagtaagtac agaagaaggc aaagggaaga tctggtggaa tcttcgaaaa    3540
acctgctaca gtattgttga gcacaactgg tttgagactt tcattgtgtt catgatcctt    3600
ctcagtagtg gtgcattggc cttttgaagat atatacattg aacagcgaaa gactatcaaa    3660
accatgctag aatatgctga caaagtcttt acctatatat tcattctgga aatgcttctc    3720 aaatggggttg cttatggatt tcaaacatat ttcactaatg cctggtgctg gctagatttc    3780
ttgatcgttg atgtttcttt ggttagcctg gtagccaatg ctcttggcta ctcagaactc    3840
ggtgccatca aatcattacg gacattaaga gctttaagac ctctaagagc cttatcccgg    3900
tttgaaggca tgagggtggt tgtgaatgct cttgttggag caattccctc tatcatgaat    3960
gtgctgttgg tctgtctcat cttctggttg atctttagca tcatgggtgt gaatttgttt    4020
gctggcaagt tctaccactg tgttaacatg acaacgggta acatgtttga cattagtgat    4080
gttaacaatt tgagtgactg tcaggctctt ggcaagcaag ctcggtgaaa aacgtgaaa    4140 gtaaactttg ataatgttgg cgctggctat cttgcactgc ttcaagtggc cacatttaaa    4200
ggctggatga atattatgta tgcagctgtt gattcacgag atgttaaact tcagcctgta    4260
tatgaagaaa atctgtacat gtatttatac tttgtcatct ttatcatctt tgggtcattc    4320
ttcactctga atctattcat tggtgtcatc atagataact caaccagca gaaaagaag    4380 tttggaggtc aagacatctt tatgacagag gaacagaaaa aatattacaa tgcaatgaag    4440
aaacttggat ccaagaaacc tcagaaaccc atacctcgcc cagcaaacaa attccaagga    4500
atggtctttg attttgtaac cagacaagtc tttgatatca gcatcatgat cctcatctgc    4560
ctcaacatgg tcaccatgat ggtggaaacg gatgaccagg gcaaatacat gacccctagtt   4620 ttgtcccgga tcaacctagt gttcattgtt ctgttcactg gagaatttgt gctgaagctc    4680
gtctccctca gacactacta cttcactata ggctggaaca tctttgactt tgtggtggtg    4740
attctctcca ttgtaggtat gtttctggct gagatgatag aaaagtattt tgtgtcccct    4800 acctgttcc gagtgatccg tcttgccagg attggccgaa tcctacgtct gatcaaagga    4860
gcaaagggga tccgcacgct gctctttgct ttgatgatgt cccttcctgc gttgtttaac    4920
```

```
atcggcctcc tgctcttcct ggtcatgttt atctatgcca tctttgggat gtccaacttt   4980
gcctatgtta aaaggaagc tggaattgat gacatgttca actttgagac ctttggcaac   5040
agcatgatct gcttgttcca aattacaacc tctgctggct gggatggatt gctagcacct   5100
attcttaata gtgcaccacc cgactgtgac cctgacacaa ttcaccctgg cagctcagtt   5160
aagggagact gtgggaaccc atctgttggg attttctttt ttgtcagtta catcatcata   5220
tccttcctgg ttgtggtgaa catgtacatc gcggtcatcc tggagaactt cagtgttgct   5280
actgaagaaa gtgcagagcc cctgagtgag gatgactttg agatgttcta tgaggtttgg   5340
gaaaagtttg atcccgatgc gacccagttt atagagttct ctaaactctc tgattttgca   5400
gctgccctgg atcctcctct tctcatagca aacccaaca aagtccagct tattgccatg   5460
gatctgccca tggtcagtgg tgaccggatc cactgtcttg atattttatt tgcctttaca   5520
aagcgtgttt tgggtgagag tggagagatg gatgcccttc gaatacagat ggaagacagg   5580
tttatggcat caaaccccctc caaagtctct tatgagccta ttacaaccac tttgaaacgt   5640
aaacaagagg aggtgtctgc cgctatcatt cagcgtaatt tcagatgtta tcttttaaag   5700
caaaggttaa aaaatatatc aagtaactat aacaagagg caattaaagg gaggattgac   5760
ttacctataa aacaagacat gattattgac aaactaaatg ggaactccac tccagaaaaa   5820
acagatggga gttcctctac cacctctcct ccttcctatg atagtgtaac aaaaccagac   5880
aaggaaaagt ttgagaaaga caaaccagaa aaagaaagca aaggaaaaga ggtcagagaa   5940
aatcaaaagt aa                                                      5952

<210> SEQ ID NO 2
<211> LENGTH: 1983
<212> TYPE: PRT
<213> ORGANISM: Homo sapiens

<400> SEQUENCE: 2

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Met Asn Lys Gly
                85                  90                  95

Lys Ala Ile Phe Arg Phe Ser Ala Thr Ser Ala Leu Tyr Ile Leu Thr
            100                 105                 110

Pro Leu Asn Pro Val Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190
```

```
Leu Asp Phe Ser Val Ile Val Met Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
        275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
        355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Glu Gln Asn Gln
            420                 425                 430

Ala Thr Leu Glu Glu Ala Glu Gln Lys Glu Ala Glu Phe Gln Gln Met
        435                 440                 445

Leu Glu Gln Leu Lys Lys Gln Gln Glu Glu Ala Gln Ala Val Ala Ala
    450                 455                 460

Ala Ser Ala Ala Ser Arg Asp Phe Ser Gly Ile Gly Gly Leu Gly Glu
465                 470                 475                 480

Leu Leu Glu Ser Ser Ser Glu Ala Ser Lys Leu Ser Ser Lys Ser Ala
                485                 490                 495

Lys Glu Trp Arg Asn Arg Arg Lys Lys Arg Arg Gln Arg Glu His Leu
            500                 505                 510

Glu Gly Asn Asn Lys Gly Glu Arg Asp Ser Phe Pro Lys Ser Glu Ser
        515                 520                 525

Glu Asp Ser Val Lys Arg Ser Ser Phe Leu Phe Ser Met Asp Gly Asn
    530                 535                 540

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Arg Asn Ser Lys Thr Ser
                565                 570                 575

Ile Phe Ser Phe Arg Gly Arg Ala Lys Asp Val Gly Ser Glu Asn Asp
            580                 585                 590

Phe Ala Asp Asp Glu His Ser Thr Phe Glu Asp Ser Glu Ser Arg Arg
        595                 600                 605

Asp Ser Leu Phe Val Pro His Arg His Gly Glu Arg Arg Asn Ser Asn
    610                 615                 620
```

```
Val Ser Gln Ala Ser Met Ser Ser Arg Met Val Pro Gly Leu Pro Ala
625                 630                 635                 640

Asn Gly Lys Met His Ser Thr Val Asp Cys Asn Gly Val Val Ser Leu
            645                 650                 655

Gly Thr Thr Thr Glu Thr Glu Val Arg Lys Arg Arg Leu Ser Ser Tyr
                660                 665                 670

Gln Ile Ser Met Glu Met Leu Glu Asp Ser Ser Gly Arg Gln Arg Ala
        675                 680                 685

Val Ser Ile Ala Ser Ile Leu Thr Asn Thr Met Glu Glu Leu Glu Glu
690                 695                 700

Ser Arg Gln Lys Cys Pro Pro Cys Trp Tyr Arg Phe Ala Asn Val Phe
705                 710                 715                 720

Leu Ile Trp Asp Cys Cys Asp Ala Trp Leu Lys Val Lys His Leu Val
                725                 730                 735

Asn Leu Ile Val Met Asp Pro Phe Val Asp Leu Ala Ile Thr Ile Cys
                740                 745                 750

Ile Val Leu Asn Thr Leu Phe Met Ala Met Glu His Tyr Pro Met Thr
            755                 760                 765

Glu Gln Phe Ser Ser Val Leu Thr Val Gly Asn Leu Val Phe Thr Gly
            770                 775                 780

Ile Phe Thr Ala Glu Met Val Leu Lys Ile Ile Ala Met Asp Pro Tyr
785                 790                 795                 800

Tyr Tyr Phe Gln Glu Gly Trp Asn Ile Phe Asp Gly Ile Ile Val Ser
                805                 810                 815

Leu Ser Leu Met Glu Leu Gly Leu Ser Asn Val Glu Gly Leu Ser Val
                820                 825                 830

Leu Arg Ser Phe Arg Leu Leu Arg Val Phe Lys Leu Ala Lys Ser Trp
            835                 840                 845

Pro Thr Leu Asn Met Leu Ile Lys Ile Ile Gly Asn Ser Val Gly Ala
850                 855                 860

Leu Gly Asn Leu Thr Leu Val Leu Ala Ile Ile Val Phe Ile Phe Ala
865                 870                 875                 880

Val Val Gly Met Gln Leu Phe Gly Lys Ser Tyr Lys Glu Cys Val Cys
                885                 890                 895

Lys Ile Asn Asp Asp Cys Thr Leu Pro Arg Trp His Met Asn Asp Phe
                900                 905                 910

Phe His Ser Phe Leu Ile Val Phe Arg Val Leu Cys Gly Glu Trp Ile
            915                 920                 925

Glu Thr Met Trp Asp Cys Met Glu Val Ala Gly Gln Thr Met Cys Leu
            930                 935                 940

Ile Val Phe Met Leu Val Met Val Ile Gly Asn Leu Val Val Leu Asn
945                 950                 955                 960

Leu Phe Leu Ala Leu Leu Leu Ser Ser Phe Ser Ser Asp Asn Leu Ala
                965                 970                 975

Ala Thr Asp Asp Asp Asn Glu Met Asn Asn Leu Gln Ile Ala Val Gly
            980                 985                 990

Arg Met Gln Lys Gly Ile Asp Tyr Val Lys Asn Lys Met Arg Glu Cys
            995                 1000                1005

Phe Gln Lys Ala Phe Phe Arg Lys Pro Lys Val Ile Glu Ile His
        1010                1015                1020

Glu Gly Asn Lys Ile Asp Ser Cys Met Ser Asn Asn Thr Gly Ile
        1025                1030                1035

Glu Ile Ser Lys Glu Leu Asn Tyr Leu Arg Asp Gly Asn Gly Thr
```

-continued

```
             1040              1045              1050
Thr Ser  Gly Val Gly Thr Gly  Ser Ser Val Glu  Lys Tyr Val Ile
    1055              1060              1065
Asp Glu  Asn Asp Tyr Met Ser  Phe Ile Asn Asn  Pro Ser Leu Thr
    1070              1075              1080
Val Thr  Val Pro Ile Ala Val  Gly Glu Ser Asp  Phe Glu Asn Leu
    1085              1090              1095
Asn Thr  Glu Glu Phe Ser Ser  Glu Ser Glu Leu  Glu Glu Ser Lys
    1100              1105              1110
Glu Lys  Leu Asn Ala Thr Ser  Ser Ser Glu Gly  Ser Thr Val Asp
    1115              1120              1125
Val Val  Leu Pro Arg Glu Gly  Glu Gln Ala Glu  Thr Glu Pro Glu
    1130              1135              1140
Glu Asp  Leu Lys Pro Glu Ala  Cys Phe Thr Glu  Gly Cys Ile Lys
    1145              1150              1155
Lys Phe  Pro Phe Cys Gln Val  Ser Thr Glu Glu  Gly Lys Gly Lys
    1160              1165              1170
Ile Trp  Trp Asn Leu Arg Lys  Thr Cys Tyr Ser  Ile Val Glu His
    1175              1180              1185
Asn Trp  Phe Glu Thr Phe Ile  Val Phe Met Ile  Leu Leu Ser Ser
    1190              1195              1200
Gly Ala  Leu Ala Phe Glu Asp  Ile Tyr Ile Glu  Gln Arg Lys Thr
    1205              1210              1215
Ile Lys  Thr Met Leu Glu Tyr  Ala Asp Lys Val  Phe Thr Tyr Ile
    1220              1225              1230
Phe Ile  Leu Glu Met Leu Leu  Lys Trp Val Ala  Tyr Gly Phe Gln
    1235              1240              1245
Thr Tyr  Phe Thr Asn Ala Trp  Cys Trp Leu Asp  Phe Leu Ile Val
    1250              1255              1260
Asp Val  Ser Leu Val Ser Leu  Val Ala Asn Ala  Leu Gly Tyr Ser
    1265              1270              1275
Glu Leu  Gly Ala Ile Lys Ser  Leu Arg Thr Leu  Arg Ala Leu Arg
    1280              1285              1290
Pro Leu  Arg Ala Leu Ser Arg  Phe Glu Gly Met  Arg Val Val Val
    1295              1300              1305
Asn Ala  Leu Val Gly Ala Ile  Pro Ser Ile Met  Asn Val Leu Leu
    1310              1315              1320
Val Cys  Leu Ile Phe Trp Leu  Ile Phe Ser Ile  Met Gly Val Asn
    1325              1330              1335
Leu Phe  Ala Gly Lys Phe Tyr  His Cys Val Asn  Met Thr Thr Gly
    1340              1345              1350
Asn Met  Phe Asp Ile Ser Asp  Val Asn Asn Leu  Ser Asp Cys Gln
    1355              1360              1365
Ala Leu  Gly Lys Gln Ala Arg  Trp Lys Asn Val  Lys Val Asn Phe
    1370              1375              1380
Asp Asn  Val Gly Ala Gly Tyr  Leu Ala Leu Leu  Gln Val Ala Thr
    1385              1390              1395
Phe Lys  Gly Trp Met Asp Ile  Met Tyr Ala Ala  Val Asp Ser Arg
    1400              1405              1410
Asp Val  Lys Leu Gln Pro Val  Tyr Glu Glu Asn  Leu Tyr Met Tyr
    1415              1420              1425
Leu Tyr  Phe Val Ile Phe Ile  Ile Phe Gly Ser  Phe Phe Thr Leu
    1430              1435              1440
```

-continued

```
Asn Leu Phe Ile Gly Val Ile Ile Asp Asn Phe Asn Gln Gln Lys
    1445                1450                1455
Lys Lys Phe Gly Gly Gln Asp Ile Phe Met Thr Glu Glu Gln Lys
    1460                1465                1470
Lys Tyr Tyr Asn Ala Met Lys Lys Leu Gly Ser Lys Lys Pro Gln
    1475                1480                1485
Lys Pro Ile Pro Arg Pro Ala Asn Lys Phe Gln Gly Met Val Phe
    1490                1495                1500
Asp Phe Val Thr Arg Gln Val Phe Asp Ile Ser Ile Met Ile Leu
    1505                1510                1515
Ile Cys Leu Asn Met Val Thr Met Met Val Glu Thr Asp Asp Gln
    1520                1525                1530
Gly Lys Tyr Met Thr Leu Val Leu Ser Arg Ile Asn Leu Val Phe
    1535                1540                1545
Ile Val Leu Phe Thr Gly Glu Phe Val Leu Lys Leu Val Ser Leu
    1550                1555                1560
Arg His Tyr Tyr Phe Thr Ile Gly Trp Asn Ile Phe Asp Phe Val
    1565                1570                1575
Val Val Ile Leu Ser Ile Val Gly Met Phe Leu Ala Glu Met Ile
    1580                1585                1590
Glu Lys Tyr Phe Val Ser Pro Thr Leu Phe Arg Val Ile Arg Leu
    1595                1600                1605
Ala Arg Ile Gly Arg Ile Leu Arg Leu Ile Lys Gly Ala Lys Gly
    1610                1615                1620
Ile Arg Thr Leu Leu Phe Ala Leu Met Met Ser Leu Pro Ala Leu
    1625                1630                1635
Phe Asn Ile Gly Leu Leu Leu Phe Leu Val Met Phe Ile Tyr Ala
    1640                1645                1650
Ile Phe Gly Met Ser Asn Phe Ala Tyr Val Lys Lys Glu Ala Gly
    1655                1660                1665
Ile Asp Asp Met Phe Asn Phe Glu Thr Phe Gly Asn Ser Met Ile
    1670                1675                1680
Cys Leu Phe Gln Ile Thr Thr Ser Ala Gly Trp Asp Gly Leu Leu
    1685                1690                1695
Ala Pro Ile Leu Asn Ser Ala Pro Pro Asp Cys Asp Pro Asp Thr
    1700                1705                1710
Ile His Pro Gly Ser Ser Val Lys Gly Asp Cys Gly Asn Pro Ser
    1715                1720                1725
Val Gly Ile Phe Phe Phe Val Ser Tyr Ile Ile Ile Ser Phe Leu
    1730                1735                1740
Val Val Val Asn Met Tyr Ile Ala Val Ile Leu Glu Asn Phe Ser
    1745                1750                1755
Val Ala Thr Glu Glu Ser Ala Glu Pro Leu Ser Glu Asp Asp Phe
    1760                1765                1770
Glu Met Phe Tyr Glu Val Trp Glu Lys Phe Asp Pro Asp Ala Thr
    1775                1780                1785
Gln Phe Ile Glu Phe Ser Lys Leu Ser Asp Phe Ala Ala Ala Leu
    1790                1795                1800
Asp Pro Pro Leu Leu Ile Ala Lys Pro Asn Lys Val Gln Leu Ile
    1805                1810                1815
Ala Met Asp Leu Pro Met Val Ser Gly Asp Arg Ile His Cys Leu
    1820                1825                1830
Asp Ile Leu Phe Ala Phe Thr Lys Arg Val Leu Gly Glu Ser Gly
    1835                1840                1845
```

```
Glu Met Asp Ala Leu Arg Ile Gln Met Glu Asp Arg Phe Met Ala
    1850                1855                1860

Ser Asn Pro Ser Lys Val Ser Tyr Glu Pro Ile Thr Thr Thr Leu
    1865                1870                1875

Lys Arg Lys Gln Glu Glu Val Ser Ala Ala Ile Ile Gln Arg Asn
    1880                1885                1890

Phe Arg Cys Tyr Leu Leu Lys Gln Arg Leu Lys Asn Ile Ser Ser
    1895                1900                1905

Asn Tyr Asn Lys Glu Ala Ile Lys Gly Arg Ile Asp Leu Pro Ile
    1910                1915                1920

Lys Gln Asp Met Ile Ile Asp Lys Leu Asn Gly Asn Ser Thr Pro
    1925                1930                1935

Glu Lys Thr Asp Gly Ser Ser Ser Thr Thr Ser Pro Pro Ser Tyr
    1940                1945                1950

Asp Ser Val Thr Lys Pro Asp Lys Glu Lys Phe Glu Lys Asp Lys
    1955                1960                1965

Pro Glu Lys Glu Ser Lys Gly Lys Glu Val Arg Glu Asn Gln Lys
    1970                1975                1980

<210> SEQ ID NO 3
<211> LENGTH: 33
<212> TYPE: PRT
<213> ORGANISM: Homo sapiens

<400> SEQUENCE: 3

Asn Val Ser Gln Ala Ser Met Ser Ser Arg Met Val Pro Gly Leu Pro
1               5                   10                  15

Ala Asn Gly Lys Met His Ser Thr Val Asp Cys Asn Gly Val Val Ser
                20                  25                  30

Leu

<210> SEQ ID NO 4
<211> LENGTH: 1366
<212> TYPE: PRT
<213> ORGANISM: Homo sapiens

<400> SEQUENCE: 4

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
                20                  25                  30

Lys Ala Lys Lys Pro Lys Lys Glu Gln Asp Asn Asp Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Met Asn Lys Gly
                85                  90                  95

Lys Ala Ile Phe Arg Phe Ser Ala Thr Ser Ala Leu Tyr Ile Leu Thr
            100                 105                 110

Pro Leu Asn Pro Val Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
```

-continued

```
            145                 150                 155                 160
Phe Thr Gly Ile Tyr Thr Phe Glu Ser Leu Ile Lys Ile Leu Val Arg
                    165                 170                 175
Gly Phe Cys Leu Glu Asp Phe Thr Phe Leu Arg Asp Pro Trp Asn Trp
                180                 185                 190
Leu Asp Phe Ser Val Ile Val Met Ala Tyr Val Thr Glu Phe Val Asp
            195                 200                 205
Leu Gly Asn Val Ser Ala Leu Arg Thr Phe Arg Val Leu Arg Ala Leu
        210                 215                 220
Lys Thr Ile Ser Val Ile Pro Gly Leu Lys Thr Ile Val Gly Ala Leu
225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Leu Gln Trp Pro Pro Ser Asp Ser Ala Phe Glu
        275                 280                 285
Thr Asn Thr Thr Ser Tyr Phe Asn Gly Thr Met Asp Ser Asn Gly Thr
    290                 295                 300
Phe Val Asn Val Thr Met Ser Thr Phe Asn Trp Lys Asp Asn Ile Gly
305                 310                 315                 320
Asp Asp Ser His Phe Tyr Val Leu Asp Gly Gln Lys Asp Pro Leu Leu
                325                 330                 335
Cys Gly Asn Gly Ser Asp Ala Gly Gln Cys Pro Glu Gly Tyr Ile Cys
            340                 345                 350
Val Lys Ala Gly Arg Asn Pro Asn Tyr Gly Tyr Thr Ser Phe Asp Thr
        355                 360                 365
Phe Ser Trp Ala Phe Leu Ser Leu Phe Arg Leu Met Thr Gln Asp Tyr
    370                 375                 380
Trp Glu Asn Leu Tyr Gln Leu Thr Leu Arg Ala Ala Gly Lys Thr Tyr
385                 390                 395                 400
Thr Ile Phe Phe Val Leu Val Ile Phe Leu Gly Ser Phe Tyr Leu Val
                405                 410                 415
Asn Leu Ile Leu Ala Val Val Ala Met Ala Tyr Glu Glu Gln Asn Gln
            420                 425                 430
Ala Thr Leu Glu Glu Ala Glu Gln Lys Glu Ala Glu Phe Gln Gln Met
        435                 440                 445
Leu Glu Gln Leu Lys Lys Gln Gln Glu Glu Ala Gln Ala Val Ala Ala
    450                 455                 460
Ala Ser Ala Ala Ser Arg Asp Phe Ser Gly Ile Gly Gly Leu Gly Glu
465                 470                 475                 480
Leu Leu Glu Ser Ser Ser Glu Ala Ser Lys Leu Ser Ser Lys Ser Ala
                485                 490                 495
Lys Glu Trp Arg Asn Arg Arg Lys Arg Arg Gln Arg Glu His Leu
            500                 505                 510
Glu Gly Asn Asn Lys Gly Glu Arg Asp Ser Phe Pro Lys Ser Glu Ser
        515                 520                 525
Glu Asp Ser Val Lys Arg Ser Ser Phe Leu Phe Ser Met Asp Gly Asn
    530                 535                 540
Arg Leu Thr Ser Asp Lys Lys Phe Cys Ser Pro His Gln Ser Leu Leu
545                 550                 555                 560
Ser Ile Arg Gly Ser Leu Phe Ser Pro Arg Arg Asn Ser Lys Thr Ser
                565                 570                 575
```

-continued

```
Ile Phe Ser Phe Arg Gly Arg Ala Lys Asp Val Gly Ser Glu Asn Asp
            580                 585                 590

Phe Ala Asp Asp Glu His Ser Thr Phe Glu Asp Ser Glu Thr Arg Arg
            595                 600                 605

Asp Ser Leu Phe Glu Pro His Arg His Gly Glu Arg Arg Asn Ser Asn
            610                 615                 620

Gly Thr Thr Thr Glu Thr Glu Val Arg Lys Arg Leu Ser Ser Tyr
625                 630                 635                 640

Gln Ile Ser Met Glu Met Leu Glu Asp Ser Ser Gly Arg Gln Arg Ala
                    645                 650                 655

Val Ser Ile Ala Ser Ile Leu Thr Asn Thr Met Glu Glu Leu Glu Glu
                    660                 665                 670

Ser Arg Gln Lys Cys Pro Pro Cys Trp Tyr Arg Phe Ala Asn Val Phe
                    675                 680                 685

Leu Ile Trp Asp Cys Cys Asp Ala Trp Leu Lys Val Lys His Leu Val
            690                 695                 700

Asn Leu Ile Val Met Asp Pro Phe Val Asp Leu Ala Ile Thr Ile Cys
705                 710                 715                 720

Ile Val Leu Asn Thr Leu Phe Met Ala Met Glu His Tyr Pro Met Thr
                    725                 730                 735

Glu Gln Phe Ser Ser Val Leu Thr Val Gly Asn Leu Val Phe Thr Gly
            740                 745                 750

Ile Phe Thr Ala Glu Met Val Leu Lys Ile Ile Ala Met Asp Pro Tyr
            755                 760                 765

Tyr Tyr Phe Gln Glu Gly Trp Asn Ile Phe Asp Gly Ile Ile Val Ser
770                 775                 780

Leu Ser Leu Met Glu Leu Gly Leu Ser Asn Val Glu Gly Leu Ser Val
785                 790                 795                 800

Leu Arg Ser Phe Arg Leu Leu Arg Val Phe Lys Leu Ala Lys Ser Trp
            805                 810                 815

Pro Thr Leu Asn Met Leu Ile Lys Ile Ile Gly Asn Ser Val Gly Ala
            820                 825                 830

Leu Gly Asn Leu Thr Leu Val Leu Ala Ile Ile Val Phe Ile Phe Ala
            835                 840                 845

Val Val Gly Met Gln Leu Phe Gly Lys Ser Tyr Lys Glu Cys Val Cys
850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                    885                 890                 895

Glu Thr Met Trp Asp Cys Met Glu Val Ala Gly Gln Thr Met Cys Leu
            900                 905                 910

Ile Val Phe Met Leu Val Met Val Ile Gly Asn Leu Val Val Leu Asn
            915                 920                 925

Leu Phe Leu Ala Leu Leu Leu Ser Ser Phe Ser Ser Asp Asn Leu Ala
            930                 935                 940

Ala Thr Asp Asp Asp Asn Glu Met Asn Asn Leu Gln Ile Ala Val Gly
945                 950                 955                 960

Arg Met Gln Lys Gly Ile Asp Tyr Val Lys Asn Lys Met Arg Glu Cys
                    965                 970                 975

Phe Gln Lys Ala Phe Phe Arg Lys Pro Lys Val Ile Glu Ile His Glu
            980                 985                 990

Gly Asn Lys Ile Asp Ser Cys Met Ser Asn Asn Thr Gly Ile Glu Ile
            995                 1000                1005
```

-continued

| | | | | | | | | | | | |
|---|---|---|---|---|---|---|---|---|---|---|---|
|Ser|Lys 1010|Ala|Leu|Asn|Tyr 1015|Leu|Arg|Asp|Gly|Asn 1020|Gly Thr Thr Ser|

Ser Lys Ala Leu Asn Tyr Leu Arg Asp Gly Asn Gly Thr Thr Ser
    1010                1015                1020

Gly Val Gly Thr Gly Ser Ser Val Glu Lys Tyr Val Ile Asp Glu
    1025                1030                1035

Asn Asp Tyr Met Ser Phe Ile Asn Asn Pro Ser Leu Thr Val Thr
    1040                1045                1050

Val Pro Ile Ala Val Gly Glu Ser Asp Phe Glu Asn Leu Asn Thr
    1055                1060                1065

Glu Glu Phe Ser Ser Glu Ser Glu Leu Glu Ser Lys Glu Lys
    1070                1075                1080

Leu Asn Ala Thr Ser Ser Ser Glu Gly Ser Thr Val Asp Val Val
    1085                1090                1095

Leu Pro Arg Glu Gly Glu Gln Ala Glu Thr Glu Pro Glu Glu Asp
    1100                1105                1110

Leu Lys Pro Glu Ala Cys Phe Thr Glu Gly Cys Ile Lys Lys Phe
    1115                1120                1125

Pro Phe Cys Gln Val Ser Thr Glu Glu Gly Lys Gly Lys Ile Trp
    1130                1135                1140

Trp Asn Leu Arg Lys Thr Cys Tyr Ser Ile Val Glu His Asn Trp
    1145                1150                1155

Phe Glu Thr Phe Ile Val Phe Met Ile Leu Leu Ser Ser Gly Ala
    1160                1165                1170

Leu Ala Phe Glu Asp Ile Tyr Ile Glu Gln Arg Lys Thr Ile Lys
    1175                1180                1185

Thr Met Leu Glu Tyr Ala Asp Lys Val Phe Thr Tyr Ile Phe Ile
    1190                1195                1200

Leu Glu Met Leu Leu Lys Trp Val Ala Tyr Gly Phe Gln Thr Tyr
    1205                1210                1215

Phe Thr Asn Ala Trp Cys Arg Leu Asp Phe Leu Ile Val Asp Val
    1220                1225                1230

Ser Leu Val Ser Leu Val Ala Asn Ala Leu Gly Tyr Ser Glu Leu
    1235                1240                1245

Gly Ala Ile Lys Ser Leu Arg Thr Leu Arg Ala Leu Arg Pro Leu
    1250                1255                1260

Arg Ala Leu Ser Arg Phe Glu Gly Met Arg Val Val Val Asn Ala
    1265                1270                1275

Leu Val Gly Ala Ile Pro Ser Ile Met Asn Val Leu Leu Val Cys
    1280                1285                1290

Leu Ile Phe Trp Leu Ile Phe Ser Ile Met Gly Val Asn Leu Phe
    1295                1300                1305

Ala Gly Lys Phe Tyr His Cys Val Asn Met Thr Thr Gly Asn Met
    1310                1315                1320

Phe Asp Ile Ser Asp Val Asn Asn Leu Ser Asp Cys Gln Ala Leu
    1325                1330                1335

Gly Lys Gln Ala Arg Trp Lys Asn Val Lys Val Asn Phe Asp Asn
    1340                1345                1350

Val Gly Ala Gly Tyr Leu Ala Leu Leu Gln Val Val Ser
    1355                1360                1365

<210> SEQ ID NO 5
<211> LENGTH: 1951
<212> TYPE: PRT
<213> ORGANISM: Homo sapiens

<400> SEQUENCE: 5

```
Met Ala Gln Ala Leu Leu Val Pro Pro Gly Pro Glu Ser Phe Arg Leu
  1               5                  10                  15

Phe Thr Arg Glu Ser Leu Ala Ala Ile Glu Lys Arg Ala Ala Glu Glu
             20                  25                  30

Lys Ala Lys Lys Pro Lys Lys Glu Gln Asp Asn Asp Glu Asn Lys
         35                  40                  45

Pro Lys Pro Asn Ser Asp Leu Glu Ala Gly Lys Asn Leu Pro Phe Ile
 50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Met Asn Lys Gly
                 85                  90                  95

Lys Ala Ile Phe Arg Phe Ser Ala Thr Ser Ala Leu Tyr Ile Leu Thr
                100                 105                 110

Pro Leu Asn Pro Val Arg Lys Ile Ala Ile Lys Ile Leu Val His Ser
             115                 120                 125

Leu Phe Ser Met Leu Ile Met Cys Thr Ile Leu Thr Asn Cys Val Phe
         130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                 165                 170                 175

Gly Phe Cys Leu Glu Asp Phe Thr Phe Leu Arg Asp Pro Trp Asn Trp
             180                 185                 190

Leu Asp Phe Ser Val Ile Val Met Ala Tyr Val Thr Glu Phe Val Ser
         195                 200                 205

Leu Gly Asn Val Ser Ala Leu Arg Thr Phe Arg Val Leu Arg Ala Leu
         210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                 245                 250                 255

Cys Leu Ser Val Phe Ala Leu Ile Gly Leu Gln Leu Phe Met Gly Asn
             260                 265                 270

Leu Arg Asn Lys Cys Leu Gln Trp Pro Pro Ser Asp Ser Ala Phe Glu
         275                 280                 285

Thr Asn Thr Thr Ser Tyr Phe Asn Gly Thr Met Asp Ser Asn Gly Thr
         290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                 325                 330                 335

Cys Gly Asn Gly Ser Asp Ala Gly Gln Cys Pro Glu Gly Tyr Ile Cys
             340                 345                 350

Val Lys Ala Gly Arg Asn Pro Asn Tyr Gly Tyr Thr Ser Phe Asp Thr
         355                 360                 365

Phe Ser Trp Ala Phe Leu Ser Leu Phe Arg Leu Met Thr Gln Asp Tyr
         370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                 405                 410                 415

Asn Leu Ile Leu Ala Val Val Ala Met Ala Tyr Glu Glu Gln Asn Gln
```

```
                420             425             430
Ala Thr Leu Glu Glu Ala Glu Gln Lys Glu Ala Glu Phe Gln Gln Met
            435                 440                 445
Leu Glu Gln Leu Lys Lys Gln Gln Glu Glu Ala Gln Ala Val Ala Ala
        450                 455                 460
Ala Ser Ala Ala Ser Arg Asp Phe Ser Gly Ile Gly Gly Leu Gly Glu
465                 470                 475                 480
Leu Leu Glu Ser Ser Glu Ala Ser Lys Leu Ser Ser Lys Ser Ala
                485                 490                 495
Lys Glu Trp Arg Asn Arg Arg Lys Arg Arg Gln Arg Glu His Leu
            500                 505                 510
Glu Gly Asn Asn Lys Gly Glu Arg Asp Ser Phe Pro Lys Ser Glu Ser
            515                 520                 525
Glu Asp Ser Val Lys Arg Ser Ser Phe Leu Phe Ser Met Asp Gly Asn
            530                 535                 540
Arg Leu Thr Ser Asp Lys Lys Phe Cys Ser Pro His Gln Ser Leu Leu
545                 550                 555                 560
Ser Ile Arg Gly Ser Leu Phe Ser Pro Arg Arg Asn Ser Lys Thr Ser
                565                 570                 575
Ile Phe Ser Phe Arg Gly Arg Ala Lys Asp Val Gly Ser Glu Asn Asp
            580                 585                 590
Phe Ala Asp Asp Glu His Ser Thr Phe Glu Asp Ser Glu Ser Arg Arg
            595                 600                 605
Asp Ser Leu Phe Val Pro His Arg His Gly Glu Arg Arg Asn Ser Asn
            610                 615                 620
Gly Thr Thr Thr Glu Thr Glu Val Arg Lys Arg Arg Leu Ser Ser Tyr
625                 630                 635                 640
Gln Ile Ser Met Glu Met Leu Glu Asp Ser Ser Gly Arg Gln Arg Ala
                645                 650                 655
Val Ser Ile Ala Ser Ile Leu Thr Asn Thr Met Glu Glu Leu Glu Glu
            660                 665                 670
Ser Arg Gln Lys Cys Pro Pro Cys Trp Tyr Arg Phe Ala Asn Val Phe
            675                 680                 685
Leu Ile Trp Asp Cys Cys Asp Ala Trp Leu Lys Val Lys His Leu Val
            690                 695                 700
Asn Leu Ile Val Met Asp Pro Phe Val Asp Leu Ala Ile Thr Ile Cys
705                 710                 715                 720
Ile Val Leu Asn Thr Leu Phe Met Ala Met Glu His Tyr Pro Met Thr
                725                 730                 735
Glu Gln Phe Ser Ser Val Leu Thr Val Gly Asn Leu Val Phe Thr Gly
            740                 745                 750
Ile Phe Thr Ala Glu Met Val Leu Lys Ile Ile Ala Met Asp Pro Tyr
            755                 760                 765
Tyr Tyr Phe Gln Glu Gly Trp Asn Ile Phe Asp Gly Ile Ile Val Ser
            770                 775                 780
Leu Ser Leu Met Glu Leu Gly Leu Ser Asn Val Glu Gly Leu Ser Val
785                 790                 795                 800
Leu Arg Ser Phe Arg Leu Leu Arg Val Phe Lys Leu Ala Lys Ser Trp
                805                 810                 815
Pro Thr Leu Asn Met Leu Ile Lys Ile Ile Gly Asn Ser Val Gly Ala
            820                 825                 830
Leu Gly Asn Leu Thr Leu Val Leu Ala Ile Ile Val Phe Ile Phe Ala
            835                 840                 845
```

-continued

```
Val Val Gly Met Gln Leu Phe Gly Lys Ser Tyr Lys Glu Cys Val Cys
850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
            900                 905                 910

Ile Val Phe Met Leu Val Met Val Ile Gly Asn Leu Val Val Leu Asn
                915                 920                 925

Leu Phe Leu Ala Leu Leu Leu Ser Ser Phe Ser Ser Asp Asn Leu Ala
930                 935                 940

Ala Thr Asp Asp Asp Asn Glu Met Asn Asn Leu Gln Ile Ala Val Gly
945                 950                 955                 960

Arg Met Gln Lys Gly Ile Asp Tyr Val Lys Asn Lys Met Arg Glu Cys
                965                 970                 975

Phe Gln Lys Ala Phe Phe Arg Lys Pro Lys Val Ile Glu Ile His Glu
                980                 985                 990

Gly Asn Lys Ile Asp Ser Cys Met Ser Asn Thr Gly Ile Glu Ile
                995                 1000                1005

Ser Lys Glu Leu Asn Tyr Leu Arg Asp Gly Asn Gly Thr Thr Ser
1010                1015                1020

Gly Val Gly Thr Gly Ser Ser Val Glu Lys Tyr Val Ile Asp Glu
1025                1030                1035

Asn Asp Tyr Met Ser Phe Ile Asn Asn Pro Ser Leu Thr Val Thr
1040                1045                1050

Val Pro Ile Ala Val Gly Glu Ser Asp Phe Glu Asn Leu Asn Thr
1055                1060                1065

Glu Glu Phe Ser Ser Glu Ser Glu Leu Glu Glu Ser Lys Glu Lys
1070                1075                1080

Leu Asn Ala Thr Ser Ser Ser Glu Gly Ser Thr Val Asp Val Val
1085                1090                1095

Leu Pro Arg Glu Gly Glu Gln Ala Glu Thr Glu Pro Glu Glu Asp
1100                1105                1110

Leu Lys Pro Glu Ala Cys Phe Thr Glu Gly Cys Ile Lys Lys Phe
1115                1120                1125

Pro Phe Cys Gln Val Ser Thr Glu Glu Gly Lys Gly Lys Ile Trp
1130                1135                1140

Trp Asn Leu Arg Lys Thr Cys Tyr Ser Ile Val Glu His Asn Trp
1145                1150                1155

Phe Glu Thr Phe Ile Val Phe Met Ile Leu Leu Ser Ser Gly Ala
1160                1165                1170

Leu Ala Phe Glu Asp Ile Tyr Ile Glu Gln Arg Lys Thr Ile Lys
1175                1180                1185

Thr Met Leu Glu Tyr Ala Asp Lys Val Phe Thr Tyr Ile Phe Ile
1190                1195                1200

Leu Glu Met Leu Leu Lys Trp Val Ala Tyr Gly Phe Gln Thr Tyr
1205                1210                1215

Phe Thr Asn Ala Trp Cys Trp Leu Asp Phe Leu Ile Val Asp Val
1220                1225                1230

Ser Leu Val Ser Leu Val Ala Asn Ala Leu Gly Tyr Ser Glu Leu
1235                1240                1245

Gly Ala Ile Lys Ser Leu Arg Thr Leu Arg Ala Leu Arg Pro Leu
1250                1255                1260
```

-continued

```
Arg Ala Leu Ser Arg Phe Glu Gly Met Arg Val Val Asn Ala
1265             1270                 1275

Leu Val Gly Ala Ile Pro Ser Ile Met Asn Val Leu Leu Val Cys
1280             1285                 1290

Leu Ile Phe Trp Leu Ile Phe Ser Ile Met Gly Val Asn Leu Phe
1295             1300                 1305

Ala Gly Lys Phe Tyr His Cys Val Asn Met Thr Thr Gly Asn Met
1310             1315                 1320

Phe Asp Ile Ser Asp Val Asn Asn Leu Ser Asp Cys Gln Ala Leu
1325             1330                 1335

Gly Lys Gln Ala Arg Trp Lys Asn Val Lys Val Asn Phe Asp Asn
1340             1345                 1350

Val Gly Ala Gly Tyr Leu Ala Leu Leu Gln Val Ala Thr Phe Lys
1355             1360                 1365

Gly Trp Met Asp Ile Met Tyr Ala Ala Val Asp Ser Arg Asp Val
1370             1375                 1380

Lys Leu Gln Pro Val Tyr Glu Glu Asn Leu Tyr Met Tyr Leu Tyr
1385             1390                 1395

Phe Val Ile Phe Ile Ile Phe Gly Ser Phe Phe Thr Leu Asn Leu
1400             1405                 1410

Phe Ile Gly Val Ile Ile Asp Asn Phe Asn Gln Gln Lys Lys Lys
1415             1420                 1425

Phe Gly Gly Gln Asp Ile Phe Met Thr Glu Glu Gln Lys Lys Tyr
1430             1435                 1440

Tyr Asn Ala Met Lys Lys Leu Gly Ser Lys Lys Pro Gln Lys Pro
1445             1450                 1455

Ile Pro Arg Pro Ala Asn Lys Phe Gln Gly Met Val Phe Asp Phe
1460             1465                 1470

Val Thr Arg Gln Val Phe Asp Ile Ser Ile Met Ile Leu Ile Cys
1475             1480                 1485

Leu Asn Met Val Thr Met Met Val Glu Thr Asp Asp Gln Gly Lys
1490             1495                 1500

Tyr Met Thr Leu Val Leu Ser Arg Ile Asn Leu Val Phe Ile Val
1505             1510                 1515

Leu Phe Thr Gly Glu Phe Val Leu Lys Leu Val Ser Leu Arg His
1520             1525                 1530

Tyr Tyr Phe Thr Ile Gly Trp Asn Ile Phe Asp Phe Val Val Val
1535             1540                 1545

Ile Leu Ser Ile Val Gly Met Phe Leu Ala Glu Met Ile Glu Lys
1550             1555                 1560

Tyr Phe Val Ser Pro Thr Leu Phe Arg Val Ile Arg Leu Ala Arg
1565             1570                 1575

Ile Gly Arg Ile Leu Arg Leu Ile Lys Gly Ala Lys Gly Ile Arg
1580             1585                 1590

Thr Leu Leu Phe Ala Leu Met Met Ser Leu Pro Ala Leu Phe Asn
1595             1600                 1605

Ile Gly Leu Leu Leu Phe Leu Val Met Phe Ile Tyr Ala Ile Phe
1610             1615                 1620

Gly Met Ser Asn Phe Ala Tyr Val Lys Lys Glu Ala Gly Ile Asp
1625             1630                 1635

Asp Met Phe Asn Phe Glu Thr Phe Gly Asn Ser Met Ile Cys Leu
1640             1645                 1650

Phe Gln Ile Thr Thr Ser Ala Gly Trp Asp Gly Leu Leu Ala Pro
```

```
                  1655                1660                1665

Ile Leu Asn Ser Ala Pro Pro Asp Cys Asp Pro Asp Thr Ile His
              1670                1675                1680

Pro Gly Ser Ser Val Lys Gly Asp Cys Gly Asn Pro Ser Val Gly
              1685                1690                1695

Ile Phe Phe Phe Val Ser Tyr Ile Ile Ile Ser Phe Leu Val Val
              1700                1705                1710

Val Asn Met Tyr Ile Ala Val Ile Leu Glu Asn Phe Ser Val Ala
              1715                1720                1725

Thr Glu Glu Ser Ala Glu Pro Leu Ser Glu Asp Asp Phe Glu Met
              1730                1735                1740

Phe Tyr Glu Val Trp Glu Lys Phe Asp Pro Asp Ala Thr Gln Phe
              1745                1750                1755

Ile Glu Phe Ser Lys Leu Ser Asp Phe Ala Ala Ala Leu Asp Pro
              1760                1765                1770

Pro Leu Leu Ile Ala Lys Pro Asn Lys Val Gln Leu Ile Ala Met
              1775                1780                1785

Asp Leu Pro Met Val Ser Gly Asp Arg Ile His Cys Leu Asp Ile
              1790                1795                1800

Leu Phe Ala Phe Thr Lys Arg Val Leu Gly Glu Ser Gly Glu Met
              1805                1810                1815

Asp Ala Leu Arg Ile Gln Met Glu Asp Arg Phe Met Ala Ser Asn
              1820                1825                1830

Pro Ser Lys Val Ser Tyr Glu Pro Ile Thr Thr Thr Leu Lys Arg
              1835                1840                1845

Lys Gln Glu Glu Val Ser Ala Ala Ile Ile Gln Arg Asn Phe Arg
              1850                1855                1860

Cys Tyr Leu Leu Lys Gln Arg Leu Lys Asn Ile Ser Ser Asn Tyr
              1865                1870                1875

Asn Lys Glu Ala Ile Lys Gly Arg Ile Asp Leu Pro Ile Lys Gln
              1880                1885                1890

Asp Met Ile Ile Asp Lys Leu Asn Gly Asn Ser Thr Pro Glu Lys
              1895                1900                1905

Thr Asp Gly Ser Ser Ser Thr Thr Ser Pro Pro Ser Tyr Asp Ser
              1910                1915                1920

Val Thr Lys Pro Asp Lys Glu Lys Phe Glu Lys Asp Lys Pro Glu
              1925                1930                1935

Lys Glu Ser Lys Gly Lys Glu Val Arg Glu Asn Gln Lys
              1940                1945                1950

<210> SEQ ID NO 6
<211> LENGTH: 2000
<212> TYPE: PRT
<213> ORGANISM: Homo sapiens

<400> SEQUENCE: 6

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
```

```
                65                  70                  75                  80
Asp Pro Tyr Tyr Ile Asn Lys Lys Thr Phe Ile Val Met Asn Lys Gly
                        85                  90                  95
Lys Ala Ile Phe Arg Phe Ser Ala Thr Ser Ala Leu Tyr Ile Leu Thr
                    100                 105                 110
Pro Leu Asn Pro Val Arg Lys Ile Ala Ile Lys Ile Leu Val His Ser
                115                 120                 125
Leu Phe Ser Met Leu Ile Met Cys Thr Ile Leu Thr Asn Cys Val Phe
            130                 135                 140
Met Thr Leu Ser Asn Pro Pro Asp Trp Thr Lys Asn Val Glu Tyr Thr
145                 150                 155                 160
Phe Thr Gly Ile Tyr Thr Phe Glu Ser Leu Ile Lys Ile Leu Ala Arg
                165                 170                 175
Gly Phe Cys Leu Glu Asp Phe Thr Phe Leu Arg Asp Pro Trp Asn Trp
            180                 185                 190
Leu Asp Phe Ser Val Ile Val Met Ala Tyr Val Thr Glu Phe Val Asp
        195                 200                 205
Leu Gly Asn Val Ser Ala Leu Arg Thr Phe Arg Val Leu Arg Ala Leu
    210                 215                 220
Lys Thr Ile Ser Val Ile Pro Gly Leu Lys Thr Ile Val Gly Ala Leu
225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Leu Gln Trp Pro Pro Ser Asp Ser Ala Phe Glu
        275                 280                 285
Thr Asn Thr Thr Ser Tyr Phe Asn Gly Thr Met Asp Ser Asn Gly Thr
    290                 295                 300
Phe Val Asn Val Thr Met Ser Thr Phe Asn Trp Lys Asp Tyr Ile Gly
305                 310                 315                 320
Asp Asp Ser His Phe Tyr Val Leu Asp Gly Gln Lys Asp Pro Leu Leu
                325                 330                 335
Cys Gly Asn Gly Ser Asp Ala Gly Gln Cys Pro Glu Gly Tyr Ile Cys
            340                 345                 350
Val Lys Ala Gly Arg Asn Pro Asn Tyr Gly Tyr Thr Ser Phe Asp Thr
        355                 360                 365
Phe Ser Trp Ala Phe Leu Ser Leu Phe Arg Leu Met Thr Gln Asp Tyr
    370                 375                 380
Trp Glu Asn Leu Tyr Gln Leu Thr Leu Arg Ala Ala Gly Lys Thr Tyr
385                 390                 395                 400
Met Ile Phe Phe Val Leu Val Ile Phe Leu Gly Ser Phe Tyr Leu Val
                405                 410                 415
Asn Leu Ile Leu Ala Val Val Ala Met Ala Tyr Glu Glu Gln Asn Gln
            420                 425                 430
Ala Thr Leu Glu Glu Ala Glu Gln Lys Glu Ala Glu Phe Gln Gln Met
        435                 440                 445
Leu Glu Gln Leu Lys Lys Gln Gln Glu Glu Ala Gln Ala Val Ala Ala
    450                 455                 460
Ala Ser Ala Ala Ser Arg Asp Phe Ser Gly Val Gly Gly Leu Gly Glu
465                 470                 475                 480
Leu Leu Glu Ser Ser Ser Glu Ala Ser Lys Leu Ser Ser Lys Gly Ala
                485                 490                 495
```

-continued

Lys Glu Trp Arg Asn Arg Arg Lys Arg Gln Arg Glu His Leu
            500                 505             510

Glu Gly Asn Asn Lys Gly Glu Arg Asp Ser Phe Pro Lys Ser Glu Ser
        515                 520                 525

Glu Asp Ser Val Lys Arg Ser Ser Phe Leu Phe Ser Met Asp Gly Asn
    530                 535                 540

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Arg Asn Ser Lys Thr Ser
                565                 570                 575

Ile Phe Ser Phe Arg Gly Arg Ala Lys Asp Val Gly Ser Glu Asn Asp
            580                 585                 590

Phe Ala Asp Asp Glu His Ser Thr Phe Glu Asp Gly Glu Ser Arg Arg
        595                 600                 605

Asp Ser Leu Phe Val Pro His Arg His Gly Glu Arg Arg Asn Ser Asn
    610                 615                 620

Val Ser Gln Ala Ser Met Ser Ser Arg Met Val Pro Gly Leu Pro Ala
625                 630                 635                 640

Asn Gly Lys Met His Ser Thr Val Asp Cys Asn Gly Val Val Ser Leu
                645                 650                 655

Val Gly Gly Pro Ser Ala Leu Thr Ser Pro Thr Gly Gln Leu Pro Pro
            660                 665                 670

Glu Gly Thr Thr Thr Glu Thr Glu Val Arg Lys Arg Arg Leu Ser Ser
        675                 680                 685

Tyr Gln Ile Ser Met Glu Met Leu Glu Asp Ser Ser Gly Arg Gln Arg
    690                 695                 700

Ala Val Ser Ile Ala Ser Ile Leu Thr Asn Thr Met Glu Glu Leu Glu
705                 710                 715                 720

Glu Ser Arg Gln Lys Cys Pro Pro Cys Trp Tyr Arg Phe Ala Asn Val
                725                 730                 735

Phe Leu Ile Trp Asp Cys Cys Asp Ala Trp Leu Lys Val Lys His Leu
            740                 745                 750

Val Asn Leu Ile Val Met Asp Pro Phe Val Asp Leu Ala Ile Thr Ile
        755                 760                 765

Cys Ile Val Leu Asn Thr Leu Phe Met Ala Met Glu His Tyr Pro Met
    770                 775                 780

Thr Glu Gln Phe Ser Ser Val Leu Thr Val Gly Asn Leu Val Phe Thr
785                 790                 795                 800

Gly Ile Phe Thr Ala Glu Met Val Leu Lys Ile Ala Met Asp Pro
                805                 810                 815

Tyr Tyr Tyr Phe Gln Glu Gly Trp Asn Ile Phe Asp Gly Ile Ile Val
            820                 825                 830

Ser Leu Ser Leu Met Glu Leu Gly Leu Ser Asn Val Glu Gly Leu Ser
        835                 840                 845

Val Leu Arg Ser Phe Arg Leu Leu Arg Val Phe Lys Leu Ala Lys Ser
    850                 855                 860

Trp Pro Thr Leu Asn Met Leu Ile Lys Ile Ile Gly Asn Ser Val Gly
865                 870                 875                 880

Ala Leu Gly Asn Leu Thr Leu Val Leu Ala Ile Ile Val Phe Ile Phe
                885                 890                 895

Ala Val Val Gly Met Gln Leu Phe Gly Lys Ser Tyr Lys Glu Cys Val
            900                 905                 910

Cys Lys Ile Asn Asp Asp Cys Thr Leu Pro Arg Trp His Met Asn Asp
        915                 920                 925

-continued

```
Phe Phe His Ser Phe Leu Ile Val Phe Arg Val Leu Cys Gly Glu Trp
    930                 935                 940
Ile Glu Thr Met Trp Asp Cys Met Glu Val Ala Gly Gln Thr Met Cys
945                 950                 955                 960
Leu Ile Val Phe Met Leu Val Met Val Ile Gly Asn Leu Val Val Leu
                965                 970                 975
Asn Leu Phe Leu Ala Leu Leu Leu Ser Ser Phe Ser Ser Asp Asn Leu
                980                 985                 990
Ala Ala Thr Asp Asp Asp Asn Glu Met Asn Asn Leu Gln Ile Ala Val
            995                1000                1005
Gly Arg Met Gln Lys Gly Ile Asp Tyr Val Lys Asn Lys Met Arg
       1010                 1015                1020
Glu Cys Phe Gln Lys Ala Phe Phe Arg Lys Pro Lys Val Ile Glu
       1025                1030                1035
Ile His Glu Gly Asn Lys Ile Asp Ser Cys Met Ser Asn Asn Thr
       1040                1045                1050
Gly Ile Glu Ile Ser Lys Glu Leu Asn Tyr Leu Arg Asp Gly Asn
       1055                1060                1065
Gly Thr Thr Ser Gly Val Gly Thr Gly Ser Ser Val Glu Lys Tyr
       1070                1075                1080
Val Ile Asp Glu Asn Asp Tyr Met Ser Phe Ile Asn Asn Pro Ser
       1085                1090                1095
Leu Thr Val Thr Val Pro Ile Ala Val Gly Glu Ser Asp Phe Glu
       1100                1105                1110
Asn Leu Asn Thr Glu Glu Phe Ser Ser Glu Ser Glu Leu Glu Glu
       1115                1120                1125
Ser Lys Glu Lys Leu Asn Ala Thr Ser Ser Ser Glu Gly Ser Thr
       1130                1135                1140
Val Asp Val Val Leu Pro Arg Glu Gly Glu Gln Ala Glu Thr Glu
       1145                1150                1155
Pro Glu Glu Asp Phe Lys Pro Glu Ala Cys Phe Thr Glu Gly Cys
       1160                1165                1170
Ile Lys Lys Phe Pro Phe Cys Gln Val Ser Thr Glu Glu Gly Lys
       1175                1180                1185
Gly Lys Ile Trp Trp Asn Leu Arg Lys Thr Cys Tyr Ser Ile Val
       1190                1195                1200
Glu His Asn Trp Phe Glu Thr Phe Ile Val Phe Met Ile Leu Leu
       1205                1210                1215
Ser Ser Gly Ala Leu Ala Phe Glu Asp Ile Tyr Ile Glu Gln Arg
       1220                1225                1230
Lys Thr Ile Lys Thr Met Leu Glu Tyr Ala Asp Lys Val Phe Thr
       1235                1240                1245
Tyr Ile Phe Ile Leu Glu Met Leu Leu Lys Trp Val Ala Tyr Gly
       1250                1255                1260
Phe Gln Thr Tyr Phe Thr Asn Ala Trp Cys Trp Leu Asp Phe Leu
       1265                1270                1275
Ile Val Asp Val Ser Leu Val Ser Leu Val Ala Asn Ala Leu Gly
       1280                1285                1290
Tyr Ser Glu Leu Gly Ala Ile Lys Ser Leu Arg Thr Leu Arg Ala
       1295                1300                1305
Leu Arg Pro Leu Arg Ala Leu Ser Arg Phe Glu Gly Met Arg Val
       1310                1315                1320
Val Val Asn Ala Leu Val Gly Ala Ile Pro Ser Ile Met Asn Val
```

-continued

```
            1325                1330                1335

Leu Leu Val Cys Leu Ile Phe Trp Leu Ile Phe Ser Ile Met Gly
        1340                1345                1350

Val Asn Leu Phe Ala Gly Lys Phe Tyr His Cys Val Asn Met Thr
        1355                1360                1365

Thr Gly Asn Met Phe Asp Ile Ser Asp Val Asn Asn Leu Ser Asp
        1370                1375                1380

Cys Gln Ala Leu Gly Lys Gln Ala Arg Trp Lys Asn Val Lys Val
        1385                1390                1395

Asn Phe Asp Asn Val Gly Ala Gly Tyr Leu Ala Leu Leu Gln Val
        1400                1405                1410

Ala Thr Phe Lys Gly Trp Met Asp Ile Met Tyr Ala Ala Val Asp
        1415                1420                1425

Ser Arg Asp Val Lys Leu Gln Pro Val Tyr Glu Glu Asn Leu Tyr
        1430                1435                1440

Met Tyr Leu Tyr Phe Val Ile Phe Ile Ile Phe Gly Ser Phe Phe
        1445                1450                1455

Thr Leu Asn Leu Phe Ile Gly Val Ile Ile Asp Asn Phe Asn Gln
        1460                1465                1470

Gln Lys Lys Lys Phe Gly Gly Gln Asp Ile Phe Met Thr Glu Glu
        1475                1480                1485

Gln Lys Lys Tyr Tyr Asn Ala Met Lys Lys Leu Gly Ser Lys Lys
        1490                1495                1500

Pro Gln Lys Pro Ile Pro Arg Pro Ala Asn Lys Phe Gln Gly Met
        1505                1510                1515

Val Phe Asp Phe Val Thr Arg Gln Val Phe Asp Ile Ser Ile Met
        1520                1525                1530

Ile Leu Ile Cys Leu Asn Met Val Thr Met Met Val Glu Thr Asp
        1535                1540                1545

Asp Gln Gly Lys Tyr Met Thr Leu Val Leu Ser Arg Ile Asn Leu
        1550                1555                1560

Val Phe Ile Val Leu Phe Thr Gly Glu Phe Val Leu Lys Leu Val
        1565                1570                1575

Ser Leu Arg His Tyr Tyr Phe Thr Ile Gly Trp Asn Ile Phe Asp
        1580                1585                1590

Phe Val Val Val Ile Leu Ser Ile Val Gly Met Phe Leu Ala Glu
        1595                1600                1605

Met Ile Glu Lys Tyr Ser Val Ser Pro Thr Leu Phe Arg Val Ile
        1610                1615                1620

Arg Leu Ala Arg Ile Gly Arg Ile Leu Arg Leu Ile Lys Gly Ala
        1625                1630                1635

Lys Gly Ile Arg Thr Leu Leu Phe Ala Leu Met Met Ser Leu Pro
        1640                1645                1650

Ala Leu Phe Asn Ile Gly Leu Leu Leu Phe Leu Val Met Phe Ile
        1655                1660                1665

Tyr Ala Ile Phe Gly Met Ser Asn Phe Ala Tyr Val Lys Lys Glu
        1670                1675                1680

Ala Gly Ile Asp Asp Met Phe Asn Phe Glu Thr Phe Gly Asn Ser
        1685                1690                1695

Met Ile Cys Leu Phe Gln Ile Thr Thr Ser Ala Gly Trp Asp Gly
        1700                1705                1710

Leu Leu Ala Pro Ile Leu Asn Ser Ala Pro Pro Asp Cys Asp Pro
        1715                1720                1725
```

-continued

Asp Thr Ile His Pro Gly Ser Ser Val Lys Gly Asp Arg Gly Asp
             1730                1735                1740

Pro Ser Val Gly Ile Phe Phe Val Ser Tyr Ile Ile Ser
    1745                1750                1755

Phe Leu Val Val Val Asn Met Tyr Ile Ala Val Ile Leu Glu Asn
    1760                1765                1770

Phe Ser Val Ala Thr Glu Glu Ser Ala Glu Pro Leu Ser Glu Asp
    1775                1780                1785

Asp Phe Glu Met Phe Tyr Glu Val Trp Glu Lys Phe Asp Pro Asp
    1790                1795                1800

Ala Thr Gln Phe Ile Glu Phe Ser Lys Leu Ser Asp Phe Ala Ala
    1805                1810                1815

Ala Leu Asp Pro Pro Leu Leu Ile Ala Lys Pro Asn Lys Val Gln
    1820                1825                1830

Leu Ile Ala Met Asp Leu Pro Met Val Ser Gly Asp Arg Ile His
    1835                1840                1845

Cys Leu Asp Ile Leu Phe Ala Phe Thr Lys Arg Val Leu Cys Glu
    1850                1855                1860

Ser Gly Glu Met Asp Ala Leu Arg Ile Gln Met Glu Asp Arg Phe
    1865                1870                1875

Met Ala Ser Asn Pro Ser Lys Val Ser Tyr Glu Pro Ile Thr Thr
    1880                1885                1890

Thr Leu Lys Arg Lys Gln Glu Glu Val Ser Ala Ala Ile Ile Gln
    1895                1900                1905

Arg Asn Phe Arg Cys Tyr Leu Leu Lys Gln Arg Leu Lys Asn Ile
    1910                1915                1920

Ser Ser Asn Tyr Asn Lys Glu Ala Ile Lys Gly Arg Ile Asp Leu
    1925                1930                1935

Pro Ile Lys Gln Asp Met Ile Ile Asp Lys Leu Asn Gly Asn Ser
    1940                1945                1950

Thr Pro Glu Lys Thr Asp Gly Ser Ser Ser Thr Thr Pro Pro Pro
    1955                1960                1965

Ser Tyr Asp Ser Val Thr Lys Pro Asp Lys Glu Lys Phe Glu Lys
    1970                1975                1980

Asp Lys Pro Glu Lys Glu Ser Lys Gly Lys Glu Val Arg Glu Asn
    1985                1990                1995

Gln Lys
    2000

<210> SEQ ID NO 7
<211> LENGTH: 1951
<212> TYPE: PRT
<213> ORGANISM: Homo sapiens

<400> SEQUENCE: 7

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
                20                  25                  30

Lys Ala Lys Lys Pro Lys Lys Glu Gln Asp Asn Asp Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

-continued

```
Asp Pro Tyr Tyr Ile Asn Lys Lys Thr Phe Ile Val Met Asn Lys Gly
                 85                  90                  95
Lys Ala Ile Phe Arg Phe Ser Ala Thr Ser Ala Leu Tyr Ile Leu Thr
            100                 105                 110
Pro Leu Asn Pro Val Arg Lys Ile Ala Ile Lys Ile Leu Val His Ser
        115                 120                 125
Leu Phe Ser Met Leu Ile Met Cys Thr Ile Leu Thr Asn Cys Val Phe
    130                 135                 140
Met Thr Leu Ser Asn Pro Pro Asp Trp Thr Lys Asn Val Glu Tyr Thr
145                 150                 155                 160
Phe Thr Gly Ile Tyr Thr Phe Glu Ser Leu Ile Lys Ile Leu Ala Arg
                165                 170                 175
Gly Phe Cys Leu Glu Asp Phe Thr Phe Leu Arg Asp Pro Trp Asn Trp
            180                 185                 190
Leu Asp Phe Ser Val Ile Val Met Ala Tyr Val Thr Glu Phe Val Ser
        195                 200                 205
Leu Gly Asn Val Ser Ala Leu Arg Thr Phe Arg Val Leu Arg Ala Leu
    210                 215                 220
Lys Thr Ile Ser Val Ile Pro Gly Leu Lys Thr Ile Val Gly Ala Leu
225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Leu Gln Trp Pro Pro Ser Asp Ser Ala Phe Glu
        275                 280                 285
Thr Asn Thr Thr Ser Tyr Phe Asn Gly Thr Met Asp Ser Asn Gly Thr
    290                 295                 300
Phe Val Asn Val Thr Met Ser Thr Phe Asn Trp Lys Asp Tyr Ile Gly
305                 310                 315                 320
Asp Asp Ser His Phe Tyr Val Leu Asp Gly Gln Lys Asp Pro Leu Leu
                325                 330                 335
Cys Gly Asn Gly Ser Asp Ala Gly Gln Cys Pro Glu Gly Tyr Ile Cys
            340                 345                 350
Val Lys Ala Gly Arg Asn Pro Asn Tyr Gly Tyr Thr Ser Phe Asp Thr
        355                 360                 365
Phe Ser Trp Ala Phe Leu Ser Leu Phe Arg Leu Met Thr Gln Asp Tyr
    370                 375                 380
Trp Glu Asn Leu Tyr Gln Leu Thr Leu Arg Ala Ala Gly Lys Thr Tyr
385                 390                 395                 400
Met Ile Phe Phe Val Leu Val Ile Phe Leu Gly Ser Phe Tyr Leu Val
                405                 410                 415
Asn Leu Ile Leu Ala Val Val Ala Met Ala Tyr Glu Glu Gln Asn Gln
            420                 425                 430
Ala Thr Leu Glu Glu Ala Glu Gln Lys Glu Ala Glu Phe Gln Gln Met
        435                 440                 445
Leu Glu Gln Leu Lys Lys Gln Gln Glu Glu Ala Gln Ala Val Ala Ala
    450                 455                 460
Ala Ser Ala Ala Ser Arg Asp Phe Ser Gly Ile Gly Gly Leu Gly Glu
465                 470                 475                 480
Leu Leu Glu Ser Ser Ser Glu Ala Ser Lys Leu Ser Ser Lys Ser Ala
                485                 490                 495
Lys Glu Trp Arg Asn Arg Arg Lys Lys Arg Arg Gln Arg Glu His Leu
            500                 505                 510
```

```
Glu Gly Asn Asn Lys Gly Glu Arg Asp Ser Phe Pro Lys Ser Glu Ser
            515                 520                 525

Glu Asp Ser Val Lys Arg Ser Ser Phe Leu Phe Ser Met Asp Gly Asn
        530                 535                 540

Arg Leu Thr Ser Asp Lys Lys Phe Cys Ser Pro His Gln Ser Leu Leu
545                 550                 555                 560

Ser Ile Arg Gly Ser Leu Phe Ser Pro Arg Arg Asn Ser Lys Thr Ser
                565                 570                 575

Ile Phe Ser Phe Arg Gly Arg Ala Lys Asp Val Gly Ser Glu Asn Asp
            580                 585                 590

Phe Ala Asp Asp Glu His Ser Thr Phe Glu Asp Ser Glu Ser Arg Arg
        595                 600                 605

Asp Ser Leu Phe Val Pro His Arg His Gly Glu Arg Arg Asn Ser Asn
    610                 615                 620

Gly Thr Thr Thr Glu Thr Glu Val Arg Lys Arg Arg Leu Ser Ser Tyr
625                 630                 635                 640

Gln Ile Ser Met Glu Met Leu Glu Asp Ser Ser Gly Arg Gln Arg Ala
                645                 650                 655

Val Ser Ile Ala Ser Ile Leu Thr Asn Thr Met Glu Glu Leu Glu Glu
            660                 665                 670

Ser Arg Gln Lys Cys Pro Pro Cys Trp Tyr Arg Phe Ala Asn Val Phe
        675                 680                 685

Leu Ile Trp Asp Cys Cys Asp Ala Trp Leu Lys Val Lys His Leu Val
    690                 695                 700

Asn Leu Ile Val Met Asp Pro Phe Val Asp Leu Ala Ile Thr Ile Cys
705                 710                 715                 720

Ile Val Leu Asn Thr Leu Phe Met Ala Met Glu His Tyr Pro Met Thr
                725                 730                 735

Glu Gln Phe Ser Ser Val Leu Thr Val Gly Asn Leu Val Phe Thr Gly
            740                 745                 750

Ile Phe Thr Ala Glu Met Val Leu Lys Ile Ile Ala Met Asp Pro Tyr
        755                 760                 765

Tyr Tyr Phe Gln Glu Gly Trp Asn Ile Phe Asp Gly Ile Ile Val Ser
    770                 775                 780

Leu Ser Leu Met Glu Leu Gly Leu Ser Asn Val Glu Gly Leu Ser Val
785                 790                 795                 800

Leu Arg Ser Phe Arg Leu Leu Arg Val Phe Lys Leu Ala Lys Ser Trp
                805                 810                 815

Pro Thr Leu Asn Met Leu Ile Lys Ile Ile Gly Asn Ser Val Gly Ala
            820                 825                 830

Leu Gly Asn Leu Thr Leu Val Leu Ala Ile Ile Val Phe Ile Phe Ala
        835                 840                 845

Val Val Gly Met Gln Leu Phe Gly Lys Ser Tyr Lys Glu Cys Val Cys
    850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
            900                 905                 910

Ile Val Phe Met Leu Val Met Val Ile Gly Asn Leu Val Val Leu Asn
        915                 920                 925

Leu Phe Leu Ala Leu Leu Leu Ser Ser Phe Ser Ser Asp Asn Leu Ala
```

```
                930            935           940
Ala Thr Asp Asp Asp Asn Glu Met Asn Asn Leu Gln Ile Ala Val Gly
945                 950               955               960

Arg Met Gln Lys Gly Ile Asp Tyr Val Lys Asn Lys Met Arg Glu Cys
            965               970               975

Phe Gln Lys Ala Phe Phe Arg Lys Pro Lys Val Ile Glu Ile His Glu
                980               985               990

Gly Asn Lys Ile Asp Ser Cys Met  Ser Asn Asn Thr Gly Ile Glu Ile
            995                 1000              1005

Ser Lys Glu Leu Asn Tyr Leu Arg Asp Gly Asn Gly  Thr Thr Ser
    1010              1015             1020

Gly Val Gly Thr Gly Ser Ser  Val Glu Lys Tyr Val  Ile Asp Glu
    1025             1030              1035

Asn Asp Tyr Met Ser Phe Ile  Asn Asn Pro Ser Leu  Thr Val Thr
    1040             1045              1050

Val Pro Ile Ala Val Gly Glu  Ser Asp Phe Glu Asn  Leu Asn Thr
    1055             1060              1065

Glu Glu Phe Ser Ser Glu Ser  Glu Leu Glu Glu Ser  Lys Glu Lys
    1070             1075              1080

Leu Asn Ala Thr Ser Ser Ser  Glu Gly Ser Thr Val  Asp Val Val
    1085             1090              1095

Leu Pro Arg Glu Gly Glu Gln  Ala Glu Thr Glu Pro  Glu Glu Asp
    1100             1105              1110

Leu Lys Pro Glu Ala Cys Phe  Thr Glu Gly Cys Ile  Lys Lys Phe
    1115             1120              1125

Pro Phe Cys Gln Val Ser Thr  Glu Glu Gly Lys Gly  Lys Ile Trp
    1130             1135              1140

Trp Asn Leu Arg Lys Thr Cys  Tyr Ser Ile Val Glu  His Asn Trp
    1145             1150              1155

Phe Glu Thr Phe Ile Val Phe  Met Ile Leu Leu Ser  Ser Gly Ala
    1160             1165              1170

Leu Ala Phe Glu Asp Ile Tyr  Ile Glu Gln Arg Lys  Thr Ile Lys
    1175             1180              1185

Thr Met Leu Glu Tyr Ala Asp  Lys Val Phe Thr Tyr  Ile Phe Ile
    1190             1195              1200

Leu Glu Met Leu Leu Lys Trp  Val Ala Tyr Gly Phe  Gln Thr Tyr
    1205             1210              1215

Phe Thr Asn Ala Trp Cys Trp  Leu Asp Phe Leu Ile  Val Asp Val
    1220             1225              1230

Ser Leu Val Ser Leu Val Ala  Asn Ala Leu Gly Tyr  Ser Glu Leu
    1235             1240              1245

Gly Ala Ile Lys Ser Leu Arg  Thr Leu Arg Ala Leu  Arg Pro Leu
    1250             1255              1260

Arg Ala Leu Ser Arg Phe Glu  Gly Met Arg Val Val  Val Asn Ala
    1265             1270              1275

Leu Val Gly Ala Ile Pro Ser  Ile Met Asn Val Leu  Leu Val Cys
    1280             1285              1290

Leu Ile Phe Trp Leu Ile Phe  Ser Ile Met Gly Val  Asn Leu Phe
    1295             1300              1305

Ala Gly Lys Phe Tyr His Cys  Val Asn Met Thr Thr  Gly Asn Met
    1310             1315              1320

Phe Asp Ile Ser Asp Val Asn  Asn Leu Ser Asp Cys  Gln Ala Leu
    1325             1330              1335
```

```
Gly Lys Gln Ala Arg Trp Lys Asn Val Lys Val Asn Phe Asp Asn
1340                1345                1350

Val Gly Ala Gly Tyr Leu Ala Leu Leu Gln Val Ala Thr Phe Lys
1355                1360                1365

Gly Trp Met Asp Ile Met Tyr Ala Ala Val Asp Ser Arg Asp Val
1370                1375                1380

Lys Leu Gln Pro Val Tyr Glu Glu Asn Leu Tyr Met Tyr Leu Tyr
1385                1390                1395

Phe Val Ile Phe Ile Ile Phe Gly Ser Phe Phe Thr Leu Asn Leu
1400                1405                1410

Phe Ile Gly Val Ile Ile Asp Asn Phe Asn Gln Gln Lys Lys Lys
1415                1420                1425

Phe Gly Gly Gln Asp Ile Phe Met Thr Glu Glu Gln Lys Lys Tyr
1430                1435                1440

Tyr Asn Ala Met Lys Lys Leu Gly Ser Lys Lys Pro Gln Lys Pro
1445                1450                1455

Ile Pro Arg Pro Ala Asn Lys Phe Gln Gly Met Val Phe Asp Phe
1460                1465                1470

Val Thr Arg Gln Val Phe Asp Ile Ser Ile Met Ile Leu Ile Cys
1475                1480                1485

Leu Asn Met Val Thr Met Met Val Glu Thr Asp Asp Gln Gly Lys
1490                1495                1500

Tyr Met Thr Leu Val Leu Ser Arg Ile Asn Leu Val Phe Ile Val
1505                1510                1515

Leu Phe Thr Gly Glu Phe Val Leu Lys Leu Val Ser Leu Arg His
1520                1525                1530

Tyr Tyr Phe Thr Ile Gly Trp Asn Ile Phe Asp Phe Val Val Val
1535                1540                1545

Ile Leu Ser Ile Val Gly Met Phe Leu Ala Glu Met Ile Glu Lys
1550                1555                1560

Tyr Phe Val Ser Pro Thr Leu Phe Arg Val Ile Arg Leu Ala Arg
1565                1570                1575

Ile Gly Arg Ile Leu Arg Leu Ile Lys Gly Ala Lys Gly Ile Arg
1580                1585                1590

Thr Leu Leu Phe Ala Leu Met Met Ser Leu Pro Ala Leu Phe Asn
1595                1600                1605

Ile Gly Leu Leu Leu Phe Leu Val Met Phe Ile Tyr Ala Ile Phe
1610                1615                1620

Gly Met Ser Asn Phe Ala Tyr Val Lys Lys Glu Ala Gly Ile Asp
1625                1630                1635

Asp Met Phe Asn Phe Glu Thr Phe Gly Asn Ser Met Ile Cys Leu
1640                1645                1650

Phe Gln Ile Thr Thr Ser Ala Gly Trp Asp Gly Leu Leu Ala Pro
1655                1660                1665

Ile Leu Asn Ser Ala Pro Pro Asp Cys Asp Pro Asp Thr Ile His
1670                1675                1680

Pro Gly Ser Ser Val Lys Gly Asp Cys Gly Asn Pro Ser Val Gly
1685                1690                1695

Ile Phe Phe Phe Val Ser Tyr Ile Ile Ile Ser Phe Leu Val Val
1700                1705                1710

Val Asn Met Tyr Ile Ala Val Ile Leu Glu Asn Phe Ser Val Ala
1715                1720                1725

Thr Glu Glu Ser Ala Glu Pro Leu Ser Glu Asp Asp Phe Glu Met
1730                1735                1740
```

```
Phe Tyr Glu Val Trp Glu Lys Phe Asp Pro Asp Ala Thr Gln Phe
    1745                1750                1755

Ile Glu Phe Ser Lys Leu Ser Asp Phe Ala Ala Ala Leu Asp Pro
    1760                1765                1770

Pro Leu Leu Ile Ala Lys Pro Asn Lys Val Gln Leu Ile Ala Met
    1775                1780                1785

Asp Leu Pro Met Val Ser Gly Asp Arg Ile His Cys Leu Asp Ile
    1790                1795                1800

Leu Phe Ala Phe Thr Lys Arg Val Leu Gly Glu Ser Gly Glu Met
    1805                1810                1815

Asp Ala Leu Arg Ile Gln Met Glu Asp Arg Phe Met Ala Ser Asn
    1820                1825                1830

Pro Ser Lys Val Ser Tyr Glu Pro Ile Thr Thr Thr Leu Lys Arg
    1835                1840                1845

Lys Gln Glu Glu Val Ser Ala Ala Ile Ile Gln Arg Asn Phe Arg
    1850                1855                1860

Cys Tyr Leu Leu Lys Gln Arg Leu Lys Asn Ile Ser Ser Asn Tyr
    1865                1870                1875

Asn Lys Glu Ala Ile Lys Gly Arg Ile Asp Leu Pro Ile Lys Gln
    1880                1885                1890

Asp Met Ile Ile Asp Lys Leu Asn Gly Asn Ser Thr Pro Glu Lys
    1895                1900                1905

Thr Asp Gly Ser Ser Thr Thr Ser Pro Pro Ser Tyr Asp Ser
    1910                1915                1920

Val Thr Lys Pro Asp Lys Glu Lys Phe Glu Lys Asp Lys Pro Glu
    1925                1930                1935

Lys Glu Ser Lys Gly Lys Glu Val Arg Glu Asn Gln Lys
    1940                1945                1950

<210> SEQ ID NO 8
<211> LENGTH: 1951
<212> TYPE: PRT
<213> ORGANISM: Homo sapiens

<400> SEQUENCE: 8

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
                20                  25                  30

Lys Ala Lys Lys Pro Lys Lys Glu Gln Asp Asn Asp Glu Asn Lys
            35                  40                  45

Pro Lys Pro Asn Ser Asp Leu Glu Ala Gly Lys Asn Leu Pro Phe Ile
        50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Met Asn Lys Gly
                85                  90                  95

Lys Ala Ile Phe Arg Phe Ser Ala Thr Ser Ala Leu Tyr Ile Leu Thr
            100                 105                 110

Pro Leu Asn Pro Val Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160
```

Phe Thr Gly Ile Tyr Thr Phe Glu Ser Leu Ile Lys Ile Leu Ala Arg
                165                 170                 175
Gly Phe Cys Leu Glu Asp Phe Thr Phe Leu Arg Asp Pro Trp Asn Trp
            180                 185                 190
Leu Asp Phe Ser Val Ile Val Met Ala Tyr Val Thr Glu Phe Val Asp
                195                 200                 205
Leu Gly Asn Val Ser Ala Leu Arg Thr Phe Arg Val Leu Arg Ala Leu
        210                 215                 220
Lys Thr Ile Ser Val Ile Pro Gly Leu Lys Thr Ile Val Gly Ala Leu
225                 230                 235                 240
Ile Gln Ser Val Lys Lys Leu Ser Asp Val Met Ile Leu Thr Val Phe
                245                 250                 255
Cys Leu Ser Val Phe Ala Leu Ile Gly Leu Gln Leu Phe Met Gly Asn
            260                 265                 270
Leu Arg Asn Lys Cys Leu Gln Trp Pro Pro Ser Asp Ser Ala Phe Glu
        275                 280                 285
Thr Asn Thr Thr Ser Tyr Phe Asn Gly Thr Met Asp Ser Asn Gly Thr
    290                 295                 300
Phe Val Asn Val Thr Met Ser Thr Phe Asn Trp Lys Asp Tyr Ile Gly
305                 310                 315                 320
Asp Asp Ser His Phe Tyr Val Leu Asp Gly Gln Lys Asp Pro Leu Leu
                325                 330                 335
Cys Gly Asn Gly Ser Asp Ala Gly Gln Cys Pro Glu Gly Tyr Ile Cys
            340                 345                 350
Val Lys Ala Gly Arg Asn Pro Asn Tyr Gly Tyr Thr Ser Phe Asp Thr
        355                 360                 365
Phe Ser Trp Ala Phe Leu Ser Leu Phe Arg Leu Met Thr Gln Asp Tyr
    370                 375                 380
Trp Glu Asn Leu Tyr Gln Leu Thr Leu Arg Ala Ala Gly Lys Thr Tyr
385                 390                 395                 400
Met Ile Phe Phe Val Leu Val Ile Phe Leu Gly Ser Phe Tyr Leu Val
                405                 410                 415
Asn Leu Ile Leu Ala Val Val Ala Met Ala Tyr Glu Glu Gln Asn Gln
            420                 425                 430
Ala Thr Leu Glu Glu Ala Glu Gln Lys Glu Ala Glu Phe Gln Gln Met
        435                 440                 445
Leu Glu Gln Leu Lys Lys Gln Gln Glu Ala Gln Ala Val Ala Ala
    450                 455                 460
Ala Ser Ala Ala Ser Arg Asp Phe Ser Gly Val Gly Gly Leu Gly Glu
465                 470                 475                 480
Leu Leu Glu Ser Ser Ser Glu Ala Ser Lys Leu Ser Ser Lys Gly Ala
                485                 490                 495
Lys Glu Trp Arg Asn Arg Arg Lys Lys Arg Arg Gln Arg Glu His Leu
            500                 505                 510
Glu Gly Asn Asn Lys Gly Glu Arg Asp Ser Phe Pro Lys Ser Glu Ser
        515                 520                 525
Glu Asp Ser Val Lys Arg Ser Ser Phe Leu Phe Ser Met Asp Gly Asn
    530                 535                 540
Arg Leu Thr Ser Asp Lys Asn Arg Lys Lys Arg Gln Arg Glu
545                 550                 555                 560
His Leu Glu Gly Asn Asn Lys Gly Glu Arg Asp Ser Phe Pro Lys Ser
                565                 570                 575
Glu Ser Glu Asp Ser Val Lys Arg Ser Ser Phe Leu Phe Ser Met Asp

```
                     580                 585                 590
Gly Asn Arg Leu Thr Ser Asp Lys Phe Glu Asp Ser Glu Ser Arg Arg
                 595                 600                 605
Asp Ser Leu Phe Val Pro His Arg His Gly Glu Arg Arg Asn Ser Asn
             610                 615                 620
Gly Thr Thr Thr Glu Thr Glu Val Arg Lys Arg Arg Leu Ser Ser Tyr
625                 630                 635                 640
Gln Ile Ser Met Glu Met Leu Glu Asp Ser Ser Gly Arg Gln Arg Ala
                 645                 650                 655
Val Ser Ile Ala Ser Ile Leu Thr Asn Thr Met Glu Glu Leu Glu Glu
             660                 665                 670
Ser Arg Gln Lys Cys Pro Pro Cys Trp Tyr Arg Phe Ala Asn Val Phe
             675                 680                 685
Leu Ile Trp Asp Cys Cys Asp Ala Trp Leu Lys Val Lys His Leu Val
             690                 695                 700
Asn Leu Ile Val Met Asp Pro Phe Val Asp Leu Ala Ile Thr Ile Cys
705                 710                 715                 720
Ile Val Leu Asn Thr Leu Phe Met Ala Met Glu His Tyr Pro Met Thr
                 725                 730                 735
Glu Gln Phe Ser Ser Val Leu Thr Val Gly Asn Leu Val Phe Thr Gly
                 740                 745                 750
Ile Phe Thr Ala Glu Met Val Leu Lys Ile Ile Ala Met Asp Pro Tyr
             755                 760                 765
Tyr Tyr Phe Gln Glu Gly Trp Asn Ile Phe Asp Gly Ile Ile Val Ser
             770                 775                 780
Leu Ser Leu Met Glu Leu Gly Leu Ser Asn Val Glu Gly Leu Ser Val
785                 790                 795                 800
Leu Arg Ser Phe Arg Leu Leu Arg Val Phe Lys Leu Ala Lys Ser Trp
                 805                 810                 815
Pro Thr Leu Asn Met Leu Ile Lys Ile Ile Gly Asn Ser Val Gly Ala
                 820                 825                 830
Leu Gly Asn Leu Thr Leu Val Leu Ala Ile Ile Val Phe Ile Phe Ala
             835                 840                 845
Val Val Gly Met Gln Leu Phe Gly Lys Ser Tyr Lys Glu Cys Val Cys
850                 855                 860
Lys Ile Asn Asp Asp Cys Thr Leu Pro Arg Trp His Met Asn Asp Phe
865                 870                 875                 880
Phe His Ser Phe Leu Ile Val Phe Arg Val Leu Cys Gly Glu Trp Ile
                 885                 890                 895
Glu Thr Met Trp Asp Cys Met Glu Val Ala Gly Gln Thr Met Cys Leu
                 900                 905                 910
Ile Val Phe Met Leu Val Met Val Ile Gly Asn Leu Val Val Leu Asn
             915                 920                 925
Leu Phe Leu Ala Leu Leu Leu Ser Ser Phe Ser Asp Asn Leu Ala
             930                 935                 940
Ala Thr Asp Asp Asp Asn Glu Met Asn Asn Leu Gln Ile Ala Val Gly
945                 950                 955                 960
Arg Met Gln Lys Gly Ile Asp Tyr Val Lys Asn Lys Met Arg Glu Cys
                 965                 970                 975
Phe Gln Lys Ala Phe Phe Arg Lys Pro Lys Val Ile Glu Ile His Glu
             980                 985                 990
Gly Asn Lys Ile Asp Ser Cys Met Ser Asn Asn Thr Gly Ile Glu Ile
             995                 1000                1005
```

-continued

```
Ser Lys Glu Leu Asn Tyr Leu Arg Asp Gly Asn Gly Thr Thr Ser
    1010                    1015                1020

Gly Val Gly Thr Gly Ser Ser Val Glu Lys Tyr Val Ile Asp Glu
    1025                    1030                1035

Asn Asp Tyr Met Ser Phe Ile Asn Asn Pro Ser Leu Thr Val Thr
    1040                    1045                1050

Val Pro Ile Ala Val Gly Glu Ser Asp Phe Glu Asn Leu Asn Thr
    1055                    1060                1065

Glu Glu Phe Ser Ser Glu Ser Glu Leu Glu Glu Ser Lys Glu Lys
    1070                    1075                1080

Leu Asn Ala Thr Ser Ser Ser Glu Gly Ser Thr Val Asp Val Val
    1085                    1090                1095

Leu Pro Arg Glu Gly Glu Gln Ala Glu Thr Glu Pro Glu Glu Asp
    1100                    1105                1110

Phe Lys Pro Glu Ala Cys Phe Thr Glu Gly Cys Ile Lys Lys Phe
    1115                    1120                1125

Pro Phe Cys Gln Val Ser Thr Glu Glu Gly Lys Gly Lys Ile Trp
    1130                    1135                1140

Trp Asn Leu Arg Lys Thr Cys Tyr Ser Ile Val Glu His Asn Trp
    1145                    1150                1155

Phe Glu Thr Phe Ile Val Phe Met Ile Leu Leu Ser Ser Gly Ala
    1160                    1165                1170

Leu Ala Phe Glu Asp Ile Tyr Ile Glu Gln Arg Lys Thr Ile Lys
    1175                    1180                1185

Thr Met Leu Glu Tyr Ala Asp Lys Val Phe Thr Tyr Ile Phe Ile
    1190                    1195                1200

Leu Glu Met Leu Leu Lys Trp Val Ala Tyr Gly Phe Gln Thr Tyr
    1205                    1210                1215

Phe Thr Asn Ala Trp Cys Trp Leu Asp Phe Leu Ile Val Asp Val
    1220                    1225                1230

Ser Leu Val Ser Leu Val Ala Asn Ala Leu Gly Tyr Ser Glu Leu
    1235                    1240                1245

Gly Ala Ile Lys Ser Leu Arg Thr Leu Arg Ala Leu Arg Pro Leu
    1250                    1255                1260

Arg Ala Leu Ser Arg Phe Glu Gly Met Arg Val Val Val Asn Ala
    1265                    1270                1275

Leu Val Gly Ala Ile Pro Ser Ile Met Asn Val Leu Leu Val Cys
    1280                    1285                1290

Leu Ile Phe Trp Leu Ile Phe Ser Ile Met Gly Val Asn Leu Phe
    1295                    1300                1305

Ala Gly Lys Phe Tyr His Cys Val Asn Met Thr Thr Gly Asn Met
    1310                    1315                1320

Phe Asp Ile Ser Asp Val Asn Asn Leu Ser Asp Cys Gln Ala Leu
    1325                    1330                1335

Gly Lys Gln Ala Arg Trp Lys Asn Val Lys Val Asn Phe Asp Asn
    1340                    1345                1350

Val Gly Ala Gly Tyr Leu Ala Leu Leu Gln Val Ala Thr Phe Lys
    1355                    1360                1365

Gly Trp Met Asp Ile Met Tyr Ala Ala Val Asp Ser Arg Asp Val
    1370                    1375                1380

Lys Leu Gln Pro Val Tyr Glu Glu Asn Leu Tyr Met Tyr Leu Tyr
    1385                    1390                1395

Phe Val Ile Phe Ile Ile Phe Gly Ser Phe Phe Thr Leu Asn Leu
    1400                    1405                1410
```

```
Phe Ile Gly Val Ile Ile Asp Asn Phe Asn Gln Gln Lys Lys Lys
    1415                1420                1425

Phe Gly Gly Gln Asp Ile Phe Met Thr Glu Glu Gln Lys Lys Tyr
    1430                1435                1440

Tyr Asn Ala Met Lys Lys Leu Gly Ser Lys Lys Pro Gln Lys Pro
    1445                1450                1455

Ile Pro Arg Pro Ala Asn Lys Phe Gln Gly Met Val Phe Asp Phe
    1460                1465                1470

Val Thr Arg Gln Val Phe Asp Ile Ser Ile Met Ile Leu Ile Cys
    1475                1480                1485

Leu Asn Met Val Thr Met Met Val Glu Thr Asp Asp Gln Gly Lys
    1490                1495                1500

Tyr Met Thr Leu Val Leu Ser Arg Ile Asn Leu Val Phe Ile Val
    1505                1510                1515

Leu Phe Thr Gly Glu Phe Val Leu Lys Leu Val Ser Leu Arg His
    1520                1525                1530

Tyr Tyr Phe Thr Ile Gly Trp Asn Ile Phe Asp Phe Val Val Val
    1535                1540                1545

Ile Leu Ser Ile Val Gly Met Phe Leu Ala Glu Met Ile Glu Lys
    1550                1555                1560

Tyr Ser Val Ser Pro Thr Leu Phe Arg Val Ile Arg Leu Ala Arg
    1565                1570                1575

Ile Gly Arg Ile Leu Arg Leu Ile Lys Gly Ala Lys Gly Ile Arg
    1580                1585                1590

Thr Leu Leu Phe Ala Leu Met Met Ser Leu Pro Ala Leu Phe Asn
    1595                1600                1605

Ile Gly Leu Leu Leu Phe Leu Val Met Phe Ile Tyr Ala Ile Phe
    1610                1615                1620

Gly Met Ser Asn Phe Ala Tyr Val Lys Lys Glu Ala Gly Ile Asp
    1625                1630                1635

Asp Met Phe Asn Phe Glu Thr Phe Gly Asn Ser Met Ile Cys Leu
    1640                1645                1650

Phe Gln Ile Thr Thr Ser Ala Gly Trp Asp Gly Leu Leu Ala Pro
    1655                1660                1665

Ile Leu Asn Ser Ala Pro Pro Asp Cys Asp Pro Asp Thr Ile His
    1670                1675                1680

Pro Gly Ser Ser Val Lys Gly Asp Arg Gly Asp Pro Ser Val Gly
    1685                1690                1695

Ile Phe Phe Phe Val Ser Tyr Ile Ile Ile Ser Phe Leu Val Val
    1700                1705                1710

Val Asn Met Tyr Ile Ala Val Ile Leu Glu Asn Phe Ser Val Ala
    1715                1720                1725

Thr Glu Glu Ser Ala Glu Pro Leu Ser Glu Asp Asp Phe Glu Met
    1730                1735                1740

Phe Tyr Glu Val Trp Glu Lys Phe Asp Pro Asp Ala Thr Gln Phe
    1745                1750                1755

Ile Glu Phe Ser Lys Leu Ser Asp Phe Ala Ala Ala Leu Asp Pro
    1760                1765                1770

Pro Leu Leu Ile Ala Lys Pro Asn Lys Val Gln Leu Ile Ala Met
    1775                1780                1785

Asp Leu Pro Met Val Ser Gly Asp Arg Ile His Cys Leu Asp Ile
    1790                1795                1800

Leu Phe Ala Phe Thr Lys Arg Val Leu Cys Glu Ser Gly Glu Met
```

```
            1805                1810                1815

Asp Ala Leu Arg Ile Gln Met Glu Asp Arg Phe Met Ala Ser Asn
    1820                1825                1830

Pro Ser Lys Val Ser Tyr Glu Pro Ile Thr Thr Thr Leu Lys Arg
    1835                1840                1845

Lys Gln Glu Glu Val Ser Ala Ala Ile Ile Gln Arg Asn Phe Arg
    1850                1855                1860

Cys Tyr Leu Leu Lys Gln Arg Leu Lys Asn Ile Ser Ser Asn Tyr
    1865                1870                1875

Asn Lys Glu Ala Ile Lys Gly Arg Ile Asp Leu Pro Ile Lys Gln
    1880                1885                1890

Asp Met Ile Ile Asp Lys Leu Asn Gly Asn Ser Thr Pro Glu Lys
    1895                1900                1905

Thr Asp Gly Ser Ser Ser Thr Thr Ser Pro Pro Ser Tyr Asp Ser
    1910                1915                1920

Val Thr Lys Pro Asp Lys Glu Lys Phe Glu Lys Asp Lys Pro Glu
    1925                1930                1935

Lys Glu Ser Lys Gly Lys Glu Val Arg Glu Asn Gln Lys
    1940                1945                1950

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ctacacgtaa ttaaatgtgc                                            20

<210> SEQ ID NO 10
<211> LENGTH: 26
<212> TYPE: DNA
<213> ORGANISM: Artificial Sequence
<220> FEATURE:
<223> OTHER INFORMATION: Synthetic primer

<400> SEQUENCE: 10
aatggatcca taacaattaa attcac                                     26

<210> SEQ ID NO 11
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(5)
<223> OTHER INFORMATION: n is a, c, g, or t

<400> SEQUENCE: 11
nnnnnctcga gaggatgaaa agatggcaca ggc                             33

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
gttttacttt taaccatgca tcac                                       24
```

<210> SEQ ID NO 13
<211> LENGTH: 22
<212> TYPE: DNA
<213> ORGANISM: Artificial Sequence
<220> FEATURE:
<223> OTHER INFORMATION: Sythetic primer

<400> SEQUENCE: 13
atttgccaat gtgttcttga tc                                          22

<210> SEQ ID NO 14
<211> LENGTH: 22
<212> TYPE: DNA
<213> ORGANISM: Artificial Sequence
<220> FEATURE:
<223> OTHER INFORMATION: Synthetic primer

<400> SEQUENCE: 14
ttgtgctcaa caatactgta gc                                          22

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ctgggactgc tgtgatgcat                                             20

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
gaagattcca ccagatcttc c                                           21

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
agaagacctg tcaagtaagt ac                                          22

<210> SEQ ID NO 18
<211> LENGTH: 29
<212> TYPE: DNA
<213> ORGANISM: Artificial Sequence
<220> FEATURE:
<223> OTHER INFORMATION: Synthetic primer

<400> SEQUENCE: 18
cacaaagata attctttgtt tcttttac                                    29

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 19
gaagaaggca aagggaagat c                                          21

<210> SEQ ID NO 20
<211> LENGTH: 38
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(5)
<223> OTHER INFORMATION: n is a, c, g, or t

<400> SEQUENCE: 20
nnnnngcggc cgcttttac ttttgatttt ctctgacc                         38
```